(12) United States Patent
Herbert et al.

(10) Patent No.: US 9,249,421 B2
(45) Date of Patent: Feb. 2, 2016

(54) ARTIFICIAL BIOLOGICAL MATERIALS PRODUCED BY SELF-ASSEMBLY OF PHOTOSYNTHETIC UNICELLS

(71) Applicant: University of Wyoming, Laramie, WY (US)

(72) Inventors: Stephen K. Herbert, Laramie, WY (US); Levi G. Lowder, Laramie, WY (US)

(73) Assignee: University of Wyoming, Laramie, WY (US)

( * ) Notice: Subject to any disclaimer, the term of this patent is extended or adjusted under 35 U.S.C. 154(b) by 246 days.

(21) Appl. No.: 13/772,635

(22) Filed: Feb. 21, 2013

(65) Prior Publication Data

US 2013/0288297 A1    Oct. 31, 2013

Related U.S. Application Data

(60) Provisional application No. 61/603,088, filed on Feb. 24, 2012.

(51) Int. Cl.
| | |
|---|---|
| C12N 15/82 | (2006.01) |
| C07K 14/405 | (2006.01) |
| C12N 5/04 | (2006.01) |
| C12N 15/79 | (2006.01) |
| C12N 1/12 | (2006.01) |

(52) U.S. Cl.
CPC .............. *C12N 15/82* (2013.01); *C07K 14/405* (2013.01); *C12N 1/12* (2013.01); *C12N 5/04* (2013.01); *C12N 15/79* (2013.01); *C12N 15/8242* (2013.01); *C12N 15/8257* (2013.01)

(58) Field of Classification Search
None
See application file for complete search history.

(56) References Cited

U.S. PATENT DOCUMENTS

2011/0151515 A1    6/2011    Heifetz et al.

FOREIGN PATENT DOCUMENTS

| EP | 2389958 A1 | 11/2011 |
|---|---|---|
| WO | 2009158658 A2 | 12/2009 |

OTHER PUBLICATIONS

Schirrmeister et al., 2011, BMC Evolutionary Biology 11:45.*
Hallmann et al., 2006, Plant J. 45: 292-307.*
Lurling and Beekman, 2006, Ann. Limnol.—Int. J. Lim. 42: 65-72.*
Franklin and Mayfield, 2004, Curr. Opinion Plant Biol. 7: 159-165.*
Catt et al., 1978, Planta 138: 91-98.*
GenBank sequence Accession No. ABA41395.1.*
International Search Report for PCT/US2013/027039, Jul. 5, 2013, pp. 1-15.
Baba et al., "Protemic Analysis of High-CO2-Inducible Extracellular Proteins in the Unicellular Green Alga, *Chlamydomonas reinhardtii*", Plant Cell Physiology, Aug. 5, 2011, vol. 52, No. 8, pp. 1302-1314, entire document.
Hallmann et al., "The developmentally regulated ECM glycoprotein ISG plays an essential role in organizing the ECM and orienting the cells of Volvox," Journal of Cell Science, Nov. 10, 2000 (Nov. 16, 2000), vol. 113 pp. 4605-4617, entire document.
Ertl et al., "A novel extensin that may organize extracellular matrix biogenesis in Volvox carteri," The EMBO Journal, Feb. 27, 1992, vol. 11, No. 6, pp. 2055-2062.
Harris EH, 2009, The Chlamydomonas Sourcebook: Introduction to Chlamydomonas and its Laboratory use. Elsevier, pp. 81-83.

* cited by examiner

*Primary Examiner* — Amjad Abraham
*Assistant Examiner* — Bratislav Stankovic
(74) *Attorney, Agent, or Firm* — James M. Weatherly; Cochran Freund & Young, LLC

(57) ABSTRACT

Methods for the self-assembly of photosynthetic unicells into a multicellular shape are provided. DNA constructs as well as methods for integration of the DNA constructs into the genomes of photosynthetic unicells for the expression of cell wall proteins or cell adhesion molecules for the self-assembly of photosynthetic unicells into a multicellular shape are also disclosed.

7 Claims, 17 Drawing Sheets

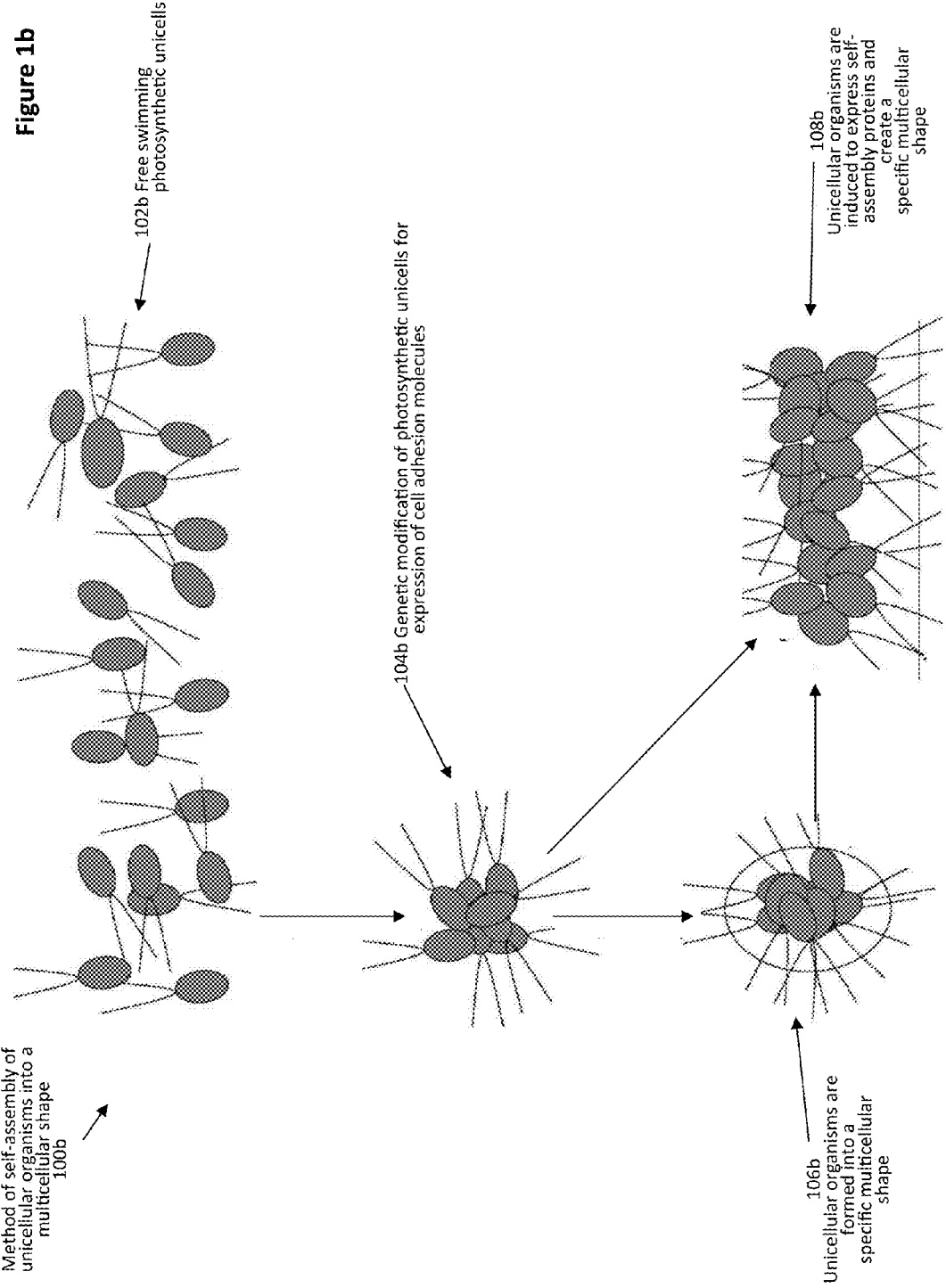

SEQUENCE LISTING

<160> NUMBER OF SEQ ID NOS: 49

<210> SEQ ID NO 1
<211> LENGTH: 1099
<212> TYPE: DNA
<213> ORGANISM: Volvox carteri f. nagariensis

<400> SEQUENCE: 1

| | |
|---|---|
| tgtgcctctg gaggctccct cttttttgggg tccaggccac tgatactcat aagaggcagc | 60 |
| ggatccttct agccgaacgg tctgaaaaga tgggttcgcg tagcgtcgcc acgaccacgc | 120 |
| ggacgttcgg cttgttcgct gcggcatctc tactgctcgc gtgccaagct tccgctgctg | 180 |
| tttcatattc tgtaagcgtc tacaacaaca tcgcggtcac aggggctccc ctctctggca | 240 |
| tcgtgtctca gctgctatcc aaatggaagc tcaatgttcc cactttgagg acagtctact | 300 |
| cccagccgag cgctgcagag ttgtcaagca ccaacgcctt tatcgtatac tccaagggtc | 360 |
| agggctccta ctggattacg gaaggcctga cctcgaactc aactaaggtt aacgatctac | 420 |
| tcacatttgt ccgtaatgga ggttccctta tccttgtcaa cggcgccaac ggaaatgaca | 480 |
| acacatttat tcctcttatt cacgcgctga ctggcgggga tactctctgc atcgcgagga | 540 |
| gctacgcaga tgacactcgc atctaccgtc gcatcgaccc tccatccaac tttggcaacc | 600 |
| tgcctgtcaa gcagttccgc tacactgcgg atctgtatat taccggccta gactgcttat | 660 |
| ctggcacctc tatttattcc tccgacccaa ccaaaaagct ttacgccatc tctgccggca | 720 |
| tcacatggag cgtgggacag ggcgccgtga cgtgggtcgg cgccgacatt gtggctgact | 780 |
| ccaagaacac cgtagccttg gtgacagctg cggcggtcgt cgtacagaca accccgtcgc | 840 |
| cgccgccgcc gccacgagtt tcaacgtcgc cgccgccacc agcccgtgtc tcatcctcgc | 900 |
| cgccgcccgc cacgcgctcg ccgccacccc gtcgtataac gtctccttca ccagtcctca | 960 |
| ctgcatcccc accactcccg aaaagatcgc caccaccgcc gccgcgcgtc ccgccctcgc | 1020 |
| cgccaccacc ggttgcttct ccgccgccac caccacctcc acgcgtctcc ccgtcgccgc | 1080 |
| ctccgccgca gccagtttc | 1099 |

<210> SEQ ID NO 2
<211> LENGTH: 336
<212> TYPE: PRT
<213> ORGANISM: Volvox carteri f. nagariensis

<400> SEQUENCE: 2

Met Gly Ser Arg Ser Val Ala Thr Thr Thr Arg Thr Phe Gly Leu Phe
1               5                   10                  15

Ala Ala Ala Ser Leu Leu Leu Ala Cys Gln Ala Ser Ala Ala Val Ser
            20                  25                  30

Tyr Ser Val Ser Val Tyr Asn Asn Ile Ala Val Thr Gly Ala Pro Leu
        35                  40                  45

Ser Gly Ile Val Ser Gln Leu Leu Ser Lys Trp Lys Leu Asn Val Pro
    50                  55                  60

Thr Leu Arg Thr Val Tyr Ser Gln Pro Ser Ala Ala Glu Leu Ser Ser
65                  70                  75                  80

Thr Asn Ala Phe Ile Val Tyr Ser Lys Gly Gln Gly Ser Tyr Trp Ile
                85                  90                  95

Thr Glu Gly Leu Thr Ser Asn Ser Thr Lys Val Asn Asp Leu Leu Thr
            100                 105                 110

Phe Val Arg Asn Gly Gly Ser Leu Ile Leu Val Asn Gly Ala Asn Gly
        115                 120                 125

```
Asn Asp Asn Thr Phe Ile Pro Leu Ile His Ala Leu Thr Gly Gly Asp
            130                 135                 140

Thr Leu Cys Ile Ala Arg Ser Tyr Ala Asp Asp Thr Arg Ile Tyr Arg
145                 150                 155                 160

Arg Ile Asp Pro Pro Ser Asn Phe Gly Asn Leu Pro Val Lys Gln Phe
                165                 170                 175

Arg Tyr Thr Ala Asp Leu Tyr Ile Thr Gly Leu Asp Cys Leu Ser Gly
            180                 185                 190

Thr Ser Ile Tyr Ser Ser Asp Pro Thr Lys Lys Leu Tyr Ala Ile Ser
        195                 200                 205

Ala Gly Ile Thr Trp Ser Val Gly Gln Gly Ala Val Thr Trp Val Gly
        210                 215                 220

Ala Asp Ile Val Ala Asp Ser Lys Asn Thr Val Ala Leu Val Thr Ala
225                 230                 235                 240

Ala Ala Val Val Gln Thr Thr Pro Ser Pro Pro Pro Pro Arg
                245                 250                 255

Val Ser Thr Ser Pro Pro Pro Ala Arg Val Ser Ser Pro Pro
            260                 265                 270

Pro Ala Thr Arg Ser Pro Pro Arg Arg Ile Thr Ser Pro Ser Pro
            275                 280                 285

Val Leu Thr Ala Ser Pro Pro Leu Pro Lys Arg Ser Pro Pro Pro
290                 295                 300

Pro Arg Val Pro Pro Ser Pro Pro Pro Val Ala Ser Pro Pro Pro
305                 310                 315                 320

Pro Pro Pro Pro Arg Val Ser Pro Ser Pro Pro Pro Gln Pro Val
                325                 330                 335

<210> SEQ ID NO 3
<211> LENGTH: 1773
<212> TYPE: DNA
<213> ORGANISM: Volvox carteri f. nagariensis

<400> SEQUENCE: 3
atggcgaaga caagtaatat gtggaatgct gttgcggcag cttttggcgct gacgtgggtt    60 gctatcgcag tcgcgcaata tgacgaggac ttcacggtct accgggatca acagggggcc   120
ttcccgaact ttccctttcg taattgtgaa accacaaacg gggcatacca actggcacct   180
gtgtggcaac atgtgggcag caacaagtac tgctttagaa tccaggttcg ggaccctagc   240
tcctgcacgg gagcctgctg caacaccgac atgtacaaga tagagttcaa cgtgtccagc   300
agctgcctgg tggccggggc ttcagtcgtt gccaccgtga acggagcacc cactcgggtt   360
ggtgcgtcct tcgacaagcc cccgaccggc ccacctggct ccgccattct gcggctcacc   420
cagctggggc ttgacaccac gaccgcccag aatgcggagg tgtgcatcac cctcaggacc   480
aaccgcggag gccagggctg caccacccctg agcaactgt gctcgtcacc gggctttttct   540 gcaggcacct gtacggcagc gatgtatgac acggcatgtg attgctgccc cacctctaga   600
gcctcgaagt attacccacc acctccaccg cctccaccat ctccatcgcc tccaccatct   660
ccaccgcctc caccatctcc accgcctcca ccctccac cgcctccacc atctccaccg   720
cctccaccac ctccaccgcc tccaccttct ccaccgcctc caccatctcc accgcctcca   780
tctccaccac tgccgccgcc gtcaatcccc tctcctcctt tcgcattcgg attccggcca   840
ttttgcgatg tctgcatcaa ggcacagctg ctggctcctt tccccgatgt ccgaccctct c   900 cgctacagca gcacaatgtg ctctgcaatc cagcagaaga tcgctgacag catcaacgcc   960
```

```
ttggagcaag atccaaacct tggcttcgtc tataggattc catttgcacc gaatgacact    1020
cgctgcacag aaacccaggc tgttgtgtgt ggctcccttt atcagccagt taatgacaca    1080
gacgctttca agagaagct ctctcgctcc gtgagcgacc aggtgctgtt ctggctcgac     1140
gcggctacgg gggccgccag catttgcagc ccggaacttg acgggtacca agtgaccatt    1200
gagatcaccg gtgatgattc aaatgggggc agctgcgtgc aagacagcag gtccatcgcc    1260
tgcactttgc caccagtccc atatcccaac tgcacgtgtg acatgcggca gggcgttatg    1320
ccatttgtgg tgggtacgcg ctacttcgcg cagcccagct ttaaagctga tttcggcacc    1380
accgagtact gcttccctat gagcattttc ccactgagcc agcttgtacc gagcacctgt    1440
aagggtgttg acatcctcaa gaagattgag tggtatgcga atgaggttct cagatcgtat    1500
gtcaagggtt tcaccctcta ccctagggtt ggtagtccac ggtcgatcgc gtccagctgg    1560
ggtgctgccg ggagctatac gctcaaagct accaacatta actggaatac cacgcaagcc    1620
gatggcgcca agatttgtgt ggttgtaaag aatccggtga ccatggcaga gctctgtcta    1680
ggcgcgtttg gaagccaatg tttcgccacg ccatttaatg acgacaagga ctgctgcccc    1740
atgttccgta cggcgccgct gggaggccca taa                                 1773
```

<210> SEQ ID NO 4
<211> LENGTH: 590
<212> TYPE: PRT
<213> ORGANISM: Volvox carteri f. nagariensis

<400> SEQUENCE: 4

```
Met Ala Lys Thr Ser Asn Met Trp Asn Ala Val Ala Ala Leu Ala
1               5                   10                  15

Leu Thr Trp Val Ala Ile Ala Val Ala Gln Tyr Asp Glu Asp Phe Thr
            20                  25                  30

Val Tyr Arg Asp Gln Thr Gly Ala Phe Pro Asn Phe Pro Phe Arg Asn
        35                  40                  45

Cys Glu Thr Thr Asn Gly Ala Tyr Gln Leu Ala Pro Val Trp Gln His
    50                  55                  60

Val Gly Ser Asn Lys Tyr Cys Phe Arg Ile Gln Val Arg Asp Pro Ser
65                  70                  75                  80

Ser Cys Thr Gly Ala Cys Cys Asn Thr Asp Met Tyr Lys Ile Glu Phe
                85                  90                  95

Asn Val Ser Ser Cys Leu Val Ala Gly Ala Ser Val Val Ala Thr
            100                 105                 110

Val Asn Gly Ala Pro Thr Arg Val Gly Ala Ser Phe Asp Lys Pro Pro
        115                 120                 125

Thr Gly Pro Pro Gly Ser Ala Ile Leu Arg Leu Thr Gln Leu Gly Leu
    130                 135                 140

Asp Thr Thr Thr Ala Gln Asn Ala Glu Val Cys Ile Thr Leu Arg Thr
145                 150                 155                 160

Asn Arg Gly Gly Gln Gly Cys Thr Thr Leu Glu Gln Leu Cys Ser Ser
                165                 170                 175

Pro Gly Phe Ser Ala Gly Thr Cys Thr Ala Ala Met Tyr Asp Thr Ala
            180                 185                 190

Cys Asp Cys Cys Pro Thr Ser Arg Ala Ser Lys Tyr Tyr Pro Pro
        195                 200                 205

Pro Pro Pro Pro Pro Ser Pro Ser Pro Pro Ser Pro Pro Pro
    210                 215                 220
```

| | | | | | | | | | | | | | | | |
|---|---|---|---|---|---|---|---|---|---|---|---|---|---|---|---|
| Pro | Ser | Pro | Pro | Pro | Pro | Pro | Pro | Pro | Pro | Pro | Ser | Pro | Pro | | |
| 225 | | | | 230 | | | | 235 | | | | 240 | | | |

Pro Pro Pro Pro Pro Pro Pro Ser Pro Pro Pro Pro Ser
     245                 250                 255

Pro Pro Pro Ser Pro Pro Leu Pro Pro Ser Ile Pro Ser Pro
 260                 265                 270

Pro Phe Ala Phe Gly Phe Arg Pro Phe Cys Asp Val Cys Ile Lys Ala
     275                 280                 285

Gln Leu Leu Ala Pro Phe Pro Asp Val Arg Pro Phe Arg Tyr Ser Ser
     290                 295                 300

Thr Met Cys Ser Ala Ile Gln Gln Lys Ile Ala Asp Ser Ile Asn Ala
305                 310                 315                 320

Leu Glu Gln Asp Pro Asn Leu Gly Phe Val Tyr Arg Ile Pro Phe Ala
             325                 330                 335

Pro Asn Asp Thr Arg Cys Thr Glu Thr Gln Ala Val Val Cys Gly Ser
             340                 345                 350

Leu Tyr Gln Pro Val Asn Asp Thr Asp Ala Phe Lys Glu Lys Leu Ser
         355                 360                 365

Arg Ser Val Ser Asp Gln Val Leu Phe Trp Leu Asp Ala Ala Thr Gly
370                 375                 380

Ala Ala Ser Ile Cys Ser Pro Glu Leu Asp Gly Tyr Gln Val Thr Ile
385                 390                 395                 400

Glu Ile Thr Gly Asp Asp Ser Asn Gly Gly Ser Cys Val Gln Asp Ser
             405                 410                 415

Arg Ser Ile Ala Cys Thr Leu Pro Pro Val Pro Tyr Pro Asn Cys Thr
         420                 425                 430

Cys Asp Met Arg Gln Gly Val Met Pro Phe Val Val Gly Thr Arg Tyr
     435                 440                 445

Phe Ala Gln Pro Ser Phe Lys Ala Asp Phe Gly Thr Thr Glu Tyr Cys
     450                 455                 460

Phe Pro Met Ser Ile Phe Pro Leu Ser Gln Leu Val Pro Ser Thr Cys
465                 470                 475                 480

Lys Gly Val Asp Ile Leu Lys Lys Ile Glu Trp Tyr Ala Asn Glu Val
             485                 490                 495

Leu Arg Ser Tyr Val Lys Gly Phe Thr Leu Tyr Pro Arg Val Gly Ser
         500                 505                 510

Pro Arg Ser Ile Ala Ser Ser Trp Gly Ala Ala Gly Ser Tyr Thr Leu
     515                 520                 525

Lys Ala Thr Asn Ile Asn Trp Asn Thr Thr Gln Ala Asp Gly Ala Lys
     530                 535                 540

Ile Cys Val Val Val Lys Asn Pro Val Thr Met Ala Glu Leu Cys Leu
545                 550                 555                 560

Gly Ala Phe Gly Ser Gln Cys Phe Ala Thr Pro Phe Asn Asp Asp Lys
             565                 570                 575

Asp Cys Cys Pro Met Phe Arg Thr Ala Pro Leu Gly Gly Pro
         580                 585                 590

<210> SEQ ID NO 5
<211> LENGTH: 1029
<212> TYPE: DNA
<213> ORGANISM: Volvox carteri f. nagariensis

<400> SEQUENCE: 5
atgaagctca ccaacgtcct gtgcattgct gtggctgtca gcctgctggc tggcgcccag    60

```
gccgcctcct tcccttacag ctcggtatgc gctcagcagc cggccgtcta ctccgtggag    120
tcgaccatca ttgagcgccc caacaacacc tactgcttta agatcgctgt caacgtgcct    180
gctaactgcg ctggctactg ctgctcggct gacctttaca agttcgagct gagcatcaac    240
cctatctgca agattagcgg cgccaagctg agctctaccc tcaacggcaa gccaaccccc    300
acccagcctt ctatcgacaa ggcccccaac gagccggctg gtgccatcct gcgcattccg    360
aacctgggcc tcaagatgtc caacgccgat ggcgccgaga tttgcgtgag cctgggcacc    420
aactccgccg gcaggggctg cctctcccctg gagcagctct gcaagccacc ggccggcggt    480
gctcccggca cctgcgagac tgccctgtgg gactccaagt tcaagtgctg cccaacggac    540
gttactgtgc ccaactctcc gcttctgccc ccgccccca tcaactgcac gtgcgactac    600
aaggcaggtt ccacgccatt cactgttggc gccgccgcca ctgctacccc caccacttcg    660
ggaaccaccg tgtactgcct gccgatcacc accacgaca ccttcacccc agctggttgc    720
ggcccggtcg acatcctgca caagatcgag atgtacgcaa accaggatca gagggctgcg    780
attaagagcc tgaaactggt ctccggcagc accaccacga ccctcgcggc ctcctggaac    840
ggcgctaaca gcaacactct gaagttcacc ccgatcaact ggaccaaggc tcaggccgcg    900
aactccaagg tctgcgtgga gctcaagaac ccaaccaccc tttcggactt ctgcctcggc    960
agcaagtgct acctcttcat cttcaacgcc aacagggcgt gctgcccgat gtacacggtt   1020
ccggtttaa                                                           1029
```

<210> SEQ ID NO 6
<211> LENGTH: 342
<212> TYPE: PRT
<213> ORGANISM: Volvox carteri f. nagariensis

<400> SEQUENCE: 6

```
Met Lys Leu Thr Asn Val Leu Cys Ile Ala Val Ala Val Ser Leu Leu
1               5                   10                  15

Ala Gly Ala Gln Ala Ala Ser Phe Pro Tyr Ser Ser Val Cys Ala Gln
            20                  25                  30

Gln Pro Ala Val Tyr Ser Val Glu Ser Thr Ile Ile Glu Arg Pro Asn
        35                  40                  45

Asn Thr Tyr Cys Phe Lys Ile Ala Val Asn Val Pro Ala Asn Cys Ala
    50                  55                  60

Gly Tyr Cys Cys Ser Ala Asp Leu Tyr Lys Phe Glu Leu Ser Ile Asn
65                  70                  75                  80

Pro Ile Cys Lys Ile Ser Gly Ala Lys Leu Ser Ser Thr Leu Asn Gly
                85                  90                  95

Lys Pro Thr Pro Thr Gln Pro Ser Ile Asp Lys Ala Pro Asn Glu Pro
            100                 105                 110

Ala Gly Ala Ile Leu Arg Ile Pro Asn Leu Gly Leu Lys Met Ser Asn
        115                 120                 125

Ala Asp Gly Ala Glu Ile Cys Val Ser Leu Gly Thr Asn Ser Ala Gly
    130                 135                 140

Arg Gly Cys Leu Ser Leu Glu Gln Leu Cys Lys Pro Pro Ala Gly Gly
145                 150                 155                 160

Ala Pro Gly Thr Cys Glu Thr Ala Leu Trp Asp Ser Lys Phe Lys Cys
                165                 170                 175

Cys Pro Thr Asp Val Thr Val Pro Asn Ser Pro Leu Leu Pro Pro Pro
            180                 185                 190

Pro Ile Asn Cys Thr Cys Asp Tyr Lys Ala Gly Ser Thr Pro Phe Thr
```

```
                195                 200                 205
Val Gly Ala Ala Ala Thr Ala Thr Pro Thr Thr Ser Gly Thr Thr Val
    210                 215                 220

Tyr Cys Leu Pro Ile Thr Thr Thr Asp Thr Phe Thr Pro Ala Gly Cys
225                 230                 235                 240

Gly Pro Val Asp Ile Leu His Lys Ile Glu Met Tyr Ala Asn Gln Asp
                245                 250                 255

Gln Arg Ala Ala Ile Lys Ser Leu Lys Leu Val Ser Gly Ser Thr Thr
            260                 265                 270

Thr Thr Leu Ala Ala Ser Trp Asn Gly Ala Asn Ser Asn Thr Leu Lys
        275                 280                 285

Phe Thr Pro Ile Asn Trp Thr Lys Ala Gln Ala Ala Asn Ser Lys Val
    290                 295                 300

Cys Val Glu Leu Lys Asn Pro Thr Thr Leu Ser Asp Phe Cys Leu Gly
305                 310                 315                 320

Ser Lys Cys Tyr Leu Phe Ile Phe Asn Ala Asn Arg Ala Cys Cys Pro
                325                 330                 335

Met Tyr Thr Val Pro Val
            340

<210> SEQ ID NO 7
<211> LENGTH: 5298
<212> TYPE: DNA
<213> ORGANISM: Artificial Sequence
<220> FEATURE:
<223> OTHER INFORMATION: Synthetic Organism

<400> SEQUENCE: 7
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcttgaca tgattggtgc gtatgtttgt atgaagctac aggactgatt    180
tggcgggcta tgagggcgcg gaagctctg aagggccgc gatggggcgc gcggcgtcca    240
gaaggcgcca tacggcccgc tggcggcacc catccggtat aaaagcccgc gacccccgaac    300 ggtgacctcc actttcagcg acaaacgagc acttatacat acgcgactat tctgccgcta    360
tacataacca ctcagctagc ttaagatccc atcaagcttg catgccgggc gcgccagaag    420
gagcgcagcc aaaccaggat gatgtttgat ggggtatttg agcacttgca acccttatcc    480
ggaagccccc tggcccacaa aggctaggcg ccaatgcaag cagttcgcat gcagcccctg    540
gagcggtgcc tcctgataa accggccagg gggcctatgt tctttacttt tttacaagag    600
aagtcactca acatcttaaa atggccaggt gagtcgacga gcaagcccgg cggatcaggc    660
agcgtgcttg cagatttgac ttgcaacgcc cgcattgtgt cgacgaaggc ttttggctcc    720
tctgtcgctg tctcaagcag catctaaccc tgcgtcgccg tttccatttg caggatggcc    780
actccgccct cccggtgct gaagaattc gaagcatgga cgatgcgttg cgtgcactgc    840
ggggtcggta tccggtt gt gagtgggttg ttgtggagga tggggcctcg ggggctggtg    900
tttatcggct tcgggtggt gggcgggagt tgtttgtcaa ggtggcagct ctggggccg    960 gggtgggctt gttgggtgag gctgagcggc tggtgtggtt gcggaggtg gggattcccg   1020 tacctcgtgt tgtggagggt ggtggggacg agagggtcgc ctggttggtc accgaagcgg   1080
ttccggggcg tccggccagt gcgcggtggc cgcgggagca gcggctggac gtggcggtgg   1140
cgctcgcggg gctcgctcgt tcgctgcacg cgctggactg ggagcggtgt ccgttcgatc   1200
```

```
gcagtctcgc ggtgacggtg ccgcaggcgg cccgtgctgt cgctgaaggg agcgtcgact   1260
tggaggatct ggacgaggag cggaaggggt ggtcggggga gcggcttctc gccgagctgg   1320
agcggactcg gcctgcggac gaggatctgg cggtttgcca cggtcacctg tgcccggaca   1380
acgtgctgct cgaccctcgt acctgcgagg tgaccgggct gatcgacgtg gggcgggtcg   1440
gccgtgcgga ccggcactcc gatctcgcgc tggtgctgcg cgagctggcc cacgaggagg   1500
acccgtggtt cgggccggag tgttccgcgg cgttcctgcg ggagtacggg cgcggtgggg   1560
atggggcggt atcggaggaa aagctggcgt tttaccggct gttggacgag ttcttctgag   1620
ggacctgatg gtgttggtgg ctgggtaggg ttgcgtcgcg tgggtgacag cacagtgtgg   1680
acgttgggat ccccgctccg tgtaaatgga ggcgctcgtt gatctgagcc ttgcccctg    1740 acgaacggcg gtggatggaa gatactgctc tcaagtgctg aagcggtagc ttagctcccc   1800
gtttcgtgct gatcagtctt tttcaacacg taaaaagcgg aggagttttg caattttgtt   1860
ggttgtaacg atcctccgtt gattttggcc tctttctcca tgggcgggct gggcgtattt   1920
gaagcgggta cccagctttt gttccctttt gtgagggtta attgcgcgct tggcgtaatc   1980
atggtcatag ctgtttcctg tgtgaaattg ttatccgctc acaattccac acaacatacg   2040
agccggaagt ctagacggcg gggagctcgc tgaggcttga catgattggt gcgtatgttt   2100
gtatgaagct acaggactga tttggcgggc tatgagggcg cgggaagctc tggaagggcc   2160
gcgatggggc gcgcggcgtc cagaaggcgc catacgcccc gctggcggca ccatccggt    2220 ataaaagccc gcgaccccga acggtgacct ccactttcag cgacaaacga gcacttatac   2280
atacgcgact attctgccgc tatacataac cactcagcta gcttaagatc ccatcaagct   2340
tgcatgccgg gcgcgccaga aggagcgcag ccaaaccagg atgatgtttg atggggtatt   2400
tgagcacttg caacccttat ccggaagccc cctggcccac aaaggctagg cgccaatgca   2460
agcagttcgc atgcagcccc tggagcggtg ccctcctgat aaaccggcca gggggcctat   2520
gttctttact ttttttacaag agaagtcact caacatctta aaatggccag gtgagtcgac   2580
gagcaagccc ggcggatcag gcagcgtgct tgcagatttg acttgcaacg cccgcattgt   2640
gtcgacgaag gcttttggct cctctgtcgc tgtctcaagc agcatctaac cctgcgtcgc   2700
cgtttccatt tgcaggatgg ccactccgcc ctccccggtg ctgaagaatt cgaaattaa    2760 ccctcactaa agggaacaaa agctgggtac cgggcccccc ctcgaggtcg acggtatcga   2820
taagcttgat atcgaattcc tgcagcccgg gggatccccg ctccgtgtaa atggaggcgc   2880
tcgttgatct gagccttgcc ccctgacgaa cggcggtgga tggaagatac tgctctcaag   2940
tgctgaagcg gtagcttagc tccccgtttc gtgctgatca gtctttttca acacgtaaaa   3000
agcggaggag ttttgcaatt tgttggttg taacgatcct ccgttgattt tggcctcttt    3060
ctccatgggc gggctgggcg tatttgaagc gggtacccag cttttgttcc ctttagtgag   3120
ggttaattgc gcgcttggcg taatcatggt catagctgtt tcctgtgtga aattgttatc   3180
cgctcacaat tccacacaac atacgagccg aagcataaa gtgtaaagcc tggggtgcct    3240
aatgagtgag ctaactcaca ttaattgcgt tgcgctcact gcccgctttc cagtcgggaa   3300
acctgtcgtg ccagctgcat taatgaatcg gccaacgcgc ggggagaggc ggtttgcgta   3360
ttgggcgctc ttccgcttcc tcgctcactg actcgctgcg ctcggtcgtt cggctgcggc   3420
gagcggtatc agctcactca aaggcggtaa tacggttatc cacagaatca ggggataacg   3480
caggaaagaa catgtgagca aaaggccagc aaaaggccag gaaccgtaaa aaggccgcgt   3540
tgctggcgtt tttccatagg ctccgccccc ctgacgagca tcacaaaaat cgacgctcaa   3600
```

```
gtcagaggtg gcgaaacccg acaggactat aaagatacca ggcgtttccc cctggaagct    3660
ccctcgtgcg ctctcctgtt ccgaccctgc cgcttaccgg atacctgtcc gcctttctcc    3720
cttcgggaag cgtggcgctt tctcatagct cacgctgtag gtatctcagt tcggtgtagg    3780
tcgttcgctc caagctgggc tgtgtgcacg aaccccccgt tcagcccgac cgctgcgcct    3840
tatccggtaa ctatcgtctt gagtccaacc cggtaagaca cgacttatcg ccactggcag    3900
cagccactgg taacaggatt agcagagcga ggtatgtagg cggtgctaca gagttcttga    3960
agtggtggcc taactacggc tacactagaa ggacagtatt tggtatctgc gctctgctga    4020
agccagttac cttcggaaaa agagttggta gctcttgatc cggcaaacaa accaccgctg    4080
gtagcggtgg tttttttgtt tgcaagcagc agattacgcg cagaaaaaaa ggatctcaag    4140
aagatccttt gatcttttct acggggtctg acgctcagtg gaacgaaaac tcacgttaag    4200
ggattttggt catgagatta tcaaaaagga tcttcaccta gatcctttta aattaaaaat    4260
gaagttttaa atcaatctaa agtatatatg agtaaacttg gtctgacagt taccaatgct    4320
taatcagtga ggcacctatc tcagcgatct gtctatttcg ttcatccata gttgcctgac    4380
tccccgtcgt gtagataact acgatacggg agggcttacc atctggcccc agtgctgcaa    4440
tgataccgcg agacccacgc tcaccggctc cagatttatc agcaataaac cagccagccg    4500
gaagggccga gcgcagaagt ggtcctgcaa ctttatccgc ctccatccag tctattaatt    4560
gttgccggga agctagagta agtagttcgc cagttaatag tttgcgcaac gttgttgcca    4620
ttgctacagg catcgtggtg tcacgctcgt cgtttggtat ggcttcattc agctccggtt    4680
cccaacgatc aaggcgagtt acatgatccc ccatgttgtg caaaaaagcg gttagctcct    4740
tcggtcctcc gatcgttgtc agaagtaagt tggccgcagt gttatcactc atggttatgg    4800
cagcactgca taattctctt actgtcatgc catccgtaag atgcttttct gtgactggtg    4860
agtactcaac caagtcattc tgagaatagt gtatgcggcg accgagttgc tcttgcccgg    4920
cgtcaatacg ggataatacc gcgccacata gcagaacttt aaaagtgctc atcattggaa    4980
aacgttcttc ggggcgaaaa ctctcaagga tcttaccgct gttgagatcc agttcgatgt    5040
aacccactcg tgcacccaac tgatcttcag catcttttac tttcaccagc gtttctgggt    5100
gagcaaaaac aggaaggcaa aatgccgcaa aaagggaat aagggcgaca cggaaatgtt    5160
gaatactcat actcttcctt tttcaatatt attgaagcat ttatcagggt tattgtctca    5220
tgagcggata catatttgaa tgtatttaga aaaataaaca ataggggtt ccgcgcacat    5280 ttccccgaaa agtgccac                                                  5298

<210> SEQ ID NO 8
<211> LENGTH: 5808
<212> TYPE: DNA
<213> ORGANISM: Artificial Sequence
<220> FEATURE:
<223> OTHER INFORMATION: Synthetic Organism

<400> SEQUENCE: 8
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggctttccc cgtcaagctc taaatcgggg gctcccttta gggttccgat     180
ttagtgcttt acggcacctc gaccccaaaa aacttgatta gggtgatggt tcacgtagtg     240
ggccatcgcc ctgatagacg gtttttcgcc ctttgacgtt ggagtccacg ttctttaata     300
```

```
gtggactctt gttccaaact ggaacaacac tcaaccctat ctcggtctat tcttttgatt       360
tataagggat tttgccgatt tcggcctatt ggttaaaaaa tgagctgatt taacaaaaat       420
ttaacgcgaa ttttaacaaa atattaacgc ttacaatttc cattcgccat tcaggctgcg       480
caactgttgg gaagggcgat cggtgcgggc ctcttcgcta ttacgccagc tggcgaaagg       540
gggatgtgct gcaaggcgat taagttgggt aacgccaggg ttttcccagt cacgacgttg       600
taaaacgacg ccagtgagc gcgcgtaata cgactcacta tagggcgaat ggagctcgc        660 tgaggcttga catgattggt gcgtatgttt gtatgaagct acaggactga tttggcgggc       720
tatgagggcg ggggaagctc tggaagggcc gcgatgggc gcgcggcgtc cagaaggcgc        780
catacggccc gctggcggca cccatccggt ataaaagccc gcgaccccga acggtgacct       840
ccactttcag cgacaaacga gcacttatac atacgcgact attctgccgc tatacataac       900
cactcagcta gcttaagatc ccatcaagct tgcattccgg gcgcgccaga aggagcgcag       960
ccaaaccagg atgatgtttg atggggtatt tgagcacttg caacccttat ccggaagccc      1020
cctggcccac aaaggctagg cgccaatgca agcagttcgc atgcagcccc tggagcggtg      1080
ccctcctgat aaaccggcca gggggcctat gttctttact tttttacaag agaagtcact      1140
caacatctta aaatggccag gtgagtcgac gagcaagccc ggcggatcag cagcgtgct       1200 tgcagatttg acttgcaacg cccgcattgt gtcgacgaag cttttggct cctctgtcgc       1260 tgtctcaagc agcatctaac cctgcgtcgc cgtttccatt tgcaggatgc tcgagggaag      1320
atctatgcgg atggcaatcg ctgccttcat gaactacctt ctcgcgtgcg caggtctgct      1380
tcttttcctt acgcctgcat ggaaaagcaa tgttcttgct tttacgtatc cgcctctgat      1440
agcctcgccg tcgtccttca catcgcctcc gttaccatct acgccatcac ctccaccacc      1500
actactgccg gccctagcaa gtcctcctcc gccgccgcct aacgaggatg tcgaccggcc      1560 gccctggtt aaggacaaca cgccaacaag tcccgcatcc agccagccgg caataccacc       1620
tccctcgccc ccaccgtcta cccctcccac ccctcctgtc agctactctt ccatctggga      1680
tttccttgtc aagaacaaca gcttcccaac gatcagtctt gccttgtcga ccgcaaatga      1740
agtcgcaacc ttcaacgact ccagccagga ggtgaccttc ttcctgccca ctgagacggc      1800
ttttgacaag ttgtcggacg cgctgggcgt tgccaggagc aaccgtgcgg gtttgttgcc      1860
gtacttgccg gttatcaaaa gagccctaag ctatcacgtg ctaccgacca gaattagcct      1920
tcagagtgtt gcgaatcaat cagtcggcgg tacggagtac tacaacacca cgcttacgat      1980
gggacagtcc tcaagcatcg gcgtgcgggt ttcgcctccc tcgagccccc ggcgacatc       2040 cccggagata ttcattctgg gggttagctc aaccgctaaa gtactgcagg ctgatgtcgc      2100
ggcaggcgcg tcgtgcatta atgtcgtgga taccgttttg cagtattggt acaactcagt      2160
tgatgaggtc ttcgcctcca tcagcggcgc ctcgaccatg taccaggcgc tcaagaccgc      2220
ccaacttctc aagccagcga atgtgacgag cccgtacacc atattcgtac caaccgacga      2280
ggccttcgtc agcgccttcg gtgcctccgc cgctaccacc atcctcgcca atctaaggtc      2340
gtacgaaagc ttgctacgtc accatgtggc atacggctgg gtggttacgg acacaacctc      2400
agaagaatac gttcgtacat cgtacataac tctgaattcg aacaacgtga cggttgtggt      2460
tccatcgaac gacaaggccg atgctggcgt caagcccacc gtcgcctcag ctgccgtacc      2520
cggatcccca gtcttctcca tcctaaatac attccaagtc ggcatcgagc cacaagtgat      2580
cgtccaagtg attaatgggg ttcttaaccc ggctagcagt cggcagacag ccggtggcgc      2640
agcgatggcc aagggcgagg agctgttcac cggtgtggtc cccatcctgg tggagctgga      2700
```

```
cggcgacgtg aacggccaca agttctccgt ctccggcgag ggtgagggtg acgccaccta    2760
cggcaagctg accctgaagt tcatctgcac caccggcaag ctgcccgtgc cctggcccac    2820
cctggtcacc accctgacct acggtgtgca gtgcttctcc cgctacctcg accacatgaa    2880
```

```
cggcgacgtg aacggccaca agttctccgt ctccggcgag ggtgagggtg acgccaccta    2760
cggcaagctg accctgaagt tcatctgcac caccggcaag ctgcccgtgc cctggcccac    2820
cctggtcacc accctgacct acggtgtgca gtgcttctcc cgctacccg  accacatgaa    2880 gcagcacgac ttcttcaagt ccgccatgcc cgagggctac gtgcaggagc gcaccatctt    2940
cttcaaggac gacggcaact acaagacccg cgccgaggtc aagttcgagg gcgacaccct    3000
ggtgaaccgc atcgagctga agggcatcga cttcaaggag gacggcaaca tcctgggcca    3060
caagctggag tacaactaca actcccacaa cgtgtacatc atggccgaca agcagaagaa    3120
cggcatcaag gtgaacttca agatccgcca caacatcgag gacggctccg tgcagctggc    3180
cgaccactac cagcagaaca cccccatcgg cgatggcccc gtgctgctgc ccgacaacca    3240
ctacctgtcc atccagtccg ccctgtccaa ggacccaaac gagaagcgcg accacatggt    3300
cctgctggag ttcgtcaccg ctgccggcat cacccacggc atggacgagc tgtacaagta    3360
aggatccccg ctccgtgtaa atggaggcgc tcgttgatct gagccttgcc ccctgacgaa    3420
cggcggtgga tggaagatac tgctctcaag tgctgaagcg gtagcttagc tccccgtttc    3480
gtgctgatca gtcttttttca acacgtaaaa agcggaggga ttttgcaatt ttgttggttg    3540
taacgatcct ccgttgattt tggcctcttt ctccatgggc gggctgggcg tatttgaagc    3600
gggtacccag cttttgttcc ctttagtgag ggttaattgc gcgcttggcg taatcatggt    3660
catagctgtt tcctgtgtga aattgttatc cgctcacaat tccacacaac atacgagccg    3720
gaagcataaa gtgtaaagcc tggggtgcct aatgagtgag ctaactcaca ttaattgcgt    3780
tgcgctcact gcccgctttc cagtcgggaa acctgtcgtg ccagctgcat taatgaatcg    3840
gccaacgcgc ggggagaggc ggtttgcgta ttgggcgctc ttccgcttcc tcgctcactg    3900
actcgctgcg ctcggtcgtt cggctgcggc gagcggtatc agctcactca aaggcggtaa    3960
tacggttatc cacagaatca ggggataacg caggaaagaa catgtgagca aaaggccagc    4020
aaaaggccag gaaccgtaaa aaggccgcgt tgctggcgtt tttccatagg ctccgccccc    4080
ctgacgagca tcacaaaaat cgacgctcaa gtcagaggtg gcgaaacccg acaggactat    4140
aaagatacca ggcgtttccc cctggaagct ccctcgtgcg ctctcctgtt ccgaccctgc    4200
cgcttaccgg atacctgtcc gcctttctcc cttcgggaag cgtggcgctt tctcatagct    4260
cacgctgtag gtatctcagt tcggtgtagg tcgttcgctc caagctgggc tgtgtgcacg    4320
aaccccccgt tcagcccgac cgctgcgcct tatccggtaa ctatcgtctt gagtccaacc    4380
cggtaagaca cgacttatcg ccactggcag cagccactgg taacaggatt agcagagcga    4440
ggtatgtagg cggtgctaca gagttcttga agtggtggcc taactacggc tacactagaa    4500
ggacagtatt tggtatctgc gctctgctga agccagttac cttcggaaaa agagttggta    4560
gctcttgatc cggcaaacaa accaccgctg gtagcggtgg tttttttgtt tgcaagcagc    4620
agattacgcg cagaaaaaaa ggatctcaag aagatccttt gatcttttct acggggtctg    4680
acgctcagtg gaacgaaaac tcacgttaag ggattttggt catgagatta tcaaaaagga    4740
tcttcaccta gatcctttta aattaaaaat gaagttttaa atcaatctaa agtatatatg    4800
agtaaacttg gtctgacagt taccaatgct taatcagtga ggcacctatc tcagcgatct    4860
gtctatttcg ttcatccata gttgcctgac tccccgtcgt gtagataact acgatacggg    4920
agggcttacc atctggcccc agtgctgcaa tgataccgcg agacccacgc tcaccggctc    4980
cagatttatc agcaataaac cagccagccg gaagggccga gcgcagaagt ggtcctgcaa    5040
```

| | | |
|---|---|---|
| ctttatccgc ctccatccag tctattaatt gttgccggga agctagagta agtagttcgc | 5100 |
| cagttaatag tttgcgcaac gttgttgcca ttgctacagg catcgtggtg tcacgctcgt | 5160 |
| cgtttggtat ggcttcattc agctccggtt cccaacgatc aaggcgagtt acatgatccc | 5220 |
| ccatgttgtg caaaaaagcg gttagctcct tcggtcctcc gatcgttgtc agaagtaagt | 5280 |
| tggccgcagt gttatcactc atggttatgg cagcactgca taattctctt actgtcatgc | 5340 |
| catccgtaag atgcttttct gtgactggtg agtactcaac caagtcattc tgagaatagt | 5400 |
| gtatgcggcg accgagttgc tcttgcccgg cgtcaatacg ggataatacc gcgccacata | 5460 |
| gcagaacttt aaaagtgctc atcattggaa aacgttcttc ggggcgaaaa ctctcaagga | 5520 |
| tcttaccgct gttgagatcc agttcgatgt aacccactcg tgcacccaac tgatcttcag | 5580 |
| catcttttac tttcaccagc gtttctgggt gagcaaaaac aggaaggcaa aatgccgcaa | 5640 |
| aaaagggaat aagggcgaca cggaaatgtt gaatactcat actcttcctt tttcaatatt | 5700 |
| attgaagcat ttatcagggt tattgtctca tgagcggata catatttgaa tgtatttaga | 5760 |
| aaaataaaca aataggggtt ccgcgcacat ttccccgaaa agtgccac | 5808 |

<210> SEQ ID NO 9
<211> LENGTH: 820
<212> TYPE: DNA
<213> ORGANISM: Chlamydomonas sp.

<400> SEQUENCE: 9

| | | |
|---|---|---|
| ggatcccaca cacctgcccg tctgcctgac aggaagtgaa cgcatgtcga gggaggcctc | 60 |
| accaatcgtc acacgagccc tcgtcagaaa cacgtctccg ccacgctctc cctctcacgg | 120 |
| ccgaccccgc agccctttg cccttttccta ggccaccgac aggacccagg cgctctcagc | 180 |
| atgcctcaac aacccgtact cgtgccagcg gtgcccttgt gctggtgatc gcttggaagc | 240 |
| gcatgcgaag acgaagggc ggagcaggcg gcctggctgt tcgaagggct cgccgccagt | 300 |
| tcgggtgcct ttctccacgc gcgcctccac acctaccgat gcgtgaaggc aggcaaatgc | 360 |
| tcatgtttgc ccgaactcgg agtccttaaa aagccgcttc ttgtcgtcgt tccgagacat | 420 |
| gttagcagat cgcagtgcca ccttttcctga cgcgctcggc cccatattcg gacgcaattg | 480 |
| tcatttgtag cacaattgga gcaaatctgg cgaggcagta ggcttttaag ttgcaaggcg | 540 |
| agagagcaaa gtgggacgcg gcgtgattat tggtatttac gcgacggccc ggcgcgttag | 600 |
| cggcccttcc cccaggccag ggacgattat gtatcaatat tgttgcgttc gggcactcgt | 660 |
| gcgagggctc ctgcgggctg ggaggggga tctgggaatt ggaggtacga ccagatggc | 720 |
| ttgctcgggg ggaggtttcc tcgccagca agccagggtt aggtgttgcg ctcttgactc | 780 |
| gttgtgcatt ctaggacccc actgctactc acaacaagcc | 820 |

<210> SEQ ID NO 10
<211> LENGTH: 29
<212> TYPE: DNA
<213> ORGANISM: Chlamydomonas sp.

<400> SEQUENCE: 10

| | |
|---|---|
| acgggagctc ggatcccaca cacctgccc | 29 |

<210> SEQ ID NO 11
<211> LENGTH: 58
<212> TYPE: DNA
<213> ORGANISM: Chlamydomonas sp

<400> SEQUENCE: 11

```
ctcgagtagc agtcatatgt agtccgtgcg gccgcggctt gttgtgagta gcagtggg      58
```

<210> SEQ ID NO 12
<211> LENGTH: 274
<212> TYPE: DNA
<213> ORGANISM: Chlamydomonas sp.

<400> SEQUENCE: 12

```
gagctgtcgc atagatcgcc tttgcgctcg caactccccg ttgcttttga gccctcgccg      60
ccctctgcgc cctcctcgct gtaacgcaag actcgacatt gctaattggc atcggcttct     120
ctcgctctct ggcgacgact gctgcggcgc tggccttatc attcgggcat gtcactgacg     180 ccctcgcat cggcccgcgc ccgcgctgct cgcccgcccg cctcctcccc cctgcccctc      240
ctttctcaac cttccagaac cttcttcacc aaag                                274
```

<210> SEQ ID NO 13
<211> LENGTH: 38
<212> TYPE: DNA
<213> ORGANISM: Chlamydomonas sp.

<400> SEQUENCE: 13

```
aataatgcgg ccgcgagctg tcgcatagat cgcctttg                             38
```

<210> SEQ ID NO 14
<211> LENGTH: 36
<212> TYPE: DNA
<213> ORGANISM: Chlamydomonas sp.

<400> SEQUENCE: 14

```
aataatcata tgctttggtg aagaaggttc tggaag                               36
```

<210> SEQ ID NO 15
<211> LENGTH: 24
<212> TYPE: DNA
<213> ORGANISM: Chlamydomonas sp.

<400> SEQUENCE: 15

```
gagctgtcgc atagatcgcc tttg                                            24
```

<210> SEQ ID NO 16
<211> LENGTH: 24
<212> TYPE: DNA
<213> ORGANISM: Chlamydomonas sp.

<400> SEQUENCE: 16

```
ctttggtgaa gaaggttctg gaag                                            24
```

<210> SEQ ID NO 17
<211> LENGTH: 1406
<212> TYPE: DNA
<213> ORGANISM: Volvox carteri f. nagariensis

<400> SEQUENCE: 17

```
ataattgctg gaaatgagag cccccagcat caacttacag gccttatttt aaaagacaca      60
gtattggatt ccaacagaga actatgcgga tggcaatcgc tgccttcatg aactaccttc     120
tcgcgtgcgc aggtctgctt ctttttcctta cgcctgcatg gaaaagcaat gttcttgctt    180
ttacgtatcc gcctctgata gcctcgccgt cgtccttcac atcgcctccg ttaccatcta    240
cgccatcacc tccaccacca ctactgccgg ccctagcaag tcctcctccg ccgccgccta    300
```

-continued

```
acgaggatgt cgaccggccg ccctggtta aggacaacac gccaacaagt cccgcatcca   360
gccagccggc aataccacct ccctcgccgc caccgtctac ccctcccacc cctcctgtca   420
gctactcttc catctgggat tccttgtca agaacaacag cttcccaacg atcagtcttg   480
ccttgtcgac cgcaaatgaa gtcgcaacct tcaacgactc cagccaggag gtgaccttct   540
tcctgcccac tgagacggct tttgacaagt tgtcggacgc gctgggcgtt gccaggagca   600
accgtgcggg tttgttgccg tacttgccgg ttatcaaaag agccctaagc tatcacgtgc   660
taccgaccag aattagcctt cagagtgttg cgaatcaatc agtcggcggt acggagtact   720
acaacaccac gcttacgatg ggacagtcct caagcatcgg cgtgcgggtt cgcctccct   780
cgagccccc ggcgacatcc ccggagatat tcattctggg ggttagctca accgctaaag   840
tactgcaggc tgatgtcgcg gcaggcgcgt cgtgcattaa tgtcgtggat ccgttttgc   900
agtattggta caactcagtt gatgaggtct tcgcctccat cagcggcgcc tcgaccatgt   960
accaggcgct caagaccgcc caacttctca agccagcgaa tgtgacgagc ccgtacacca   1020
tattcgtacc aaccgacgag gccttcgtca gcgccttcgg tgcctccgcc gctaccacca   1080
tcctcgccaa tctaaggtcg tacgaaagct tgctacgtca ccatgtggca tacggctggg   1140
tggttacgga cacaacctca gaagaatacg ttcgtacatc gtacataact ctgaattcga   1200
acaacgtgac ggttgtggtt ccatcgaacg acaaggccga tgctggcgtc aagcccaccg   1260
tcgcctcagc tgccgtaccc ggatcccag tcttctccat cctaaataca ttccaagtcg   1320
gcatcgagcc acaagtgatc gtccaagtga ttaatggggt tcttaacccg gctagcagtc   1380
ggcagacagc cggtggcgca gcgtga                                       1406
```

<210> SEQ ID NO 18
<211> LENGTH: 440
<212> TYPE: PRT
<213> ORGANISM: Volvox carteri f. nagariensis

<400> SEQUENCE: 18

```
Met Arg Met Ala Ile Ala Ala Phe Met Asn Tyr Leu Leu Ala Cys Ala
1               5                   10                  15

Gly Leu Leu Leu Phe Leu Thr Pro Ala Trp Lys Ser Asn Val Leu Ala
            20                  25                  30

Phe Thr Tyr Pro Pro Leu Ile Ala Ser Pro Ser Ser Phe Thr Ser Pro
        35                  40                  45

Pro Leu Pro Ser Thr Pro Ser Pro Pro Pro Leu Leu Pro Ala Leu
    50                  55                  60

Ala Ser Pro Pro Pro Pro Pro Asn Glu Asp Val Asp Arg Pro Pro
65                  70                  75                  80

Leu Val Lys Asp Asn Thr Pro Thr Ser Pro Ala Ser Ser Gln Pro Ala
                85                  90                  95

Ile Pro Pro Pro Ser Pro Pro Ser Thr Pro Pro Thr Pro Val
            100                 105                 110

Ser Tyr Ser Ser Ile Trp Asp Phe Leu Val Lys Asn Asn Ser Phe Pro
        115                 120                 125

Thr Ile Ser Leu Ala Leu Ser Thr Ala Asn Glu Val Ala Thr Phe Asn
    130                 135                 140

Asp Ser Ser Gln Glu Val Thr Phe Phe Leu Pro Thr Glu Thr Ala Phe
145                 150                 155                 160

Asp Lys Leu Ser Asp Ala Leu Gly Val Ala Arg Ser Asn Arg Ala Gly
                165                 170                 175
```

```
Leu Leu Pro Tyr Leu Pro Val Ile Lys Arg Ala Leu Ser Tyr His Val
            180                 185                 190
Leu Pro Thr Arg Ile Ser Leu Gln Ser Val Ala Asn Gln Ser Val Gly
        195                 200                 205
Gly Thr Glu Tyr Tyr Asn Thr Thr Leu Thr Met Gly Gln Ser Ser Ser
    210                 215                 220
Ile Gly Val Arg Val Ser Pro Pro Ser Ser Pro Ala Thr Ser Pro
225                 230                 235                 240
Glu Ile Phe Ile Leu Gly Val Ser Ser Thr Ala Lys Val Leu Gln Ala
                245                 250                 255
Asp Val Ala Ala Gly Ala Ser Cys Ile Asn Val Asp Thr Val Leu
            260                 265                 270
Gln Tyr Trp Tyr Asn Ser Val Asp Glu Val Phe Ala Ser Ile Ser Gly
        275                 280                 285
Ala Ser Thr Met Tyr Gln Ala Leu Lys Thr Ala Gln Leu Leu Lys Pro
    290                 295                 300
Ala Asn Val Thr Ser Pro Tyr Thr Ile Phe Val Pro Thr Asp Glu Ala
305                 310                 315                 320
Phe Val Ser Ala Phe Gly Ala Ser Ala Ala Thr Thr Ile Leu Ala Asn
                325                 330                 335
Leu Arg Ser Tyr Glu Ser Leu Leu Arg His His Val Ala Tyr Gly Trp
            340                 345                 350
Val Val Thr Asp Thr Thr Ser Glu Glu Tyr Val Arg Thr Ser Tyr Ile
        355                 360                 365
Thr Leu Asn Ser Asn Asn Val Thr Val Val Pro Ser Asn Asp Lys
    370                 375                 380
Ala Asp Ala Gly Val Lys Pro Thr Val Ala Ser Ala Val Pro Gly
385                 390                 395                 400
Ser Pro Val Phe Ser Ile Leu Asn Thr Phe Gln Val Gly Ile Glu Pro
                405                 410                 415
Gln Val Ile Val Gln Val Ile Asn Gly Val Leu Asn Pro Ala Ser Ser
            420                 425                 430
Arg Gln Thr Ala Gly Gly Ala Ala
        435                 440

<210> SEQ ID NO 19
<211> LENGTH: 3088
<212> TYPE: DNA
<213> ORGANISM: Volvox carteri f. nagariensis

<400> SEQUENCE: 19
ataattgctg gaaatgagag cccccagcat caacttacag gccttatttt aaaagacaca      60
gtattggatt ccaacagaga actatgcgga tggcaatcgc tgccttcatg aactaccttc     120
tcgcgtgcgc aggtctgctt ctttcctta cgcctgcatg gaaaagcaat gttcttgctt     180
ttacgtatcc gcctctgata gcctcgccgt cgtccttcac atcgcctccg ttaccatcta     240
cgccatcacc tccaccacca ctactgccgg ccctagcaag tcctcctccg ccgccgccta     300
acgaggatgt cgaccggccg cccctggtta aggacaacac gccaacaagt cccgcatcca     360
gccagccggc aataccacct ccctcgccgc caccgtctac ccctcccacc ctcctgtca      420 gctactcttc catctgggat tccttgtca agaacaacag cttcccaacg atcagtcttg      480
ccttgtcgac cgcaaatgaa gtcgcaacct tcaacgactc cagccaggag gtgaccttct     540
tcctgcccac tgagacggct tttgacaagt tgtcggacgc gctgggcgtt gccaggagca     600
```

```
accgtgcggg tttgttgccg tacttgccgg ttatcaaaag agccctaagc tatcacgtgc    660
taccgaccag aattagcctt cagagtgttg cgaatcaatc agtcggcggt acggagtact    720
acaacaccac gcttacgatg ggacagtcct caagcatcgg cgtgcgggtt tcgcctccct    780
cgagccccccc ggcgacatcc ccggagatat tcattctggg ggttagctca accgctaaag   840
tactgcaggc tgatgtcgcg gcaggcgcgt cgtgcattaa tgtcgtggat accgttttgc    900
agtattggta caactcagtt gatgaggtct tcgcctccat cagcggcgcc tcgaccatgt    960
accaggcgct caagaccgcc caacttctca agccagcgaa tgtgacgagc ccgtacacca   1020
tattcgtacc aaccgacgag gccttcgtca gcgccttcgg tgcctccgcc gctaccacca   1080
tcctcgccaa tctaaggtcg tacgaaagct tgctacgtca ccatgtggca tacggctggg   1140
tggttacgga cacaacctca gaagaatacg ttcgtacatc gtacataact ctgaattcga   1200
acaacgtgac ggttgtggtt ccatcgaacg acaaggccga tgctggcgtc aagcccaccg   1260
tcgcctcagc tgccgtaccc ggatcccag tcttctccat cctaaataca ttccaagtcg    1320
gcatcgagcc acaagtgatc gtccaagtga ttaatggggt tcttaacccg gctagcagtc   1380
ggcagacagc cggtggcgca gccgtgatgg tggcgccatc gccgcagctg ttgctgctgc   1440
tactgctgct gctggccggg ctcatgctga tctagatgaa gatttgttct ttaggcagtt   1500
ctagtggagc ttttttatgaa gggttttttg acttgagagt tttcgggagt ggttgggggg   1560
ggggagtcaa gttgcgtaag tagtgaggtg tgtcgttgcg tgcgcagcgt accttgggct   1620
aacctggctt ggcagccatt gcgctatttt gttcctattc gcggtggtga tgctgctgct   1680
gctattgctg atgctgatgc cccgacttgg tcggaaattg ggcgaagtgg tattgcgggg   1740
gatttgccca ttgggggggg ggcggagaga gttaagtttg gagggagcgg agtcccattg   1800
cgggctgtgt gttgacttgg tcggaactgt tgggattcat catccaccca cccacccacc   1860
cacccagcct tatcttattg ccaaaaatcc aacacgcttc cagcttattg ccatcttgcc   1920
atctaaccat ccatccatct aaccatccat ccatccatcc atctaaccat ctaaccatcc   1980
atccatccat acggcatgtt agcccttgca tgggctggct atcagcacgc ggtgcagtgc   2040
gtgtcgtgcg cgcatttgcc accaccagct gctctccagc tgactcccgc cacttcccct   2100
cgcttagaaa atttgaattt gcagcacggc gatcatctgg ggctcccccg cctggtgcgt   2160
cttcaattct atgcatgaat tgtgcgcgcg cgtgcctgcc tgcatgcctg catgcaacct   2220
tgcacatgca gggacaacct caatgcagcc ttcttgcgtt tagttgggga gaggttgtgc   2280
cgcctaaccg ataggacgtt gttcgttggt tagttgggtg atggtggttg cttggctcaa   2340
tacgtgaatg cacacggaga agcgtcacgt gctgggatga cacaagaaac acacgcacac   2400
gaacgacata tgacgacata cataccaatg actgaggacg atgcaacgca tcggtgagac   2460
tgttatcggg ttttataatt gttcgctgca ggacgcatcc ctgctctgaa gggtgcatac   2520
cgtatttttca cattacaaag gcaaaaaccc tgttcgcgcg cattttttaa aattagttgg   2580
atccgattgc ggtatggatt tacggctggg tgtacggcaa cgtcttgata gaaaattatg   2640
tcgcatttta gatttgaagg gtaagagttt ccagaggttt cataggatgg atagcacatg   2700
aaagttttag cttaggatgg tgtctaaaag atggtggttc tactgcgttg cttaagggcg   2760
aagaaagcgc atgcagcagc atttgcggca gggtggaggg tccggatatg gggtgccagc   2820
ggggatggtc gcgaggccca gcggcctttg gggccttggc tacgttagaa gcaagcatgc   2880
ctgtgcattg tacgtgcatg caatgctcgc atggggatta tctcctctgc gtgttaaatt   2940
cacgcggcgt tcgacgctcc ctatctaaat gacgaacgat gtaaattctt ttaacttcag   3000
```

```
aacagtgaaa aagaggtttt cagccattca gccatcgtac caccaccacg ggggtattga    3060
tgctggcagt gtaaatacct gaggacct                                       3088
```

<210> SEQ ID NO 20
<211> LENGTH: 463
<212> TYPE: PRT
<213> ORGANISM: Volvox carteri f. nagariensis

<400> SEQUENCE: 20

```
Met Arg Met Ala Ile Ala Ala Phe Met Asn Tyr Leu Leu Ala Cys Ala
1               5                   10                  15

Gly Leu Leu Leu Phe Leu Thr Pro Ala Trp Lys Ser Asn Val Leu Ala
            20                  25                  30

Phe Thr Tyr Pro Pro Leu Ile Ala Ser Pro Ser Ser Phe Thr Ser Pro
        35                  40                  45

Pro Leu Pro Ser Thr Pro Ser Pro Pro Pro Leu Leu Pro Ala Leu
    50                  55                  60

Ala Ser Pro Pro Pro Pro Pro Asn Glu Asp Val Asp Arg Pro Pro
65                  70                  75                  80

Leu Val Lys Asp Asn Thr Pro Thr Ser Pro Ala Ser Ser Gln Pro Ala
                85                  90                  95

Ile Pro Pro Pro Ser Pro Pro Ser Thr Pro Pro Thr Pro Pro Val
            100                 105                 110

Ser Tyr Ser Ser Ile Trp Asp Phe Leu Val Lys Asn Asn Ser Phe Pro
        115                 120                 125

Thr Ile Ser Leu Ala Leu Ser Thr Ala Asn Glu Val Ala Thr Phe Asn
130                 135                 140

Asp Ser Ser Gln Glu Val Thr Phe Phe Leu Pro Thr Glu Thr Ala Phe
145                 150                 155                 160

Asp Lys Leu Ser Asp Ala Leu Gly Val Ala Arg Ser Asn Arg Ala Gly
                165                 170                 175

Leu Leu Pro Tyr Leu Pro Val Ile Lys Arg Ala Leu Ser Tyr His Val
            180                 185                 190

Leu Pro Thr Arg Ile Ser Leu Gln Ser Val Ala Asn Gln Ser Val Gly
        195                 200                 205

Gly Thr Glu Tyr Tyr Asn Thr Thr Leu Thr Met Gly Gln Ser Ser Ser
    210                 215                 220

Ile Gly Val Arg Val Ser Pro Pro Ser Pro Pro Ala Thr Ser Pro
225                 230                 235                 240

Glu Ile Phe Ile Leu Gly Val Ser Ser Thr Ala Lys Val Leu Gln Ala
                245                 250                 255

Asp Val Ala Ala Gly Ala Ser Cys Ile Asn Val Val Asp Thr Val Leu
            260                 265                 270

Gln Tyr Trp Tyr Asn Ser Val Asp Glu Val Phe Ala Ser Ile Ser Gly
        275                 280                 285

Ala Ser Thr Met Tyr Gln Ala Leu Lys Thr Ala Gln Leu Leu Lys Pro
    290                 295                 300

Ala Asn Val Thr Ser Pro Tyr Thr Ile Phe Val Pro Thr Asp Glu Ala
305                 310                 315                 320

Phe Val Ser Ala Phe Gly Ala Ser Ala Thr Thr Ile Leu Ala Asn
                325                 330                 335

Leu Arg Ser Tyr Glu Ser Leu Leu Arg His His Val Ala Tyr Gly Trp
            340                 345                 350
```

Val Val Thr Asp Thr Thr Ser Glu Glu Tyr Val Arg Thr Ser Tyr Ile
        355                 360                 365

Thr Leu Asn Ser Asn Asn Val Thr Val Val Val Pro Ser Asn Asp Lys
    370                 375                 380

Ala Asp Ala Gly Val Lys Pro Thr Val Ala Ser Ala Ala Val Pro Gly
385                 390                 395                 400

Ser Pro Val Phe Ser Ile Leu Asn Thr Phe Gln Val Gly Ile Glu Pro
            405                 410                 415

Gln Val Ile Val Gln Val Ile Asn Gly Val Leu Asn Pro Ala Ser Ser
                420                 425                 430

Arg Gln Thr Ala Gly Gly Ala Ala Val Met Val Ala Pro Ser Pro Gln
        435                 440                 445

Leu Leu Leu Leu Leu Leu Leu Leu Leu Ala Gly Leu Met Leu Ile
    450                 455                 460

<210> SEQ ID NO 21
<211> LENGTH: 819
<212> TYPE: DNA
<213> ORGANISM: Streptomyces rimosus

<400> SEQUENCE: 21
atggacgatg cgttgcgtgc actgcggggt cggtatcccg gttgtgagtg ggttgttgtg      60
gaggatgggg cctcgggggc tggtgtttat cggcttcggg gtggtgggcg ggagttgttt     120
gtcaaggtgg cagctctggg ggccggggtg ggcttgttgg gtgaggctga gcggctggtg     180
tggttggcgg aggtggggat tcccgtacct cgtgttgtgg agggtggtgg ggacgagagg     240
gtcgcctggt tggtcaccga agcggttccg gggcgtccgg ccagtgcgcg gtggccgcgg     300
gagcagcggc tggacgtggc ggtggcgctc gcggggctcg ctcgttcgct gcacgcgctg     360
gactgggagc ggtgtccgtt cgatcgcagt ctcgcggtga cggtgccgca gcggcccgt     420 gctgtcgctg aagggagcgt cgacttggag gatctggacg aggagcggaa ggggtggtcg     480
ggggagcggc ttctcgccga gctggagcgg actcggcctg cggacgagga tctggcggtt     540
tgccacggtg acctgtgccc ggacaacgtg ctgctcgacc ctcgtacctg cgaggtgacc     600
gggctgatcg acgtggggcg ggtcggccgt gcggaccggc actccgatct cgcgctggtg     660
ctgcgcgagc tggcccacga ggaggacccg tggttcgggc cggagtgttc cgcggcgttc     720
ctgcgggagt acgggcgcgg gtgggatggg gcggtatcgg aggaaaagct ggcgttttac     780
cggctgttgg acgagttctt ctgagggacc tgatggtgt                             819

<210> SEQ ID NO 22
<211> LENGTH: 1503
<212> TYPE: DNA
<213> ORGANISM: Streptomyces rimosus

<400> SEQUENCE: 22
ggcttgacat gattggtgcg tatgtttgta tgaagctaca ggactgattt ggcgggctat      60
gagggcgcgg gaagctctgg aagggccgcg atggggcgcg cggcgtccag aaggcgccat     120
acggcccgct ggcggcaccc atccggtata aagcccgcg accccgaacg gtgacctcca      180
ctttcagcga caaacgagca cttatacata cgcgactatt ctgccgctat acataaccac     240
tcagctagct taagatccca tcaagcttgc atgccgggcg cgccagaagg agcgcagcca     300
aaccaggatg atgtttgatg gggtatttga gcacttgcaa cccttatccg gaagcccct     360 ggcccacaaa ggctaggcgc caatgcaagc agttcgcatg cagcccctgg agcggtgccc     420

```
tcctgataaa ccggccaggg ggcctatgtt ctttactttt ttacaagaga agtcactcaa        480
catcttaaaa tggccaggtg agtcgacgag caagcccggc ggatcaggca gcgtgcttgc        540
agatttgact tgcaacgccc gcattgtgtc gacgaaggct tttggctcct ctgtcgctgt        600
ctcaagcagc atctaaccct gcgtcgccgt ttccatttgc aggatggcca ctccgccctc        660
cccggtgctg aagaatttcg aagcatggac gatgcgttgc gtgcactgcg gggtcggtat        720
cccggttgtg agtgggttgt tgtggaggat ggggcctcgg gggctggtgt ttatcggctt        780
cggggtggtg ggcgggagtt gtttgtcaag gtggcagctc tgggggccgg ggtgggcttg        840
ttgggtgagg ctgagcggct ggtgtggttg gcggaggtgg ggattcccgt acctcgtgtt        900
gtggagggtg gtggggacga gagggtcgcc tggttggtca ccgaagcggt tccggggcgt        960
ccggccagtg cgcggtggcc gcgggagcag cggctgacg tggcggtggc gctcgcgggg       1020
ctcgctcgtt cgctgcacgc gctggactgg gagcggtgtc cgttcgatcg cagtctcgcg       1080
gtgacggtgc cgcaggcggc ccgtgctgtc gctgaaggga gcgtcgactt ggaggatctg       1140
gacgaggagc ggaaggggtg gtcggggag cggcttctcg ccgagctgga gcggactcgg       1200
cctgcggacg aggatctggc ggtttgccac ggtcacctgt gcccggacaa cgtgctgctc       1260
gaccctcgta cctgcgaggt gacccgggctg atcgacgtgg ggcgggtcgg ccgtgcggac       1320
cggcactccg atctcgcgct ggtgctgcgc gagctggccc acgaggagga cccgtggttc       1380
gggccggagt gttccgcggc gttcctgcgg gagtacgggc gcgggtggga tggggcggta       1440
tcggaggaaa agctggcgtt ttaccggctg ttggacgagt tcttctgagg gacctgatgg       1500
tgt                                                                    1503

<210> SEQ ID NO 23
<211> LENGTH: 4395
<212> TYPE: DNA
<213> ORGANISM: Homo sapiens

<400> SEQUENCE: 23
atgttcagct ttgtggacct ccggctcctg ctcctcttag cggccaccgc cctcctgacg         60
cacggccaag aggaaggcca agtcgagggc caagacgaag acatcccacc aatcacctgc        120
gtacagaacg gcctcaggta ccatgaccga gacgtgtgga aacccgagcc ctgccggatc        180
tgcgtctgcg acaacggcaa ggtgttgtgc gatgacgtga tctgtgacga gaccaagaac        240
tgccccggcg ccgaagtccc cgagggcgag tgctgtcccg tctgccccga cggctcagag        300
tcacccaccg accaagaaac caccggcgtc gagggaccca aggagacac tggccccga         360
ggcccaaggg gacccgcagg ccccccctggc cgagatggca tccctggaca gcctggactt        420
cccggacccc ccggaccccc cggacctccc ggacccctg gctcggagg aaactttgct        480
ccccagctgt cttatggcta tgatgagaaa tcaaccggag gaatttccgt gcctggcccc        540
atgggtccct ctggtcctcg tggtctccct ggccccctg gtgcacctgg tccccaaggc        600
ttccaaggtc cccctggtga gcctggcgag cctggagctt caggtccat gggtccccga        660
ggtccccag gtccccctgg aaagaatgga gatgatgggg aagctggaaa acctggtcgt        720
cctggtgagc gtgggcctcc tgggcctcag ggtgctcgag gattgcccgg aacagctggc        780
ctccctggaa tgaagggaca cagaggtttc agtggttttgg atggtgccaa gggagatgct        840
ggtcctgctg gtcctaaggg tgagcctggc agccctggtg aaaatggagc tcctggtcag        900
atgggccccc gtggcctgcc tggtgagaga ggtcgccctg gagccctgg ccctgctggt        960
gctcgtggaa atgatggtgc tactggtgct gccggggccc ctggtccac cggccccgct       1020
```

```
ggtcctcctg gcttccctgg tgctgttggt gctaagggtg aagctggtcc ccaagggccc    1080
cgaggctctg aaggtcccca gggtgtgcgt ggtgagcctg gccccctggg ccctgctggt    1140
gctgctggcc ctgctggaaa ccctggtgct gatggacagc ctggtgctaa aggtgccaat    1200
ggtgctcctg gtattgctgg tgctcctggc ttccctggtg cccgaggccc ctctggaccc    1260
cagggccccg gcggccctcc tggtcccaag ggtaacagcg gtgaacctgg tgctcctggc    1320
agcaaaggag acactggtgc taagggagag cctggcccct tggtgttca aggacccct    1380 ggccctgctg agaggaagg aaagcgagga gctcgaggtg aacccggacc cactggcctg    1440
cccggacccc ctggcgagcg tggtggacct ggtagccgtg gtttccctgg cgcagatggt    1500
gttgctggtc caagggtcc cgctggtgaa cgtggttctc ctggccctgc tggccccaaa    1560
ggatcctctg gtgaagctgg tcgtcccggt gaagctggtc tgcctggtgc caagggtctg    1620
actggaagcc ctggcagccc tggtcctgat ggcaaaactg gccccctgg tcccgccggt    1680 caagatggtc gccccggacc cccaggccca cctggtgccc gtggtcaggc tggtgtgatg    1740
ggattccctg gacctaaagg tgctgctgga gagcccggca aggctggaga gcgaggtgtt    1800
cccgaccccc ctggcgctgt cggtcctgct ggcaaagatg gagaggctgg agctcaggga    1860 cccctggcc ctgctggtcc cgctggcgag agaggtgaac aaggccctgc tggctccccc    1920
ggattccagg gtctccctgg tcctgctggt cctccaggtg aagcaggcaa acctggtgaa    1980
cagggtgttc ctggagacct ggcgcccct ggccctctg gagcaagagg cgagagaggt    2040
ttccctggcg agcgtggtgt gcaaggtccc cctggtcctg ctggtccccg agggggccaac    2100 ggtgctcccg gcaacgatgg tgctaagggt gatgctggtg ccctggagc tcccggtagc    2160 cagggcgccc ctggccttca gggaatgcct ggtgaacgtg gtgcagctgg tcttccaggg    2220
cctaagggtg acagaggtga tgctggtccc aaaggtgctg atggctctcc tggcaaagat    2280
ggcgtccgtg gtctgactgg ccccattggt cctcctggcc ctgctggtgc ccctggtgac    2340
aagggtgaaa gtggtcccag cggccctgct ggtcccactg gagctcgtgg tgcccccgga    2400
gaccgtggtg agcctggtcc cccggcccct gctggctttg ctggcccccc tggtgctgac    2460
ggccaacctg gtgctaaagg cgaacctggt gatgctggtg ctaaaggcga tgctggtccc    2520
cctggccctg ccggacccgc tggacccct ggccccattg gtaatgttgg tgctcctgga    2580
gccaaaggtg ctcgcggcag cgctggtccc cctggtgcta ctggtttccc tggtgctgct    2640
ggccgagtcg gtcctcctgg cccctctgga aatgctggac cccctggccc tcctggtcct    2700
gctggcaaag aaggcggcaa aggtccccgt ggtgagactg gccctgctgg acgtcctggt    2760
gaagttggtc ccctggtcc cctggccct gctggcgaga aggatccccc tggtgctgat    2820
ggtcctgctg gtgctcctgg tactcccggg cctcaaggta ttgctggaca gcgtggtgtg    2880
gtcggcctgc ctggtcagag aggagagaga ggcttccctg gtcttcctgg ccctctggt    2940 gaacctggca acaaggtccc ctctggagca agtggtgaac gtggtcccc tggtcccatg    3000 ggccccctg gattggctgg accccctggt gaatctggac gtgagggggc tcctggtgcc    3060
gaaggttccc ctggacgaga cggttctcct ggcgccaagg gtgaccgtgg tgagaccggc    3120
cccgctggac ccctggtgc tcctggtgct cctggtgccc ctggcccgt tggccctgct    3180 ggcaagagtg gtgatcgtgg tgagactggt cctgctggtc ccgccggtcc tgtcggccct    3240
gttggcgccc gtggccccgc cggacccaa ggccccgtg gtgacaaggg tgagacaggc    3300
gaacagggcg acagaggcat aaagggtcac cgtggcttct ctggcctcca gggtcccct    3360
```

-continued

```
ggccctcctg gctctcctgg tgaacaaggt ccctctggag cctctggtcc tgctggtccc    3420
cgaggtcccc ctggctctgc tggtgctcct ggcaaagatg gactcaacgg tctccctggc    3480
cccattgggc ccctggtcc tcgcggtcgc actggtgatg ctggtcctgt tggtcccccc    3540
ggccctcctg gacctcctgg tccccctggt cctcccagcg ctggtttcga cttcagcttc    3600
ctgccccagc cacctcaaga aaggctcac gatggtggcc gctactaccg ggctgatgat    3660
gccaatgtgg ttcgtgaccg tgacctcgag gtggacacca ccctcaagag cctgagccag    3720
cagatcgaga acatccggag cccagagggc agccgcaaga accccgcccg cacctgccgt    3780
gacctcaaga tgtgccactc tgactggaag agtggagagt actggattga ccccaaccaa    3840
ggctgcaacc tggatgccat caaagtcttc tgcaacatgg agactggtga cctgcgtg     3900
taccccactc agcccagtgt ggcccagaag aactggtaca tcagcaagaa ccccaaggac    3960
aagaggcatg tctggttcgg cgagagcatg accgatggat ccagttcga gtatggcggc    4020
cagggctccg accctgccga tgtggccatc cagctgacct tcctgcgcct gatgtccacc    4080
gaggcctccc agaacatcac ctaccactgc aagaacagcg tggcctacat ggaccagcag    4140
actggcaacc tcaagaaggc cctgctcctc cagggctcca acgagatcga gatccgcgcc    4200
gagggcaaca gccgcttcac ctacagcgtc actgtcgatg gctgcacgag tcacaccgga    4260
gcctggggca agacagtgat tgaatacaaa accaccaaga cctcccgcct gcccatcatc    4320
gatgtggccc ccttggacgt tggtgccca gaccaggaat tcggcttcga cgttggccct    4380
gtctgcttcc tgtaa                                                    4395
```

<210> SEQ ID NO 24
<211> LENGTH: 1468
<212> TYPE: PRT
<213> ORGANISM: Homo sapiens

<400> SEQUENCE: 24

```
Met Phe Ser Phe Val Asp Leu Arg Leu Leu Leu Leu Ala Ala Thr
1               5                   10                  15

Ala Leu Leu Thr His Gly Gln Glu Glu Gly Gln Val Glu Gly Gln Asp
                20                  25                  30

Glu Asp Ile Pro Pro Ile Thr Cys Val Gln Asn Gly Leu Arg Tyr His
                35                  40                  45

Asp Arg Asp Val Trp Lys Pro Glu Pro Cys Arg Ile Cys Val Cys Asp
50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
                115                 120                 125

Pro Gly Arg Asp Gly Ile Pro Gly Gln Pro Gly Leu Pro Gly Pro Pro
                130                 135                 140

Gly Pro Pro Gly Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
                180                 185                 190
```

```
Pro Gly Ala Pro Gly Pro Gln Gly Phe Gln Gly Pro Pro Gly Glu Pro
        195                 200                 205
Gly Glu Pro Gly Ala Ser Gly Pro Met Gly Pro Arg Gly Pro Pro Gly
        210                 215                 220
Pro Pro Gly Lys Asn Gly Asp Asp Gly Glu Ala Gly Lys Pro Gly Arg
225                 230                 235                 240
Pro Gly Glu Arg Gly Pro Pro Gly Pro Gln Gly Ala Arg Gly Leu Pro
                245                 250                 255
Gly Thr Ala Gly Leu Pro Gly Met Lys Gly His Arg Gly Phe Ser Gly
            260                 265                 270
Leu Asp Gly Ala Lys Gly Asp Ala Gly Pro Ala Gly Pro Lys Gly Glu
        275                 280                 285
Pro Gly Ser Pro Gly Glu Asn Gly Ala Pro Gly Gln Met Gly Pro Arg
        290                 295                 300
Gly Leu Pro Gly Glu Arg Gly Arg Pro Gly Ala Pro Gly Pro Ala Gly
305                 310                 315                 320
Ala Arg Gly Asn Asp Gly Ala Thr Gly Ala Ala Gly Pro Pro Gly Pro
                325                 330                 335
Thr Gly Pro Ala Gly Pro Pro Gly Phe Pro Gly Ala Val Gly Ala Lys
            340                 345                 350
Gly Glu Ala Gly Pro Gln Gly Pro Arg Gly Ser Glu Gly Pro Gln Gly
        355                 360                 365
Val Arg Gly Glu Pro Gly Pro Pro Gly Pro Ala Gly Ala Ala Gly Pro
        370                 375                 380
Ala Gly Asn Pro Gly Ala Asp Gly Gln Pro Gly Ala Lys Gly Ala Asn
385                 390                 395                 400
Gly Ala Pro Gly Ile Ala Gly Ala Pro Gly Phe Pro Gly Ala Arg Gly
                405                 410                 415
Pro Ser Gly Pro Gln Gly Pro Gly Gly Pro Pro Gly Pro Lys Gly Asn
            420                 425                 430
Ser Gly Glu Pro Gly Ala Pro Gly Ser Lys Gly Asp Thr Gly Ala Lys
        435                 440                 445
Gly Glu Pro Gly Pro Val Gly Val Gln Gly Pro Pro Gly Pro Ala Gly
        450                 455                 460
Glu Glu Gly Lys Arg Gly Ala Arg Gly Glu Pro Gly Pro Thr Gly Leu
465                 470                 475                 480
Pro Gly Pro Pro Gly Glu Arg Gly Gly Pro Gly Ser Arg Gly Phe Pro
                485                 490                 495
Gly Ala Asp Gly Val Ala Gly Pro Lys Gly Pro Ala Gly Glu Arg Gly
            500                 505                 510
Ser Pro Gly Pro Ala Gly Pro Lys Gly Ser Pro Gly Glu Ala Gly Arg
        515                 520                 525
Pro Gly Glu Ala Gly Leu Pro Gly Ala Lys Gly Leu Thr Gly Ser Pro
        530                 535                 540
Gly Ser Pro Gly Pro Asp Gly Lys Thr Gly Pro Pro Gly Pro Ala Gly
545                 550                 555                 560
Gln Asp Gly Arg Pro Gly Pro Pro Gly Pro Pro Gly Ala Arg Gly Gln
                565                 570                 575
Ala Gly Val Met Gly Phe Pro Gly Pro Lys Gly Ala Ala Gly Glu Pro
            580                 585                 590
Gly Lys Ala Gly Glu Arg Gly Val Pro Gly Pro Pro Gly Ala Val Gly
        595                 600                 605
```

-continued

```
Pro Ala Gly Lys Asp Gly Glu Ala Gly Ala Gln Gly Pro Pro Gly Pro
    610                 615                 620
Ala Gly Pro Ala Gly Glu Arg Gly Glu Gln Gly Pro Ala Gly Ser Pro
625                 630                 635                 640
Gly Phe Gln Gly Leu Pro Gly Pro Ala Gly Pro Pro Gly Glu Ala Gly
                645                 650                 655
Lys Pro Gly Glu Gln Gly Val Pro Gly Asp Leu Gly Ala Pro Gly Pro
            660                 665                 670
Ser Gly Ala Arg Gly Glu Arg Gly Phe Pro Gly Glu Arg Gly Val Gln
                675                 680                 685
Gly Pro Pro Gly Pro Ala Gly Pro Arg Gly Ala Asn Gly Ala Pro Gly
690                 695                 700
Asn Asp Gly Ala Lys Gly Asp Ala Gly Ala Pro Gly Ala Pro Gly Ser
705                 710                 715                 720
Gln Gly Ala Pro Gly Leu Gln Gly Met Pro Gly Glu Arg Gly Ala Ala
                725                 730                 735
Gly Leu Pro Gly Pro Lys Gly Asp Arg Gly Asp Ala Gly Pro Lys Gly
            740                 745                 750
Ala Asp Gly Ser Pro Gly Lys Asp Gly Val Arg Gly Leu Thr Gly Pro
            755                 760                 765
Ile Gly Pro Pro Gly Pro Ala Gly Ala Pro Gly Asp Lys Gly Glu Ser
        770                 775                 780
Gly Pro Ser Gly Pro Ala Gly Pro Thr Gly Ala Arg Gly Ala Pro Gly
785                 790                 795                 800
Asp Arg Gly Glu Pro Gly Pro Pro Gly Pro Ala Gly Phe Ala Gly Pro
                805                 810                 815
Pro Gly Ala Asp Gly Gln Pro Gly Ala Lys Gly Glu Pro Gly Asp Ala
            820                 825                 830
Gly Ala Lys Gly Asp Ala Gly Pro Pro Gly Pro Ala Gly Pro Ala Gly
            835                 840                 845
Pro Pro Gly Pro Ile Gly Asn Val Gly Ala Pro Gly Ala Lys Gly Ala
    850                 855                 860
Arg Gly Ser Ala Gly Pro Pro Gly Ala Thr Gly Phe Pro Gly Ala Ala
865                 870                 875                 880
Gly Arg Val Gly Pro Pro Gly Pro Ser Gly Asn Ala Gly Pro Pro Gly
                885                 890                 895
Pro Pro Gly Pro Ala Gly Lys Glu Gly Gly Lys Gly Pro Arg Gly Glu
        900                 905                 910
Thr Gly Pro Ala Gly Arg Pro Gly Glu Val Gly Pro Pro Gly Pro Pro
            915                 920                 925
Gly Pro Ala Gly Glu Lys Gly Ser Pro Gly Ala Asp Gly Pro Ala Gly
    930                 935                 940
Ala Pro Gly Thr Pro Gly Pro Gln Gly Ile Ala Gly Gln Arg Gly Val
945                 950                 955                 960
Val Gly Leu Pro Gly Gln Arg Gly Glu Arg Gly Phe Pro Gly Leu Pro
                965                 970                 975
Gly Pro Ser Gly Glu Pro Gly Lys Gln Gly Pro Ser Gly Ala Ser Gly
            980                 985                 990
Glu Arg Gly Pro Pro Gly Pro Met  Gly Pro Pro Gly Leu  Ala Gly Pro
            995                 1000                1005
Pro Gly  Glu Ser Gly Arg Glu  Gly Ala Pro Gly Ala  Glu Gly Ser
        1010                1015                1020
Pro Gly  Arg Asp Gly Ser Pro  Gly Ala Lys Gly Asp  Arg Gly Glu
```

-continued

```
                1025                1030                1035

Thr Gly Pro Ala Gly Pro Pro Gly Ala Pro Gly Ala
    1040                1045                1050

Pro Gly Pro Val Gly Pro Ala Gly Lys Ser Gly Asp Arg Gly Glu
    1055                1060                1065

Thr Gly Pro Ala Gly Pro Ala Gly Pro Val Gly Pro Val Gly Ala
    1070                1075                1080

Arg Gly Pro Ala Gly Pro Gln Gly Pro Arg Gly Asp Lys Gly Glu
    1085                1090                1095

Thr Gly Glu Gln Gly Asp Arg Gly Ile Lys Gly His Arg Gly Phe
    1100                1105                1110

Ser Gly Leu Gln Gly Pro Pro Gly Pro Pro Gly Ser Pro Gly Glu
    1115                1120                1125

Gln Gly Pro Ser Gly Ala Ser Gly Pro Ala Gly Pro Arg Gly Pro
    1130                1135                1140

Pro Gly Ser Ala Gly Ala Pro Gly Lys Asp Gly Leu Asn Gly Leu
    1145                1150                1155

Pro Gly Pro Ile Gly Pro Pro Gly Pro Arg Gly Arg Thr Gly Asp
    1160                1165                1170

Ala Gly Pro Val Gly Pro Pro Gly Pro Pro Gly Pro Pro Gly Pro
    1175                1180                1185

Pro Gly Pro Pro Ser Ala Gly Phe Asp Phe Ser Phe Leu Pro Gln
    1190                1195                1200

Pro Pro Gln Glu Lys Ala His Asp Gly Gly Arg Tyr Tyr Arg Ala
    1205                1210                1215

Asp Asp Ala Asn Val Val Arg Asp Arg Asp Leu Glu Val Asp Thr
    1220                1225                1230

Thr Leu Lys Ser Leu Ser Gln Gln Ile Glu Asn Ile Arg Ser Pro
    1235                1240                1245

Glu Gly Ser Arg Lys Asn Pro Ala Arg Thr Cys Arg Asp Leu Lys
    1250                1255                1260

Met Cys His Ser Asp Trp Lys Ser Gly Glu Tyr Trp Ile Asp Pro
    1265                1270                1275

Asn Gln Gly Cys Asn Leu Asp Ala Ile Lys Val Phe Cys Asn Met
    1280                1285                1290

Glu Thr Gly Glu Thr Cys Val Tyr Pro Thr Gln Pro Ser Val Ala
    1295                1300                1305

Gln Lys Asn Trp Tyr Ile Ser Lys Asn Pro Lys Asp Lys Arg His
    1310                1315                1320

Val Trp Phe Gly Glu Ser Met Thr Asp Gly Phe Gln Phe Glu Tyr
    1325                1330                1335

Gly Gly Gln Gly Ser Asp Pro Ala Asp Val Ala Ile Gln Leu Thr
    1340                1345                1350

Phe Leu Arg Leu Met Ser Thr Glu Ala Ser Gln Asn Ile Thr Tyr
    1355                1360                1365

His Cys Lys Asn Ser Val Ala Tyr Met Asp Gln Gln Thr Gly Asn
    1370                1375                1380

Leu Lys Lys Ala Leu Leu Leu Gln Gly Ser Asn Glu Ile Glu Ile
    1385                1390                1395

Arg Ala Glu Gly Asn Ser Arg Phe Thr Tyr Ser Val Thr Val Asp
    1400                1405                1410

Gly Cys Thr Ser His Thr Gly Ala Trp Gly Lys Thr Val Ile Glu
    1415                1420                1425
```

```
Tyr Lys Thr Thr Lys Thr Ser Arg Leu Pro Ile Ile Asp Val Ala
    1430                1435                1440

Pro Leu Asp Val Gly Ala Pro Asp Gln Glu Phe Gly Phe Asp Val
    1445                1450                1455

Gly Pro Val Cys Phe Leu Thr Ala Gln Asp
    1460                1465

<210> SEQ ID NO 25
<211> LENGTH: 1146
<212> TYPE: PRT
<213> ORGANISM: Drosophila melanogaster

<400> SEQUENCE: 25

Met Leu Glu Leu Pro Phe Thr Thr Ile Arg Pro Asn Cys Arg Leu Arg
1               5                   10                  15

Gln Asn Leu Gly Ile Leu Ile Ile Leu Gln Cys Val Leu Thr Cys Tyr
            20                  25                  30

Asn Phe Asn Leu Glu Gln Arg Leu Pro Ile Val Lys Tyr Gly His Pro
        35                  40                  45

His Ser His Phe Gly Tyr Ser Val Ala Thr His Thr Ile Gly Glu Ala
    50                  55                  60

Asn Gly Pro Asn Lys Thr Asn Cys Val Leu Val Gly Ala Pro Leu Asp
65                  70                  75                  80

Gln Asn Arg Gln Pro Asn Thr Thr His Ser Gly Ala Leu Trp Arg Cys
                85                  90                  95

Pro Met Thr Gln Arg Phe Asp Asp Cys Glu Gln Val Ile Thr Asp Gly
            100                 105                 110

Arg Arg Asn Phe Asp Ser Glu Ile Leu Ser Pro Pro Gly Asn Asp Glu
        115                 120                 125

Ile Lys Glu Asp Gln Trp Met Gly Val Thr Val Arg Ser Asn Pro Leu
    130                 135                 140

Gln Ala Asn Gly Ser Gly Gly Lys Val Ile Val Cys Ala His Arg Tyr
145                 150                 155                 160

Met Tyr Ile Val Arg Glu Asn Arg Tyr Gly Gln Gly Leu Cys Tyr Leu
                165                 170                 175

Leu Thr Asn Asp Leu Gln Phe Glu Glu Val His Glu Pro Cys Lys Gly
            180                 185                 190

Arg Pro Val Gln Arg Gln His Glu Asp Tyr Gly Leu Cys Gln Ala Gly
        195                 200                 205

Thr Ser Ala Ala Leu Leu Asp Asp Asp Thr Met Val Leu Gly Ser Pro
    210                 215                 220

Gly Pro Tyr Thr Trp Arg Gly Ser Ile Trp Val Thr Gln Val Gly Gly
225                 230                 235                 240

Glu Tyr Leu Gln Arg Asp Lys Thr Thr Tyr Tyr Ser Asp His Ser Asp
                245                 250                 255

Leu Asn Ser Pro Val Asp Lys Tyr Ser Tyr Leu Gly Met Ser Val Thr
            260                 265                 270

Gly Gly Arg Phe Phe Gly His Met Ser Tyr Ala Ala Gly Ala Pro Arg
        275                 280                 285

Ser Glu Gly His Gly Gln Val Val Ile Phe Asp Lys Ser Thr Asp Asn
    290                 295                 300

Pro Ile Pro Val His Ser Ile Leu Asp Gly Glu Gln Phe Gly Ser Ser
305                 310                 315                 320

Phe Gly Tyr Glu Leu Ala Thr Ala Asp Ile Asn Gly Asp His Arg Pro
```

-continued

```
                        325                 330                 335
Asp Leu Ile Val Ala Ala Pro Leu Tyr Phe Thr Lys Thr Glu Gly Gly
                    340                 345                 350
Ala Val Tyr Val Tyr Gln Asn Ile Gln Asp Thr Leu Pro Met Lys Tyr
                355                 360                 365
Thr Leu Lys Leu Thr Gly Pro Leu Glu Ser Arg Phe Gly Leu Ala Leu
            370                 375                 380
Ala Asn Ile Gly Asp Leu Asn Lys Asp Asn Cys Glu Asp Leu Ala Val
385                 390                 395                 400
Gly Ala Pro Tyr Glu Gly Asn Gly Val Val Tyr Ile Tyr Leu Gly Ser
                405                 410                 415
Ser Gln Gly Leu Asn Ser Lys Pro Ala Gln Lys Ile Gln Ala Ser Glu
            420                 425                 430
Leu Gly Gly Thr Ile Pro Asn Gly Gln Pro Ile Arg Thr Phe Gly Ile
        435                 440                 445
Ser Ile Ser Gly Asn Thr Asp Leu Asp Asp Asn Ser Tyr Pro Asp Val
    450                 455                 460
Val Ile Gly Ala Phe Asn Ser Ser Ala Ala Val Ile Leu Leu Ala Arg
465                 470                 475                 480
Pro Ile Ile Ser Ile Gln Thr Ser Val Gln Arg Lys Glu Leu His Asn
                485                 490                 495
Met Asp Pro Asn Thr Pro Gly Cys Leu Asp Asp Pro Ala Ser Asn Leu
            500                 505                 510
Thr Cys Phe Thr Phe Arg Ala Cys Cys Ser Ile Glu Pro Tyr Asp Glu
        515                 520                 525
Lys Asn Lys Glu Leu Arg Leu Ala Tyr Ser Val Glu Ala Glu Thr Phe
    530                 535                 540
Asp His Leu Lys Lys Phe Ser Arg Val Phe Phe Asp Arg Glu Asn
545                 550                 555                 560
Lys Arg Thr Asn Val Leu Ser Arg Val Val Arg Val His Thr Asn Gly
                565                 570                 575
Arg Thr Glu Cys Gln Ala Val Thr Gly Tyr Ile Lys Ala Asn Thr Arg
            580                 585                 590
Asp Ile Gln Thr Pro Val Arg Phe Arg Leu Lys Tyr Ser Leu Val Glu
        595                 600                 605
Pro Pro Leu Ala Asp Ser Ala Leu Val Arg Leu Asn Pro Ile Leu Asp
    610                 615                 620
Gln Thr Gln Ala His Val Asp Phe Glu Gly Thr Phe Gln Lys Asp Cys
625                 630                 635                 640
Gly Asp Asp Asp Leu Cys Glu Ser Asn Leu Ile Ile Arg Val Glu Pro
                645                 650                 655
Asn Ile Thr Glu Ser Ser Gly Asn Glu Tyr Thr Leu Ile Leu Asp Glu
            660                 665                 670
Thr Glu Leu Glu Val Arg Ile Asn Val Ser Asn Leu Ala Asp Ser Ala
        675                 680                 685
Tyr Glu Ala Gln Leu Phe Ile Ala His Gln Ala Gly Val Ser Tyr Val
    690                 695                 700
Ala Thr Lys Lys Pro Thr Asn Ala Thr Cys Asn Ser Tyr Asn Thr Thr
705                 710                 715                 720
Leu Val Ala Cys Ser Leu Gly Asn Pro Ile Val Arg Asp Thr Thr Thr
                725                 730                 735
Phe Val Thr Ile Arg Phe Gln Pro Lys Gly Leu Glu Pro Ser Glu Lys
            740                 745                 750
```

-continued

```
Ile Met Leu Phe His Ile Phe Ala Asn Thr Thr Ser Lys Leu Val Gly
        755                 760                 765

Pro Glu Arg Pro Glu Arg Asp Leu Arg Val Asn Val Val Arg Arg Ala
770                 775                 780

Lys Leu Asn Phe Arg Gly Trp Ala Ile Pro Glu Gln Ser Phe Tyr Ser
785                 790                 795                 800

Gly Ser Ser Val Ala Asn Ser Val Ala Asn Thr Ala Ala Thr Glu Ile
                805                 810                 815

Glu Gly His Gly Pro Met Gly Met Asp Asp Val Gly Ser Gln Val His
            820                 825                 830

His Met Phe Thr Ile Phe Asn Glu Gly Pro Ser Thr Ala Pro Lys Val
        835                 840                 845

Gln Met Val Ile His Trp Pro Tyr Ser Leu Tyr Ser Asp Pro Gln Ser
    850                 855                 860

Gly Arg Pro Val Gln Tyr Leu Leu Tyr Leu Glu Gln Val Pro Thr Val
865                 870                 875                 880

Glu Val Ser Gln Gly Glu Cys His Val Ala Lys Glu Tyr Val Asn Pro
                885                 890                 895

Leu Asn Leu Ala Ser Gly Ser Arg Glu Asn Pro Ala Tyr Leu Ser Ala
            900                 905                 910

Pro Ala Gln Met Arg Met Phe Pro Ser Gln Ser Arg His Ser Phe Asn
        915                 920                 925

Lys Ser Leu Ile His Ser Gln Arg Ser Tyr Tyr Ser Ser His Arg
    930                 935                 940

Asp Asp His Ser Asp Asp Thr Gln Ser Asn Arg Asn Arg Val Arg Arg
945                 950                 955                 960

Ser Phe Leu Glu Arg Val Thr Arg Leu Glu Arg Leu Met Tyr Asp Pro
                965                 970                 975

Glu Ser Ser Asn Ala Ala Asn Gly Lys Lys Gln Asp Ile Val Glu Leu
            980                 985                 990

Asp Cys Asn Lys Gly Ala Thr Asn  Cys Val Arg Ile Glu  Cys Asp Ile
        995                 1000                1005

Leu Asn  Met Pro Ala Leu Ser  Glu Ala Gln Val Val  Val Lys Ala
    1010                1015                1020

Arg Leu  Trp Asn Ser Thr Leu  Val Ser Glu Tyr Pro  Arg Val Glu
    1025                1030                1035

Arg Val  Arg Ile Phe Ser Thr  Ala Thr Ala Gln Ile  Pro Glu Ser
    1040                1045                1050

Tyr Gly  Val Glu Val Met Asp  His Asn Asn Ile Glu  Val Glu Thr
    1055                1060                1065

Arg Ala  Tyr Pro Glu Leu Arg  Asn Gln Gln Arg Asp  Thr Ser Ile
    1070                1075                1080

Pro Trp  Leu Ile Ile Ile Leu  Gly Ile Val Gly Gly  Leu Leu Leu
    1085                1090                1095

Leu Ala  Leu Val Thr Tyr Val  Leu Trp Lys Val Gly  Phe Phe Lys
    1100                1105                1110

Arg Ile  Arg Pro Thr Asp Pro  Thr Leu Ser Gly Asn  Leu Glu Lys
    1115                1120                1125

Met Asn  Glu Glu Lys Pro Phe  Leu Ala Pro Ser Lys  Asn Thr His
    1130                1135                1140

His Val  Phe
    1145
```

<210> SEQ ID NO 26
<211> LENGTH: 3441
<212> TYPE: DNA
<213> ORGANISM: Drosophila melanogaster

<400> SEQUENCE: 26

| | | | | | |
|---|---|---|---|---|---|
| atgttggagc | taccgtttac | caccatacgg | cccaactgcc | ggctaagaca | gaatcttggt | 60 |
| attctgataa | tcctgcaatg | cgttctcact | tgctacaact | tcaacctaga | acagcgattg | 120 |
| cccattgtga | agtacggaca | tccgcattcg | catttcggct | actcggtggc | cacccacact | 180 |
| attggcgagg | ccaatgggcc | caacaagacc | aactgtgttt | tagtgggagc | tccattggat | 240 |
| caaaatcgac | agccgaacac | cacacactct | ggcgccctct | ggcggtgtcc | aatgacacag | 300 |
| cgtttcgatg | actgcgaaca | agtgatcacc | gatggcaggc | gaaacttcga | cagcgaaatc | 360 |
| cttcaccgc | ccggcaatga | cgaaatcaag | gaggatcaat | ggatgggcgt | tacggtgcgt | 420 |
| tcgaatcccc | tacaggccaa | cggatccggc | ggaaaggtaa | tcgtctgcgc | ccatcgctat | 480 |
| atgtacatcg | tccgagagaa | tcgttatgga | cagggtctct | gctatctcct | aacgaacgat | 540 |
| ctgcaattcg | aagaggtcca | cgagccctgc | aaaggacgac | ctgtgcaaag | gcaacacgaa | 600 |
| gattatggac | tgtgccaggc | gggcacatcg | gctgccctac | tggacgatga | caccatggtg | 660 |
| ttgggttccc | ctggaccgta | cacatggcgc | ggatccattt | gggtgactca | ggtgggcggg | 720 |
| gagtacctgc | agcgcgacaa | gacgacctac | tacagtgatc | attcggactt | gaattcgccg | 780 |
| gtggacaagt | acagctatct | tggtatgtcg | gtgaccggtg | gcagattctt | tggtcacatg | 840 |
| tcatatgcgc | ctggagctcc | acgatccgag | ggtcatggac | aggtggtgat | tttcgacaag | 900 |
| tccaccgata | atccaatacc | ggtgcactcg | atcctggatg | gtgagcaatt | cggttcgagt | 960 |
| tttggctatg | aactggcaac | cgccgatata | acggagatc | acaggccgga | tttaatagtg | 1020 |
| gcagctcctt | tgtacttcac | aaaaacggaa | ggtggagctg | tgtatgtgta | ccagaatatc | 1080 |
| caggatacgt | tgcccatgaa | gtacacactc | aagttgacgg | gacctctgga | gagtcgtttc | 1140 |
| ggtctggcgt | tggccaatat | cggagatctg | aacaaggata | actgcgagga | tctggccgtg | 1200 |
| ggagcaccat | acgagggcaa | cggcgtagtc | tacatctact | tgggctcgag | tcagggcctg | 1260 |
| aattccaagc | ccgcccagaa | gatccaggcc | tcggaactgg | gtggaaccat | acccaatggt | 1320 |
| caaccgattc | gtacctttgg | catctctata | tccggcaaca | cggacttgga | tgataactcc | 1380 |
| tatccggatg | tggtaatcgg | agcattcaac | tcctcggcag | ccgtaatcct | gctggccaga | 1440 |
| cctatcatca | gcattcagac | gagtgtacag | cgcaaggagc | tgcataacat | ggatcccaat | 1500 |
| acgcccggct | gtttggacga | tccggccagt | aatctaacat | gtttcacgtt | cagagcatgt | 1560 |
| tgcagcattg | aaccgtacga | tgagaagaac | aaggaactcc | ggttggctta | tagcgtcgaa | 1620 |
| gcggaaacct | tcgatcacct | aaagaaattc | tctcgcgtct | tcttcttcga | tcgggaaaat | 1680 |
| aagcggacga | atgtgctcag | tcgcgtggtg | agagtgcata | cgaatggaag | gacagaatgc | 1740 |
| caggcagtca | cgggctacat | caaggccaat | acccgggata | tccagactcc | cgtgcgtttc | 1800 |
| cgcttgaagt | actcgctggt | ggaaccccca | ttggcggatt | ctgctttggt | acgcctcaat | 1860 |
| ccgatattgg | atcagaccca | ggcgcatgtc | gatttcgagg | gcaccttcca | gaaagactgt | 1920 |
| ggcgatgacg | atctctgtga | gagcaatctg | attatccggg | tggagccgaa | catcactgag | 1980 |
| tcctcaggca | acgaatacac | actgattctg | gatgaaacgg | aactggaggt | ccgcatcaat | 2040 |
| gttagcaatc | tggcggattc | tgcttacgaa | gctcaactat | tcatcgccca | tcaggcgggt | 2100 |
| gtttcatatg | tggcaaccaa | gaagccgacg | aatgccacgt | gcaatagcta | caataccacc | 2160 |

-continued

```
ctggttgcct gcagtcttgg taatcccatc gtgcgcgaca ccaccacatt tgtgaccatc    2220
cgattccagc ccaaaggatt ggagccaagt gagaagatca tgctattcca catattcgca    2280
aataccacct ccaagctggt gggacccgaa cgtcccgagc gggatcttcg cgtgaatgtg    2340
gtgcgtcggg cgaagctcaa cttccgaggt tgggccatac ccgagcagag tttctacagt    2400
ggatcgagtg tggctaattc ggttgcaaat actgccgcca ccgagataga aggacatggt    2460
ccgatgggta tggacgatgt gggctcccaa gttcatcaca tgttcaccat tttcaatgag    2520
ggaccatcca cggcgccgaa ggtacaaatg gtcatccatt ggccatactc actgtacagt    2580
gatccacaga gcggtcgacc ggttcagtat ctactctatc tggagcaagt acccactgtg    2640
gaagttagcc agggcgaatg ccatgtggcc aaagaatatg tcaatccgct gaatttggcc    2700
agcggttcta gggaaaatcc agcctacttg agtgctcccg cccagatgag aatgttcccc    2760
tcgcagtcgc gtcattcgtt caacaagagc ttgatccact cgcagagaag ctactactcc    2820
agcagccacc gggatgatca ttcggatgac actcaatcga accgcaatcg tgtccgtcgc    2880
agtttcctag aacgggtgac gcgcctggag aggttaatgt acgatcccga gagtagcaat    2940
gcggcgaatg caagaagca ggacatcgtc gagctggact gcaataaggg cgcgaccaac    3000
tgcgtgcgca tcgagtgtga catcctaaac atgcccgctt tgtccgaggc ccaggtggtg    3060
gtcaaggcgc gcctgtggaa ctcgacgctg gtcagtgagt atcctcgggt ggaaagggtc    3120
aggattttct cgacagccac ggctcaaata cccgagagct atggcgtcga ggtgatggat    3180
cacaataaca tagaggtgga gacgcgggcc tatccggagt taaggaacca acagcgcgac    3240
acatcgatac cgtggctgat tatcatcctg ggcatcgttg gtggcctgct cctccttgcg    3300
ctggtcacct atgtgctgtg gaaggtaggc ttctttaagc gcatccgacc caccgatccg    3360
acgttaagcg gcaatctgga gaaaatgaac gaggagaagc ccttcctggc gccatcaaag    3420
aatacgcatc acgttttcta a                                              3441
```

<210> SEQ ID NO 27
<211> LENGTH: 827
<212> TYPE: PRT
<213> ORGANISM: Homo sapiens

<400> SEQUENCE: 27

```
Asn Phe Glu Asp Cys Thr Gly Arg Gln Arg Thr Ala Tyr Phe Ser Leu
1               5                   10                  15

Asp Thr Arg Phe Lys Val Gly Thr Asp Gly Val Ile Thr Val Lys Arg
            20                  25                  30

Pro Leu Arg Phe His Asn Pro Gln Ile His Phe Leu Val Tyr Ala Trp
        35                  40                  45

Asp Ser Thr Tyr Arg Lys Phe Ser Thr Lys Val Thr Leu Asn Thr Val
    50                  55                  60

Gly His His Arg Pro Pro His Gln Ala Ser Val Ser Gly Ile
65                  70                  75                  80

Gln Ala Glu Leu Leu Thr Phe Pro Asn Ser Ser Pro Gly Leu Arg Arg
                85                  90                  95

Gln Lys Arg Asp Trp Val Ile Pro Pro Ile Ser Cys Pro Glu Asn Glu
            100                 105                 110

Lys Gly Pro Phe Pro Lys Asn Leu Val Gln Ile Lys Ser Asn Lys Asp
        115                 120                 125

Lys Glu Gly Lys Val Phe Tyr Ser Ile Thr Gly Gln Gly Ala Asp Thr
    130                 135                 140
```

```
Pro Pro Val Gly Val Phe Ile Ile Glu Arg Glu Thr Gly Trp Leu Lys
145                 150                 155                 160

Val Thr Glu Pro Leu Asp Arg Glu Arg Ile Ala Thr Tyr Thr Leu Phe
                165                 170                 175

Ser His Ala Val Ser Ser Asn Gly Asn Ala Val Glu Asp Pro Met Glu
            180                 185                 190

Ile Leu Ile Thr Val Thr Asp Gln Asn Asp Asn Lys Pro Glu Phe Thr
            195                 200                 205

Gln Glu Val Phe Lys Gly Ser Val Met Glu Gly Ala Leu Pro Gly Thr
        210                 215                 220

Ser Val Met Glu Val Thr Ala Thr Asp Ala Asp Asp Val Asn Thr
225                 230                 235                 240

Tyr Asn Ala Ala Ile Ala Tyr Thr Ile Leu Ser Gln Asp Pro Glu Leu
                245                 250                 255

Pro Asp Lys Asn Met Phe Thr Ile Asn Arg Asn Thr Gly Val Ile Ser
            260                 265                 270

Val Val Thr Thr Gly Leu Asp Arg Glu Ser Phe Pro Thr Tyr Thr Leu
        275                 280                 285

Val Val Gln Ala Ala Asp Leu Gln Gly Glu Gly Leu Ser Thr Thr Ala
        290                 295                 300

Thr Ala Val Ile Thr Val Thr Asp Thr Asn Asp Asn Pro Pro Ile Phe
305                 310                 315                 320

Asn Pro Thr Thr Tyr Lys Gly Gln Val Pro Glu Asn Glu Ala Asn Val
                325                 330                 335

Val Ile Thr Thr Leu Lys Val Thr Asp Ala Asp Ala Pro Asn Thr Pro
            340                 345                 350

Ala Trp Glu Ala Val Tyr Thr Ile Leu Asn Asp Asp Gly Gly Gln Phe
            355                 360                 365

Val Val Thr Thr Asn Pro Val Asn Asn Asp Gly Ile Leu Lys Thr Ala
        370                 375                 380

Lys Gly Leu Asp Phe Glu Ala Lys Gln Gln Tyr Ile Leu His Val Ala
385                 390                 395                 400

Val Thr Asn Val Val Pro Phe Glu Val Ser Leu Thr Thr Ser Thr Ala
                405                 410                 415

Thr Val Thr Val Asp Val Leu Asp Val Asn Glu Ala Pro Ile Phe Val
            420                 425                 430

Pro Pro Glu Lys Arg Val Glu Val Ser Glu Asp Phe Gly Val Gly Gln
        435                 440                 445

Glu Ile Thr Ser Tyr Thr Ala Gln Glu Pro Asp Thr Phe Met Glu Gln
        450                 455                 460

Lys Ile Thr Tyr Arg Ile Trp Arg Asp Thr Ala Asn Trp Leu Glu Ile
465                 470                 475                 480

Asn Pro Asp Thr Gly Ala Ile Ser Thr Arg Ala Glu Leu Asp Arg Glu
                485                 490                 495

Asp Phe Glu His Val Lys Asn Ser Thr Tyr Thr Ala Leu Ile Ile Ala
            500                 505                 510

Thr Asp Asn Gly Ser Pro Val Ala Thr Gly Thr Gly Thr Leu Leu Leu
            515                 520                 525

Ile Leu Ser Asp Val Asn Asp Asn Ala Pro Ile Pro Glu Pro Arg Thr
        530                 535                 540

Ile Phe Phe Cys Glu Arg Asn Pro Lys Pro Gln Val Ile Asn Ile Ile
545                 550                 555                 560
```

Asp Ala Asp Leu Pro Pro Asn Thr Ser Pro Phe Thr Ala Glu Leu Thr
            565                 570                 575

His Gly Ala Ser Ala Asn Trp Thr Ile Gln Tyr Asn Asp Pro Thr Gln
        580                 585                 590

Glu Ser Ile Ile Leu Lys Pro Lys Met Ala Leu Glu Val Gly Asp Tyr
    595                 600                 605

Lys Ile Asn Leu Lys Leu Met Asp Asn Gln Asn Lys Asp Gln Val Thr
610                 615                 620

Thr Leu Glu Val Ser Val Cys Asp Cys Glu Gly Ala Ala Gly Val Cys
625                 630                 635                 640

Arg Lys Ala Gln Pro Val Glu Ala Gly Leu Gln Ile Pro Ala Ile Leu
                645                 650                 655

Gly Ile Leu Gly Gly Ile Leu Ala Leu Leu Ile Leu Ile Leu Leu Leu
            660                 665                 670

Leu Leu Phe Leu Arg Arg Arg Ala Val Val Lys Glu Pro Leu Leu Pro
        675                 680                 685

Pro Glu Asp Asp Thr Arg Asp Asn Val Tyr Tyr Asp Glu Glu Gly
    690                 695                 700

Gly Gly Glu Glu Asp Gln Asp Phe Asp Leu Ser Gln Leu His Arg Gly
705                 710                 715                 720

Leu Asp Ala Arg Pro Glu Val Thr Arg Asn Asp Val Ala Pro Thr Leu
                725                 730                 735

Met Ser Val Pro Arg Tyr Leu Pro Arg Pro Ala Asn Pro Asp Glu Ile
            740                 745                 750

Gly Asn Phe Ile Asp Glu Asn Leu Lys Ala Ala Asp Thr Asp Pro Thr
        755                 760                 765

Ala Pro Pro Tyr Asp Ser Leu Leu Val Phe Asp Tyr Glu Gly Ser Gly
    770                 775                 780

Ser Glu Ala Ala Ser Leu Ser Ser Leu Asn Ser Ser Glu Ser Asp Lys
785                 790                 795                 800

Asp Gln Asp Tyr Asp Tyr Leu Asn Glu Trp Gly Asn Arg Phe Lys Lys
                805                 810                 815

Leu Ala Asp Met Tyr Gly Gly Gly Glu Asp Asp
            820                 825

<210> SEQ ID NO 28
<211> LENGTH: 2486
<212> TYPE: DNA
<213> ORGANISM: Homo sapiens

<400> SEQUENCE: 28
tgaattttga agattgcacc ggtcgacaaa ggacagccta tttttccctc gacacccgat      60
tcaaagtggg cacagatggt gtgattacag tcaaaaggcc tctacggttt cataacccac     120
agatccattt cttggtctac gcctgggact ccacctacag aaagttttcc accaaagtca     180
cgctgaatac agtggggcac caccaccgcc cccgcccca tcaggcctcc gtttctggaa      240
tccaagcaga attgctcaca tttcccaact cctctcctgg cctcagaaga cagaagagag     300
actgggttat tcctcccatc agctgcccag aaaatgaaaa aggcccattt cctaaaaacc     360
tggttcagat caaatccaac aaagacaaag aaggcaaggt tttctacagc atcactggcc     420
aaggagctga cacccccct gttggtgtct ttattattga agagaaaaca ggatggctga     480
aggtgacaga gcctctggat agagaacgca ttgccacata cactctcttc tctcacgctg     540
tgtcatccaa cgggaatgca gttgaggatc caatggagat tttgatcacg gtaaccgatc     600

```
agaatgacaa caagcccgaa ttcacccagg aggtctttaa ggggtctgtc atggaaggtg    660
ctcttccagg aacctctgtg atggaggtca cagccacaga cgcggacgat gatgtgaaca    720
cctacaatgc cgccatcgct tacaccatcc tcagccaaga tcctgagctc cctgacaaaa    780
atatgttcac cattaacagg aacacaggag tcatcagtgt ggtcaccact gggctggacc    840
gagagagttt ccctacgtat accctggtgg ttcaagctgc tgaccttcaa ggtgaggggt    900
taagcacaac agcaacagct gtgatcacag tcactgacac caacgataat cctccgatct    960
tcaatcccac cacgtacaag ggtcaggtgc ctgagaacga ggctaacgtc gtaatcacca   1020
cactgaaagt gactgatgct gatgccccca taccccagc gtgggaggct gtataccaca   1080
tattgaatga tgatggtgga caatttgtcg tcaccacaaa tccagtgaac aacgatggca   1140
ttttgaaaac agcaagggc ttggattttg aggccaagca gcagtacatt ctacacgtag   1200
cagtgacgaa tgtggtacct tttgaggtct ctctcaccac ctccacagcc accgtcaccg   1260
tggatgtgct ggatgtgaat gaagccccca tctttgtgcc tcctgaaaag agagtggaag   1320
tgtccgagga ctttggcgtg ggccaggaaa tcacatccta cactgcccag gagccagaca   1380
catttatgga acagaaaata acatatcgga tttggagaga cactgccaac tggctggaga   1440
ttaatccgga cactggtgcc atttccactc gggctgagct ggacagggag gattttgagc   1500
acgtgaagaa cagcacgtac acagccctaa tcatagctac agacaatggt tctccagttg   1560
ctactggaac agggacactt ctgctgatcc tgtctgatgt gaatgacaac gcccccatac   1620
cagaacctcg aactatattc ttctgtgaga ggaatccaaa gcctcaggtc ataaacatca   1680
ttgatgcaga ccttcctccc aatacatctc ccttcacagc agaactaaca cacggggcga   1740
gtgccaactg gaccattcag tacaacgacc caacccaaga atctatcatt ttgaagccaa   1800
agatggcctt agaggtgggt gactacaaaa tcaatctcaa gctcatggat aaccagaata   1860
aagaccaagt gaccacctta gaggtcagcg tgtgtgactg tgaaggggcc gccggcgtct   1920
gtaggaaggc acagcctgtc gaagcaggat tgcaaattcc tgccattctg gggattcttg   1980
gaggaattct tgctttgcta attctgattc tgctgctctt gctgtttctt cggaggagag   2040
cggtggtcaa agagccctta ctgccccag aggatgacac ccgggacaac gtttattact   2100
atgatgaaga aggaggcgga gaagaggacc aggactttga cttgagccag ctgcacaggg   2160
gcctggacgc tcggcctgaa gtgactcgta cgacgttgc accaaccctc atgagtgtcc   2220
cccggtatct tccccgcct gccaatcccg atgaaattgg aaatttttatt gatgaaaatc   2280
tgaaagcggc tgatactgac cccacagccc cgccttatga ttctctgctc gtgtttgact   2340
atgaaggaag cggttccgaa gctgctagtc tgagctccct gaactcctca gagtcagaca   2400
aagaccagga ctatgactac ttgaacgaat ggggcaatcg cttcaagaag ctggctgaca   2460
tgtacggagg cggcgaggac gactag                                       2486
```

<210> SEQ ID NO 29
<211> LENGTH: 1965
<212> TYPE: PRT
<213> ORGANISM: Synechocystis sp.

<400> SEQUENCE: 29

Met Ser Val Tyr Asn Leu Asp Leu Ser Leu Val Tyr Gly Lys Leu Ser
1               5                   10                  15

Ala Phe Ala Gly Leu Glu Ser Phe Trp Gln Asn Phe Glu Ile Ile Tyr
            20                  25                  30

Gly Asn Asn Tyr Asp Val Val Ala Val Glu Ala Leu Arg Ser Arg Trp

```
                  35                  40                  45
Ala Ile Gly Asp Phe Ser Asp Leu Pro Val Ile Glu Val Leu Ser Ala
 50                  55                  60

Glu Thr Leu Gly Ser Ala Val Gly Ala Tyr Ala Gln Ser Ile Asn Lys
 65                  70                  75                  80

Ile Tyr Leu Ser Asp Gln Phe Val Ala Thr Pro Pro Asp Ala Leu
                 85                  90                  95

Ile Glu Val Ile Leu Glu Glu Ile Gly His Phe Val Asp Ala Gln Val
                100                 105                 110

Asn Ala Val Asp Thr Ile Gly Asp Glu Gly Gln Leu Phe Ala Asp Leu
                115                 120                 125

Val Leu Gly Asp Val Val Ser Ala Ser Glu Leu Ala Arg Ile Lys Ala
                130                 135                 140

Glu Asp Asp Thr His Thr Ile Ile Asn Gly Gln Ser Leu Gln Val
145                 150                 155                 160

Glu Gln Ser Val Gln Ser Leu Ile Gly Glu Ser Val Thr Val Asn Val
                165                 170                 175

Arg Phe Thr Gly Ser Gly Ser Asp Gly Ser Phe Asn Phe Asp Leu Phe
                180                 185                 190

Thr Gln Thr Phe Thr Val Thr Ser Gly Gln Glu Ile Thr Asp Gln Ala
                195                 200                 205

Ile Thr Ala Thr Phe Asn Ser Ser Gly Ser Pro Gln Thr Leu Thr Gly
                210                 215                 220

Asn Val Asp Ile Asp Val Ser Glu Asn Thr Ile Tyr Val Asn Phe Ser
225                 230                 235                 240

Gly Thr Gln Gln Gly Gly Ala Leu Thr Phe Ile Phe Thr Ser Leu Ala
                245                 250                 255

Asp Glu Ser Ile Gly Ser Val Glu Ser Val Ile Gln Thr Asn Val Ser
                260                 265                 270

Gly Phe Thr Thr Gly Val Asn Gln Pro Leu Thr Pro Ser Val Ser Asn
                275                 280                 285

Asn Asn Val Thr Val Gly Phe Phe Pro Phe Gly Ser Gln Pro Gly Val
290                 295                 300

Asn Leu Ser Gln Thr Ser Thr Leu Thr Tyr Gly Thr Pro Pro Thr Asp
305                 310                 315                 320

Asn Thr Pro Pro Asn Ala Pro Ser Thr Pro Asp Leu Ser Ala Ser Ser
                325                 330                 335

Asp Ser Gly Leu Ser Ser Thr Asp Asn Ile Thr Asn Asp Thr Thr Pro
                340                 345                 350

Thr Phe Asn Gly Thr Ala Glu Ala Asn Ser Thr Val Thr Leu Phe Ser
                355                 360                 365

Gly Gly Ser Thr Gln Ile Gly Ser Thr Thr Ala Asn Gly Ser Gly Asn
                370                 375                 380

Trp Thr Ile Thr Ala Ser Thr Pro Ala Asp Gly Asn Tyr Ser Ile Thr
385                 390                 395                 400

Ala Lys Ala Thr Asp Ala Ala Gly Asn Val Ser Thr Ala Ser Ser Ala
                405                 410                 415

Leu Gly Ile Thr Ile Asp Asn Thr Pro Asn Leu Ala Ser Ala Ile
                420                 425                 430

Glu Ile Ser Asp Thr Ala Leu Lys Ile Gly Asp Thr Ala Thr Val Thr
                435                 440                 445

Phe Thr Phe Ser Glu Ala Val Ile Gly Phe Thr Asn Ala Asp Ile Ile
                450                 455                 460
```

```
Val Val Asp Gly Ser Leu Ser Pro Thr Ser Asp Gly Gly Ile
465                 470                 475                 480

Thr Trp Thr Ala Thr Leu Thr Pro Asn Ala Asn Ala Glu Ser Asn Ser
                        485                 490                 495

Asn Val Ile Thr Leu Asp Asn Thr Gly Ile Ser Asp Leu Ala Gly Asn
                500                 505                 510

Asn Gly Thr Gly Thr Thr Thr Ser Val Ser Tyr Ala Val Asp Thr Ile
                515                 520                 525

Pro Pro Thr Leu Thr Ser Ile Asp Asp Gly Asp Asp Asp Asn Ile Val
                530                 535                 540

Pro Ile Asp Thr Pro Leu Thr Tyr Thr Leu Thr Phe Ser Glu Asp Ile
545                 550                 555                 560

Asp Ser Thr Thr Val Thr Ala Asp Asp Phe Asp Asn Ala Gly Thr Ala
                565                 570                 575

Thr Ile Ser Ile Gly Thr Ile Thr Glu Thr Ser Ser Gly Val Phe Ser
                580                 585                 590

Val Val Val Thr Pro Asn Thr Ser Gly Thr Ile Ile Leu Gln Ile Pro
                595                 600                 605

Asn Gly Ala Val Leu Ser Asp Met Ala Gly Asn Asn Leu Ala Val Pro
                610                 615                 620

Val Gln Asp Asp Asp Glu Leu Gln Val Asn Gln Gly Pro Ser Ala Val
625                 630                 635                 640

Ile Val Pro Asn Ala Ser Leu Ala Glu Asn Thr Asp Thr Thr Asn Pro
                645                 650                 655

Leu Lys Val Ala Asp Ile Ala Ile Thr Asp Asp Gly Leu Gly Ser Asn
                660                 665                 670

Asp Ile Ser Leu Ser Gly Ile Asp Ala Ala Phe Phe Glu Val Ile Gly
                675                 680                 685

Gln Ser Leu Phe Leu Lys Ala Gly Thr Val Leu Asn Phe Glu Ser Lys
                690                 695                 700

Ala Ser Tyr Thr Val Thr Val Asn Val Asp Asp Asp Thr Val Gly Ser
705                 710                 715                 720

Thr Pro Asp Leu Thr Ala Asp Phe Lys Leu Thr Ile Asn Asn Leu Asp
                725                 730                 735

Glu Val Ala Pro Thr Ile Thr Ser Gly Asp Thr Ala Lys Ala Ile Ala
                740                 745                 750

Glu Asn Ser Gly Ala Asn Gln Ile Ile Tyr Gln Val Lys Ala Thr Asp
                755                 760                 765

Asp Gly Asp Ile Ser Ala Gly Ile Thr Phe Gly Leu Lys Pro Gly Asp
                770                 775                 780

Asp Ala Asp Ser Phe Ile Ile Asn Ala Thr Thr Gly Glu Val Lys Leu
785                 790                 795                 800

Ile Gly Asn Pro Asp Phe Glu Thr Gln Ser Ser Tyr Lys Phe Thr Val
                805                 810                 815

Thr Ala Asp Asp Gly Val Asn Pro Ala Thr Glu Gln Leu Val Asn Leu
                820                 825                 830

Ala Ile Ile Asp Leu Asp Glu Ile Ala Pro Thr Ile Thr Ser Gly Asp
                835                 840                 845

Thr Ala Lys Ala Ile Ala Glu Asn Ser Gly Ala Asn Gln Val Ile Tyr
                850                 855                 860

Gln Val Thr Ala Thr Asp Asp Ala Asp Val Ser Ala Gly Ile Thr Phe
865                 870                 875                 880
```

-continued

Gly Leu Lys Pro Gly Asn Asp Ala Asp Leu Phe Ile Ile Asn Ser Thr
            885                 890                 895

Thr Gly Gln Val Ile Leu Thr Glu Asn Pro Asp Phe Glu Thr Gln Ser
        900                 905                 910

Ser Tyr Lys Phe Thr Val Thr Ala Ser Asp Gly Val Asn Pro Ala Thr
        915                 920                 925

Glu Lys Ile Val Thr Leu Ala Ile Ile Asp Leu Asp Glu Ile Ala Pro
        930                 935                 940

Thr Ile Thr Ser Gly Asp Thr Ala Lys Ala Ile Thr Glu Asn Ser Gly
945                 950                 955                 960

Ala Asn Gln Val Ile Tyr Glu Val Ile Ala Thr Asp Asp Ala Asp Val
            965                 970                 975

Ser Ala Gly Ile Thr Phe Gly Leu Lys Pro Gly Asn Asp Ala Gly Ser
            980                 985                 990

Phe Thr Ile Asn Pro Ile Thr Gly Lys Val Thr Leu Ile Asp Asp Pro
            995                1000                1005

Asp Phe Glu Thr Gln Ser Ser Tyr Lys Phe Thr Val Thr Ala Ser
        1010                1015                1020

Asp Gly Val Asn Leu Ala Thr Glu Gln Leu Val Asn Leu Thr Ile
        1025                1030                1035

Ile Asp Leu Asp Glu Ile Ala Pro Thr Ile Thr Ser Gly Asp Thr
        1040                1045                1050

Ala Lys Ala Ile Ala Glu Asn Ser Gly Ala Asn Gln Val Ile Tyr
        1055                1060                1065

Glu Val Ile Ala Thr Asp Asp Ala Asp Val Ser Ala Gly Ile Thr
        1070                1075                1080

Phe Gly Leu Lys Pro Gly Asn Asp Ala Gly Ser Phe Thr Ile Asn
        1085                1090                1095

Pro Ile Thr Gly Lys Val Thr Leu Ile Asp Asp Pro Asp Phe Glu
        1100                1105                1110

Thr Gln Ser Ser Tyr Lys Phe Thr Val Thr Ala Ser Asp Gly Val
        1115                1120                1125

Asn Leu Ala Thr Glu Gln Leu Val Asn Leu Thr Ile Ile Asp Leu
        1130                1135                1140

Asp Glu Ile Ala Pro Thr Ile Thr Ser Gly Asp Thr Ala Lys Ala
        1145                1150                1155

Ile Thr Glu Asn Ser Gly Ala Asn Gln Ile Ile Tyr Gln Ala Thr
        1160                1165                1170

Ala Asp Asp Asn Ala Asp Ile Ser Ala Gly Val Thr Phe Gly Leu
        1175                1180                1185

Lys Pro Gly Asp Asp Ala Asp Ser Phe Ile Ile Asn Ala Ile Thr
        1190                1195                1200

Gly Gln Val Thr Leu Leu Asp Asn Pro Asp Phe Glu Thr Gln Ser
        1205                1210                1215

Ser Tyr Lys Phe Thr Val Thr Ala Ser Asp Gly Val Asn Pro Val
        1220                1225                1230

Thr Glu Gln Val Val Asn Leu Thr Ile Ile Asp Leu Asp Glu Ile
        1235                1240                1245

Ala Pro Thr Ile Thr Ser Gly Asn Thr Ala Lys Ala Ile Ala Glu
        1250                1255                1260

Asn Ser Gly Ala Asn Gln Val Ile Tyr Gln Val Thr Ala Thr Asp
        1265                1270                1275

Asp Ala Asp Ile Ser Ala Glu Val Thr Phe Gly Leu Lys Leu Gly

```
                  1280              1285              1290

Asp Asp Ala Thr Ser Phe Ser Ile Asp Ser Thr Thr Gly Lys Val
    1295            1300            1305

Thr Leu Ile Asn Asn Pro Asp Phe Glu Ser Gln Ser Ser Tyr Lys
    1310            1315            1320

Phe Thr Val Thr Ala Ser Asp Gly Val Asn Pro Ala Thr Glu Lys
    1325            1330            1335

Ile Val Thr Leu Ala Ile Asn Asn Leu Asp Glu Ile Gly Pro Thr
    1340            1345            1350

Ile Thr Ser Gly Asp Thr Ala Thr Pro Ile Asp Glu Asn Ser Gly
    1355            1360            1365

Ala Asn Gln Leu Ile Tyr Gln Val Ile Ala Thr Asp Asp Ala Asp
    1370            1375            1380

Val Ser Ala Gly Ile Thr Phe Gly Leu Lys Pro Gly Asn Asp Ala
    1385            1390            1395

Gly Ser Phe Thr Ile Asn Pro Ile Thr Gly Glu Val Thr Leu Ile
    1400            1405            1410

Asp Asp Pro Asp Phe Glu Thr Gln Ser Ser Tyr Lys Phe Thr Val
    1415            1420            1425

Thr Ala Ser Asp Gly Val Asn Pro Ala Thr Glu Lys Ile Val Thr
    1430            1435            1440

Leu Thr Ile Asn Asp Leu Asp Glu Leu Gly Pro Asn Ile Thr Ser
    1445            1450            1455

Asp Asn Ile Ala Thr Ala Ile Asn Glu Asn Ser Gly Ala Asn Gln
    1460            1465            1470

Ile Ile Tyr Gln Val Thr Ala Asp Asp Gly Asp Asp Ile Ser Ala
    1475            1480            1485

Gly Val Thr Phe Gly Leu Lys Pro Gly Asp Asn Ala Asn Gln Phe
    1490            1495            1500

Ser Ile Asp Pro Thr Thr Gly Gln Val Thr Leu Leu Asp Asn Pro
    1505            1510            1515

Asp Phe Glu Thr Gln Ser Ser Tyr Lys Phe Thr Val Thr Ala Ser
    1520            1525            1530

Asp Gly Val Asn Pro Ala Thr Glu Gln Leu Val Asn Leu Thr Ile
    1535            1540            1545

Ile Asp Leu Asp Glu Ile Ala Pro Thr Ile Thr Ser Gly Asp Thr
    1550            1555            1560

Ala Lys Ala Ile Ala Glu Asn Ser Gly Ala Asn Gln Val Ile Tyr
    1565            1570            1575

Gln Val Thr Ala Thr Asp Asp Ala Asp Thr Ser Ala Gly Val Thr
    1580            1585            1590

Phe Gly Leu Lys Pro Gly Glu Asp Ala Asn Ser Phe Thr Ile Asn
    1595            1600            1605

Ala Ala Thr Gly Glu Val Glu Leu Ile Gly Asn Pro Asp Phe Glu
    1610            1615            1620

Thr Gln Ser Ser Tyr Lys Phe Thr Val Thr Ala Ser Asp Gly Val
    1625            1630            1635

Asn Pro Val Thr Glu Gln Val Val Asn Leu Thr Ile Ile Asp Leu
    1640            1645            1650

Asp Glu Ile Ala Pro Thr Ile Thr Ser Gly Asn Thr Ala Lys Ala
    1655            1660            1665

Ile Ala Glu Asn Ser Gly Ala Asn Gln Val Ile Tyr Gln Val Thr
    1670            1675            1680
```

Ala Thr Asp Asp Ala Asp Ile Ser Ala Gly Val Thr Phe Gly Leu
1685                1690                1695

Lys Pro Gly Asp Asp Ala Thr Ser Phe Ser Ile Asp Ser Thr Thr
1700                1705                1710

Gly Lys Val Thr Leu Ile Asn Asn Pro Asp Phe Glu Ser Gln Ser
1715                1720                1725

Ser Tyr Arg Phe Thr Val Thr Ala Asp Asp Gly Val Asn Pro Val
1730                1735                1740

Thr Glu Gln Gln Ile Ala Leu Glu Ile Leu Asp Asp Asn Val Ala
1745                1750                1755

Val Ile Glu Asn Gly Phe Phe Phe Ala Gln Phe Leu Asp Asn Thr
1760                1765                1770

Arg Gln Ala Leu Leu Phe Gln Asn Gln Pro Phe Ser Thr Asp Gln
1775                1780                1785

Ser Val Asn Trp Lys Ile Leu Asp Thr Glu Thr Val Asp Gly Ser
1790                1795                1800

Asn Gln Val Leu Trp Tyr Asn Gln Val Thr Glu Glu Val Gly Val
1805                1810                1815

Trp Leu Thr Asp Asn Asn Trp Asn Trp Ile Ser Ser Asp Thr Trp
1820                1825                1830

Gln Val Lys Ser Ser Arg Thr Phe Asn Thr Glu Leu Leu Phe Gly
1835                1840                1845

Thr Asp Ile Asn Gly Asp Ser Leu Ile Gly Asp Gln Tyr Thr Val
1850                1855                1860

Leu Glu Asn Gln Gly Ala Val Gly Leu Leu Glu Gly Ile Phe Gly
1865                1870                1875

Ala Tyr Tyr Val Gln Pro Gly Asp Asp Pro Val Thr Pro Leu Lys
1880                1885                1890

Phe Leu Gly Gln Pro Phe Glu Asn Gln Phe Gly Ser Trp Gln Ala
1895                1900                1905

Leu Ala Ala Glu Arg Val Glu Asn Ile Asn Arg Val Leu Trp Gln
1910                1915                1920

Asn Phe Asp Thr Gly Glu Ile Gly Ile Trp Arg Thr Asp Asn Asn
1925                1930                1935

Trp Asn Trp Leu Ser Ser Asn Val Phe Thr Pro Asn Ser Thr Glu
1940                1945                1950

Ile Ala Thr Val Glu Ser Leu Phe Gly Ile Ser Leu
1955                1960                1965

<210> SEQ ID NO 30
<211> LENGTH: 5898
<212> TYPE: DNA
<213> ORGANISM: Synechocystis sp.

<400> SEQUENCE: 30
atgagcgtct acaatcttga tttgtcctta gtctatggga aactgtccgc ttttgcaggc    60
ttggagagtt tttggcagaa tttcgagatt atttatggaa ataattatga tgttgtcgcc   120
gtagaagctt tgcgaagtcg ttgggctatt ggagatttta gcgatcttcc tgtcattgaa   180
gtactcagtg ccgaaacctt gggctctgct gtgggagcct atgcccaaag tatcaataaa   240
atttatctgt ctgaccaatt tgttgccact gccccccag acgctctgat tgaagtcatc   300
ctcgaagaga ttggacattt tgtggatgct caagttaacg cagtcgatac cataggagat   360
gaaggacaat tatttgcaga tctagtgttg ggagatgttg tctctgcgtc ggaattggca   420

-continued

```
aggataaaag ccgaagatga tacacacacc atcattatca atggtcaatc attacaggtt    480
gaacagtcag tacagtcttt aataggcgag tcggttactg tcaatgtgcg tttcaccggt    540
agtggttctg atggcagctt caattttgac ctgtttaccc aaacatttac cgtaacgtca    600
ggacaggaaa tcacagatca agctatcact gctacttta attcatcagg atcccccaa     660 acgctgaccg gcaacgtaga catagatgta tcggaaaata ccatctatgt gaattttcg    720 ggtactcagc aaggaggagc tttaactttc atttttacat ctctagcaga tgaatcaata   780
ggttctgttg aatctgtgat tcagacaaat gtatctggtt tcactactgg cgttaaccaa    840
cctctcaccc cttctgtatc aaacaataat gttactgttg ttttttccc ctttggttct    900 cagcctggcg ttaatctctc tcagacctct acacttacct atggaactcc ccccacggat    960
aacactccgc ccaatgcccc gtctacgcca gatttgagtg caagcagtga tagtgggctt   1020
tctagtacag acaacatcac caatgacacc acaccaacgt taacggtac ggctgaagcc    1080 aacagcacgg taaccctatt tagtggaggt agtacccaga taggaagcac cactgccaat   1140
ggctcaggaa attggacaat tacggcttcg actccagctg atggcaacta cagtattact   1200
gccaaagcta ccgatgctgc gggcaatgtt agtacggctt cttcagcctt aggcattact   1260
attgataaca ctactccaaa cctcgctagt gctattgaga ttagtgacac cgctctaaaa   1320
atcggtgata cagcgaccgt tacctttact ttttccgaag cagtaattgg gtttacaaat   1380
gcagatatta ttgtcgtcga cggttctttg tcatctccaa cgtcatccga cggaggaata   1440
acctggacag ccactcttac cccaaatgct aatgctgaat ctaattccaa tgttattacc   1500
ctagacaata cagggattag tgacctagct gggaataacg gaaccggcac aacaacatca   1560
gttagctatg ctgtagatac tattcccct acactcacct ctattgatga tggggatgat    1620
gataacattg ttcctatcga cactccgctg acctatcccc tgaccttcag tgaagatata   1680
gactccacaa ctgtcactgc tgatgatttt gacaatgcgg gaacagcgac aatttctatt   1740
ggaaccatta cagaaaccag ctcgggggta ttttctgtag ttgtcactcc taacacttca   1800
ggcactatca ttctgcagat tcctaatggg gcagtgctta gcgatatggc aggcaataat   1860
ctagcagtcc ctgtgcaaga tgatgatgaa cttcaagtca accaaggacc cagcgctgtt   1920
atagttccta atgccagtct ggcagaaaat accgatacta cgaacccact caaagtagcg   1980
gatattgcta ttaccgatga tggtttaggg agtaatgata tcagcctgtc aggtattgat   2040
gcagcctttt ttgaagtcat tgggcagagt ctctttctca aggctggtac agtattgaac   2100
tttgagagta aagccagcta taccgtcaca gtgaatgtgg atgatgacac ggtaggtagt   2160 accctgact tgactgcgga tttcaagtta actatcaata acctagatga agtagcgcca    2220
accatcacat cggagatac agcaaaggcg atcgccgaaa atagtggtgc gaatcaaata    2280
atttaccaag taaaagcaac ggatgatggt gacataagtg caggaataac ctttggcttg   2340
aaaccggggg atgatgctga ctcgtttatc atcaatgcca ccactggaga agttaagtta   2400
attggcaatc ctgactttga aacccaatcc agttataaat tcaccgttac tgctgacgat   2460
ggagttaacc cggccaccga acaattggtt aatttagcca tcattgacct agacgaaata   2520
gctcctacta tcacatcggg agatacgcg aaggcgatcc ccgaaaatag tggtgcgaat    2580
caagtaattt atcaagtcac tgccacagat gatgctgacg taagtgcagg aataacattt    2640
ggtttaaagc cagggaatga tgctgacctg tttatcatca actccaccac cggacaagta   2700
atcctaactg aaaacccaga ttttgaaaca caatccagtt ataaattcac ggttactgct   2760
```

```
agcgatgggg ttaatcctgc caccgaaaaa atagttaccc tagccatcat tgacttagac    2820
gaaatagctc ctactatcac atcgggagat acggcaaagg cgatcaccga aaatagtggt    2880
gccaatcaag taatttacga agttattgcc acagatgatg ctgacgtaag tgccggaata    2940
acatttggtt taaagccagg gaatgatgct ggttcattta ccatcaatcc catcaccggg    3000
aaagtaaccc tcattgatga cccggacttt gaaacacaat caagttataa attcaccgtt    3060
actgccagcg atggtgttaa cctgccacac gagcaattag tcaacttaac catcattgac    3120
ttagatgaaa tagctccaac catcacatcg ggggatacag caaaggcgat cgccgaaaat    3180
agtggtgcca atcaagtaat ttacgaagtt attgccacag atgatgctga cgtaagtgcc    3240 ggataacat ttggtttaaa gccagggaat gatgctggtt catttaccat caatcccatc    3300
accgggaaag taaccctcat tgatgacccg gactttgaaa cacaatcaag ttataaattc    3360
accgttactg ccagcgatgg tgttaacctg gccacggagc aattagtcaa cttaaccatc    3420
attgacttag atgaaatagc tccaaccatc acatcggggg atacagcaaa ggcgatcacc    3480
gaaaatagtg gtgcgaatca gataatttac caggcaacag cggatgataa tgcggatata    3540
agtgccgggg taacctttgg cttgaaacca ggggatgatg ctgactcgtt tatcatcaat    3600
gccatcactg acaagttac cttacttgat aacccagact ttgaaaccca atcaagttat    3660
aaattcactg tcactgccag cgatggtgtg aatcctgtca ctgagcaagt tgtcaattta    3720
accatcattg acttagatga aatagcccca actattacat cggaaatac agcaaaggcg    3780 atcgccgaaa acagtggtgc gaatcaagta atttaccaag tcactgccac agatgatgct    3840
gacataagtg ccgaagtaac ctttgggttg aaattgggtg atgatgccac atctttcagc    3900
attgactcca acaggcaa agtaacttta atcaacaatc ctgactttga agccaatcc    3960 agttataaat tcaccgttac tgctagcgat ggtgtgaatc ccgccaccga aaaaatagtt    4020
accctagcca tcaataatct agacgaaata ggcccgacca ttacatcagg cgatacagca    4080
acgcctattg atgaaaacag tggtgccaat caactaatttt accaagttat tgccacagat    4140
gatgctgacg taagtgccgg aataacattt ggtttaaagc cagggaatga tgctggctca    4200
tttactatca atcccatcac cggggaagta accctcattg atgacccgga ctttgaaacc    4260
caatcaagtt ataaattcac cgttactgcc agcgatggtg ttaaccctgc tacggaaaaa    4320
atagttaccc tgactattaa tgatctggac gaactcggtc ccaatattac atctgataat    4380
atcgcaacag caattaatga aaacagtggt gcgaatcaga taatttacca agtaacagca    4440
gacgatggtg atgatatcag tgccggagtg accttttggct taaagccggg agacaatgcc    4500
aaccagttca gtattgatcc aacaactgga caagttacct tacttgataa cccagactttt    4560 gaaacccaat caagttataa attcacggtc actgccagcg atggcgttaa ccctgccacg    4620
gagcaattag tcaacttaac catcattgat cttgatgaaa tagctccaac cattactagt    4680
ggagatacgg caaagcgat tgccgaaaat agtggtgcga atcaagtaat ttaccaagta    4740
acagcaacgg atgatgctga cacaagtgca ggagtaacct tcggcttaaa accaggagaa    4800
gatgctaact catttaccat caatgccgcc actggagaag ttgagttaat tggcaatcca    4860
gactttgaaa cccaatcaag ttataaattc actgtcactg ccagcgatgg tgtgaatcct    4920
gtcacggagc aagttgttaa tttaaccatc atcgacctag acgaaatagc cccaactatt    4980
acatcgggaa atacagcaaa ggcgatcgcc gaaaatagtg gtgccaatca agtaatttat    5040
caagtcactg ccagagatga tgctgacata agtgcgggag taacctttgg cttgaaacca    5100
ggggatgatg ccacatcttt cagcattgac tccacaacag gcaaagtaac tttaatcaac    5160
```

```
aatcctgact ttgaaagcca atccagttat agattcaccg ttactgctga cgatggcgtt   5220
aatccagtta ctgaacaaca aatcgcatta gaaatcttag atgacaatgt tgctgttatt   5280
gaaaatggct ttttcttcgc tcaattttta gataatactc gccaagctct tttgtttcag   5340
aatcaaccat tctctactga tcaatctgta aactggaaaa tcttagacac agaaactgtt   5400
gatggctcca atcaagtgct ttggtacaat caagttactg aagaagttgg tgtatggctg   5460
actgataata attggaactg gatttcttct gacacatggc aagtgaaatc atcaagaact   5520
tttaataccg aattattatt tgggacggac attaacggag attctctcat tggcgatcaa   5580
tacactgttt tagaaaatca aggtgcggtt ggtctcctgg aaggaatttt tggcgcttac   5640
tatgttcagc ccggggatga cccagttact cctcttaaat ttttagggca accattcgag   5700
aatcagtttg gtagttggca agccctagcc gcagaaaggg ttgaaaacat caaccgagtt   5760
ttatggcaaa attttgacac cggagaaatt ggaatttggc gaacagacaa taattggaat   5820
tggctttctt ccaatgtttt tacccccaat tccactgaaa tagccaccgt tgaaagcctt   5880
tttggcatta gcctttag                                                 5898
```

<210> SEQ ID NO 31
<211> LENGTH: 211
<212> TYPE: PRT
<213> ORGANISM: Homo sapiens

<400> SEQUENCE: 31

```
Met Ala Asn Ala Gly Leu Gln Leu Leu Gly Phe Ile Leu Ala Phe Leu
1               5                   10                  15

Gly Trp Ile Gly Ala Ile Val Ser Thr Ala Leu Pro Gln Trp Arg Ile
            20                  25                  30

Tyr Ser Tyr Ala Gly Asp Asn Ile Val Thr Ala Gln Ala Met Tyr Glu
        35                  40                  45

Gly Leu Trp Met Ser Cys Val Ser Gln Ser Thr Gly Gln Ile Gln Cys
    50                  55                  60

Lys Val Phe Asp Ser Leu Leu Asn Leu Ser Ser Thr Leu Gln Ala Thr
65                  70                  75                  80

Arg Ala Leu Met Val Val Gly Ile Leu Leu Gly Val Ile Ala Ile Phe
                85                  90                  95

Val Ala Thr Val Gly Met Lys Cys Met Lys Cys Leu Glu Asp Asp Glu
            100                 105                 110

Val Gln Lys Met Arg Met Ala Val Ile Gly Gly Ala Ile Phe Leu Leu
        115                 120                 125

Ala Gly Leu Ala Ile Leu Val Ala Thr Ala Trp Tyr Gly Asn Arg Ile
    130                 135                 140

Val Gln Glu Phe Tyr Asp Pro Met Thr Pro Val Asn Ala Arg Tyr Glu
145                 150                 155                 160

Phe Gly Gln Ala Leu Phe Thr Gly Trp Ala Ala Ser Leu Cys Leu
                165                 170                 175

Leu Gly Gly Ala Leu Leu Cys Cys Ser Cys Pro Arg Lys Thr Thr Ser
            180                 185                 190

Tyr Pro Thr Pro Arg Pro Tyr Pro Lys Pro Ala Pro Ser Ser Gly Lys
        195                 200                 205

Asp Tyr Val
    210
```

<210> SEQ ID NO 32

<211> LENGTH: 636
<212> TYPE: DNA
<213> ORGANISM: Homo sapiens

<400> SEQUENCE: 32

```
atggccaacg cggggctgca gctgttgggc ttcattctcg ccttcctggg atggatcggc    60
gccatcgtca gcactgccct gccccagtgg aggatttact cctatgccgg cgacaacatc   120
gtgaccgccc aggccatgta cgaggggctg tggatgtcct gcgtgtcgca gagcaccggg   180
cagatccagt gcaaagtctt tgactccttg ctgaatctga gcagcacatt gcaagcaacc   240
cgtgccttga tggtggttgg catcctcctg ggagtgatag caatctttgt ggccaccgtt   300
ggcatgaagt gtatgaagtg cttggaagac gatgaggtgc agaagatgag gatggctgtc   360
attgggggcg cgatatttct tcttgcaggt ctggctattt tagttgccac agcatggtat   420
ggcaatagaa tcgttcaaga attctatgac cctatgaccc cagtcaatgc caggtacgaa   480
tttggtcagg ctctcttcac tggctgggct gctgcttctc tctgccttct gggaggtgcc   540
ctactttgct gttcctgtcc ccgaaaaaca acctcttacc caacaccaag gccctatcca   600
aaacctgcac cttccagcgg gaaagactac gtgtga                            636
```

<210> SEQ ID NO 33
<211> LENGTH: 218
<212> TYPE: PRT
<213> ORGANISM: Mus musculus

<400> SEQUENCE: 33

Met Gly Ser Ala Ala Leu Glu Ile Leu Gly Leu Val Leu Cys Leu Val
1               5                   10                  15

Gly Trp Val Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
        35                  40                  45

Gly Leu Trp Met Ser Cys Val Val Gln Ser Thr Gly His Met Gln Cys
    50                  55                  60

Lys Val Tyr Glu Ser Val Leu Ala Leu Ser Ala Glu Val Gln Ala Ala
65                  70                  75                  80

Arg Ala Leu Thr Val Gly Ala Val Leu Leu Ala Leu Val Ala Leu Phe
                85                  90                  95

Val Thr Leu Thr Gly Ala Gln Cys Thr Thr Cys Val Ala Pro Gly Pro
            100                 105                 110

Val Lys Ala Arg Val Ala Leu Thr Gly Gly Ala Leu Tyr Ala Val Cys
        115                 120                 125

Gly Leu Leu Ala Leu Val Pro Leu Cys Trp Phe Ala Asn Ile Val Val
    130                 135                 140

Arg Glu Phe Tyr Asp Pro Thr Val Pro Val Ser Gln Lys Tyr Glu Leu
145                 150                 155                 160

Gly Ala Ala Leu Tyr Ile Gly Trp Ala Ala Ser Ala Leu Leu Met Cys
                165                 170                 175

Gly Gly Gly Leu Val Cys Cys Gly Ala Trp Val Cys Thr Gly Arg Pro
            180                 185                 190

Glu Phe Ser Phe Pro Val Lys Tyr Ser Ala Pro Arg Arg Pro Thr Ala
        195                 200                 205

Asn Gly Asp Tyr Asp Lys Lys Asn Tyr Val
    210                 215

<210> SEQ ID NO 34
<211> LENGTH: 657
<212> TYPE: DNA
<213> ORGANISM: Mus musculus

<400> SEQUENCE: 34

```
atggggtctg cagcgttgga aattctgggt ctggtgctgt gtctggtagg atgggtgggc    60
ttgatcctgg cgtgtgggct gcccatgtgg caggtgactg ccttcctgga ccacaacatc   120
gtgacggcgc agacgacttg aaggggctg tggatgtcgt gcgtggtgca gagtaccggg    180
cacatgcagt gcaaggtgta tgaatctgtg ctggcgctga gtgcggaggt gcaggcagct   240
cgggcactca ccgtgggcgc tgtgctgctg gcgctggtgg cactctttgt taccttgacc   300
ggcgctcagt gcaccacctg cgtggccccg ggcccagtta aggcacgggt agcactcacg   360
ggaggagcgc tttacgcggt gtgcgggctg ctggcactcg tgccgctctg ctggttcgcc   420
aacatcgttg tccgcgagtt ctatgatccg acggtgccgg tgtcacagaa gtacgagctg   480
ggcgcggcgc tgtacatcgg ctgggcggcc tccgcactgc tcatgtgcgg tggcggcctc   540
gtgtgttgcg gcgcctgggt ctgcaccggg cgccctgagt tcagcttccc ggtcaagtac   600
tctgcgccgc ggcggcccac ggccaatggc gattacgaca agaagaacta tgtctaa      657
```

<210> SEQ ID NO 35
<211> LENGTH: 312
<212> TYPE: PRT
<213> ORGANISM: Caenorhabditis elegans

<400> SEQUENCE: 35

```
Met Pro Lys Asn Tyr His Leu Leu Thr Phe Phe Ser Gly Ser Pro
1               5                   10                  15

Met Phe Ser Ser Pro Cys His Leu Ser Cys Ala Ser Val Phe Ser Leu
                20                  25                  30

Ile Gly Leu Gly Leu Val Cys Phe Ala Val Thr Thr Asp Asn Trp Val
            35                  40                  45

Glu Val Gln Val Asn Arg Arg Glu Ile Ile Asn Ser Phe Lys Arg Glu
        50                  55                  60

Pro Glu Leu Ser Leu Arg Leu Gln Asn Ala Phe Gly His Asn Asn Ile
65                  70                  75                  80

Tyr Phe Ser Arg Asn Tyr Gly Leu Phe Asn Leu Cys Phe Pro Asp Thr
                85                  90                  95

Val Pro Gln Asp Val Gly Ser Phe Ser Lys Met Gly Ser Pro Cys Ile
            100                 105                 110

Trp Ser Asn Glu Phe Met Val Pro Glu Ser Lys Lys Glu His Phe Ser
        115                 120                 125

Asn Asn Glu Leu Tyr Arg His Tyr Ala Ala Lys Ala Thr Ile Ile Ala
    130                 135                 140

Tyr Val Val Gly Ile Val Phe Val Leu Ser Phe Ile Val Gly Leu
145                 150                 155                 160

Ile Gly Cys Trp Asn Arg Ser Lys Lys Phe Ile Met Ser Thr Gly Ile
                165                 170                 175

Leu Leu Ile Leu Ala Gly Leu Ser Met Ser Val Ala Met Leu Leu Trp
            180                 185                 190

His Tyr Val Ala Tyr Ser Glu Arg Tyr Thr Leu Asp Val Glu Pro Tyr
        195                 200                 205

Tyr Lys Ser Trp Glu Pro Ile Leu Lys Leu Thr Ser Arg His Asn Tyr
    210                 215                 220
```

```
Gly Trp Ser Tyr Ile Val Ser Trp Ile Gly Ile Gly Phe Ile Val Ile
225                 230                 235                 240

Gly Ser Ala Phe Met Phe Phe Ala Tyr Ala Ala Val Lys Arg Glu Glu
                245                 250                 255

Glu Asp Ala Leu Thr Ala Lys His Gly Ala Tyr Met Met Pro Asn Tyr
            260                 265                 270

Tyr Asp Lys Gly Ala Gly Thr Ile Val Pro Tyr Asn Tyr Asn Thr Tyr
        275                 280                 285

Ala Gly Tyr Gly Gly Tyr Pro Tyr Tyr Asn Gln Tyr Asn Thr Ala Gly
    290                 295                 300

Tyr Gly Tyr Met Thr Tyr Gly Arg
305                 310
```

<210> SEQ ID NO 36
<211> LENGTH: 939
<212> TYPE: DNA
<213> ORGANISM: Caenorhabditis elegans

<400> SEQUENCE: 36

```
atgccaaaaa attatcactt acttacgttt tttttttcag ggtccccaat gttttcctca      60
ccgtgtcatc tttcgtgcgc ctcggtgttt tccttaattg gcctgggcct cgtatgtttt     120
gcagtgacta ctgataactg ggttgaagtt caggtgaatc aagagaaat cataaactca     180
ttcaaacgag agcccgaatt gagtttacgc cttcaaaatg cttttggtca acaacacatc     240
tacttctctc gcaactatgg tctcttcaat ctttgcttcc ctgatacagt tccacaagat     300
gttggaagct tcagcaaaat gggctctccg tgcatctgga gcaacgagtt catggttcca     360
gagtctaaaa aggagcactt ctcaaacaat gaactttacc gtcattatgc tgcaaaagca     420
actatcattg cttatgttgt tggtattgtt ttcgtcgtgt tgagctttat tgtcggactc     480
atcggatgct ggaatagatc gaaaaaattc attatgagca ccggaattct tctgatcctt     540
gctggacttt caatgtctgt ggctatgctt ctctggcact acgttgctta cagtgagaga     600
tacacattag atgtagagcc atactacaaa tcttgggagc cgattctcaa attgacgtcc     660
cgtcataact acggatggtc ttacattgtc tcttggatcg gaatcggatt tattgtcatc     720
ggaagtgctt tcatgttctt cgcctacgct gctgtaaaga gagaagagga ggacgcgctg     780
acagctaaac acggtgccta catgatgcca aactactatg acaaggggc tggaactatt     840
gtgccataca actacaacac gtacgctgga tatggtggct acccatatta caatcaatac     900
aacactgctg gctatggata catgacttat ggacgttaa                             939
```

<210> SEQ ID NO 37
<211> LENGTH: 23
<212> TYPE: DNA
<213> ORGANISM: V. carteri

<400> SEQUENCE: 37

```
atgcggatgg caatcgctgc ctt                                              23
```

<210> SEQ ID NO 38
<211> LENGTH: 19
<212> TYPE: DNA
<213> ORGANISM: V. carteri

<400> SEQUENCE: 38

```
tcacgctgcg ccaccggct                                                   19
```

```
<210> SEQ ID NO 39
<211> LENGTH: 39
<212> TYPE: DNA
<213> ORGANISM: C. reinhardtii

<400> SEQUENCE: 39
acggctcgag ggaagatcta gccatggcca agggcgagg                              39

<210> SEQ ID NO 40
<211> LENGTH: 28
<212> TYPE: DNA
<213> ORGANISM: C. reinhardtii

<400> SEQUENCE: 40
acggggatcc ttacttgtac agctcgtc                                         28

<210> SEQ ID NO 41
<211> LENGTH: 22
<212> TYPE: DNA
<213> ORGANISM: V. carteri

<400> SEQUENCE: 41
agatctatgc ggatggcaat cg                                               22

<210> SEQ ID NO 42
<211> LENGTH: 22
<212> TYPE: DNA
<213> ORGANISM: V. carteri

<400> SEQUENCE: 42
tggccatcgc tgcgccaccg gc                                               22

<210> SEQ ID NO 43
<211> LENGTH: 40
<212> TYPE: DNA
<213> ORGANISM: V. carteri

<400> SEQUENCE: 43
tggccatgga ggagccggag gagcccgctg cgccaccggc                            40

<210> SEQ ID NO 44
<211> LENGTH: 19
<212> TYPE: DNA
<213> ORGANISM: V. carteri

<400> SEQUENCE: 44
aacgacaagg ccgatgctg                                                   19

<210> SEQ ID NO 45
<211> LENGTH: 20
<212> TYPE: DNA
<213> ORGANISM: V. carteri

<400> SEQUENCE: 45
gcttgtggcc caggatgttg                                                  20

<210> SEQ ID NO 46
<211> LENGTH: 19
<212> TYPE: DNA
<213> ORGANISM: V. carteri

<400> SEQUENCE: 46
aaatggccag gtgagtcga                                                   19
```

```
<210> SEQ ID NO 47
<211> LENGTH: 20
<212> TYPE: DNA
<213> ORGANISM: V. carteri

<400> SEQUENCE: 47
gctggatgcg ggacttgttg                                              20

<210> SEQ ID NO 48
<211> LENGTH: 20
<212> TYPE: DNA
<213> ORGANISM: V. carteri

<400> SEQUENCE: 48
ggtatcgtgc tggactctgg                                              20

<210> SEQ ID NO 49
<211> LENGTH: 19
<212> TYPE: DNA
<213> ORGANISM: V. carteri

<400> SEQUENCE: 49
gggttaaaca gcacctcgg                                               19
```

ARTIFICIAL BIOLOGICAL MATERIALS PRODUCED BY SELF-ASSEMBLY OF PHOTOSYNTHETIC UNICELLS

CROSS REFERENCE TO RELATED APPLICATIONS

This application claims the benefit of U.S. Provisional Application No. 61/603,088 filed Feb. 24, 2012, the entire contents of which are incorporated herein by reference for all purposes. This patent is related to commonly owned U.S. patent application Ser. No. 13/408,722, entitled HETEROLOGOUS EXPRESSION OF CELLULAR ADHESION MOLECULES, which claims benefits of U.S. Provisional Application No. 61/448,135, filed Mar. 1, 2011, the entire contents of which are incorporated herein by reference for all purposes.

ACKNOWLEDGEMENT OF FEDERAL RESEARCH SUPPORT

This invention was made, in part, with government support awarded by the National Aeronautics and Space Agency, grant # NNG05165H, and by the United States Department of Agriculture, grant #2006-35318-17445. Accordingly, the United States government has certain rights in this invention.

SUBMISSION OF SEQUENCE LISTING

The Sequence Listing associated with this application is filed in electronic format via EFS-Web and is hereby incorporated by reference into the specification in its entirety.

BACKGROUND

All publications cited in this application are herein incorporated by reference.

Photosynthetic unicells comprise unicellular photosynthetic bacteria, unicellular members of the photosynthetic eukaryotes known as algae, and single cells derived from the green portions of plants. Unicells are single cells not physically attached to other cells. Unicells that are photosynthetic can produce complex and diverse organic compounds from carbon dioxide, inorganic salts, and water by means of photosynthesis.

Cell walls, also known as extracellular matrices, enclose nearly all naturally-occurring photosynthetic cells. They are chemically complex and their composition varies among different types of photosynthetic cells. In the case of multicellular photosynthetic organisms, chemical bonds between adjacent cell walls bind photosynthetic unicells together into multicellular photosynthetic organisms. Examples of cell walls include, but are not limited to, the peptidoglycan cell walls of cyanobacteria, the cellulosic cell walls of plants, heterokontophyte algae, and some green algae, the glycoprotein extracellular matrices of other green algae, the siliceous cell walls of diatoms, and the calcareous cell walls of coccolithophorids and coralline red algae.

All cell walls have a chemical composition that determines their physical properties. The chemical composition of cell walls is determined, in turn, by the specific organic and inorganic molecules secreted from the cells during biological development and by the order in which the various molecules are secreted. Cell wall molecules include but are not limited to polymers such as cellulose, glycoproteins such as collagen, and matrix materials such as pectins or alginic acid.

Many useful biological materials consist of, include, or are derived from the cell walls of photosynthetic organisms, including wood, paper, cotton, resins and glues, and cellophane. Similarly, useful biological materials are produced from the extracellular matrices of non-photosynthetic cells, including leather, catgut, sinew, horn, and medical collagen.

The foregoing examples of related art and limitations related therewith are intended to be illustrative and not exclusive, and they do not imply any limitations on the inventions described herein. Other limitations of the related art will become apparent to those skilled in the art upon a reading of the specification and a study of the drawings.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other improvements.

An embodiment of the present invention may comprise a method of self-assembly of photosynthetic unicells into a multicellular shape comprising: growing photosynthetic unicells expressing a cell adhesion protein; forming the photosynthetic unicells expressing a cell adhesion protein into a multicellular shape; inducing the expression of the cell adhesion protein in the photosynthetic unicells and producing a multicellular shape from the photosynthetic unicells.

An embodiment of the present invention may further comprise a DNA construct for expression of a cell adhesion protein in a photosynthetic unicell, wherein said DNA construct comprises one or more inducible promoters operably linked to a cell adhesion or cell wall protein coding sequence such that the DNA construct is expressed in response to external stimuli.

An embodiment of the present invention may further comprise a method for producing cell adhesion or cell wall proteins in the cell wall of a photosynthetic unicell which comprises growing a photosynthetic unicell having a DNA construct stably integrated into the genome of the photosynthetic unicell under conditions suitable for expression of the DNA construct in the cell wall of the photosynthetic unicell, wherein the DNA construct expresses a protein in said cell wall of said photosynthetic unicell, and wherein the expressed protein is a cell adhesion or cell wall protein.

An embodiment of the present invention may further comprise photosynthetic unicells genetically engineered for self-assembly of photosynthetic unicells into a multicellular shape.

In addition to the example, aspects and embodiments described above, further aspects and embodiments will become apparent by reference to the drawings and by study of the following descriptions, any one or all of which are within the embodiments of the invention. The summary above is a list of example implementations, not a limiting statement of the scope of the embodiments of the invention.

BRIEF DESCRIPTION OF THE FIGURES

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 1b is a second flow diagram showing a method of self-assembly of unicellular organisms into a multicellular shape.

BRIEF DESCRIPTION OF THE SEQUENCE LISTINGS

Figure 1A:
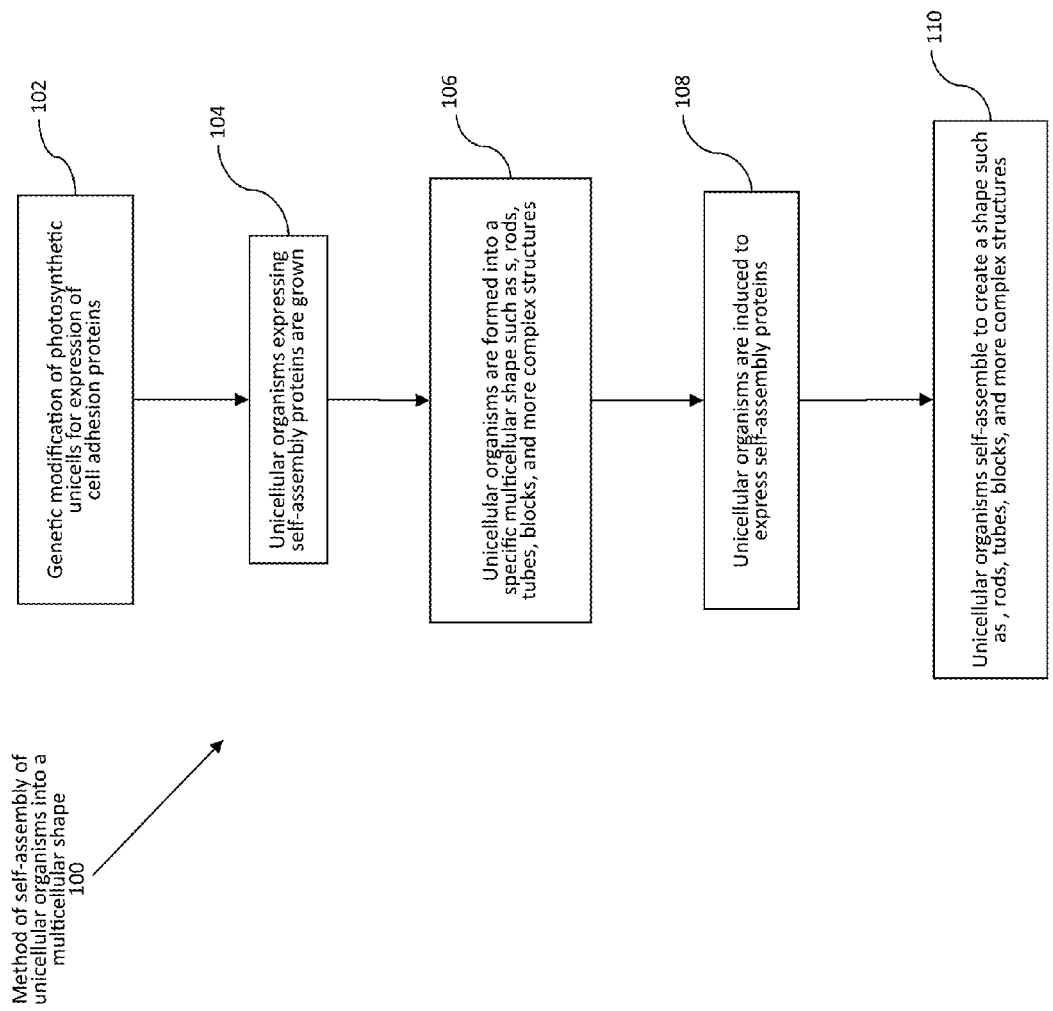
FIG. 1a is a flow diagram showing a method of self-assembly of unicellular organisms into a multicellular shape.

SEQ ID NO:1 discloses the nucleic acid sequence of the *Volvox* ISG transgene (GENBANK Accession No.: XM_002949857).

SEQ ID NO:2 discloses the protein sequence of the *Volvox* ISG transgene (GENBANK Accession No.: XP_002949903).

SEQ ID NO:3 discloses the nucleic acid sequence of the *Volvox* V1 extracellular matrix glycoprotein pherophorin transgene base pairs 10 to 1782 (GENBANK Accession No.: XM_002956879).

SEQ ID NO:4 discloses the protein sequence of the *Volvox* V1 extracellular matrix glycoprotein pherophorin transgene (GENBANK Accession No.: XP_002956925).

SEQ ID NO:5 discloses the nucleic acid sequence of the *Volvox* V2 extracellular matrix glycoprotein pherophorin transgene base pairs 21-1049 (GENBANK Accession No.: XM_002958810).

SEQ ID NO:6 discloses the protein sequence of the *Volvox* V2 transgene (GENBANK Accession No.: XP_002958856).

SEQ ID NO:7 discloses the nucleic acid sequence for HSP70A/RBCS2 promoter and intron 1.

SEQ ID NO:8 discloses the nucleic acid sequence for the complete plasmid with HSP70/RBCS2 promoter and intron 1 promoter, Algal-CAM protein and fluorescent protein plasmid pSI105.

SEQ ID NO:9 discloses the nucleic acid sequence for the PSAD promoter base pairs 1 to 820 (GENBANK Accession No.:AF335592).

SEQ ID NO:10 discloses the nucleic acid sequence for the forward primer 1 for the amplification of the PSAD promoter of SEQ ID NO:9.

SEQ ID NO:11 discloses the nucleic acid sequence for the reverse primer 1 for the amplification of the PSAD promoter of SEQ ID NO:9.

SEQ ID NO:12 discloses the nucleic acid sequence for the THI4 riboswitch alt. spliced exon with 5' NotI and 3' NdeI (GENBANK Accession No.:XM_001698619).

SEQ ID NO:13 discloses the nucleic acid sequence for the forward primer for the amplification of the THI4 riboswitch of SEQ ID NO:12.

SEQ ID NO:14 discloses the nucleic acid sequence for the reverse primer for the amplification of the THI4 riboswitch of SEQ ID NO:12.

SEQ ID NO:15 discloses the nucleic acid sequence for the forward primer with no overhang for the amplification of the THI4 riboswitch of SEQ ID NO:12.

SEQ ID NO:16 discloses the nucleic acid sequence for the reverse primer with no overhang for the amplification of the THI4 riboswitch of SEQ ID NO:12.

SEQ ID NO:17 discloses the nucleic acid sequence for the Algal-CAM signal peptide (GENBANK Accession number X80416).

SEQ ID NO:18 discloses the protein sequence for the Algal-CAM signal peptide (GENBANK Accession number CAA56621.1).

SEQ ID NO:19 discloses the nucleic acid sequence for the Algal-CAM cell adhesion molecule (GENBANK Accession number XM_002958317).

SEQ ID NO:20 discloses the protein sequence for the Algal-CAM cell adhesion molecule (GENBANK Accession number XP_002958363.1).

SEQ ID NO:21 discloses the nucleic acid sequence for the paromomycin resistance marker (aph VIIIsr) (GENBANK Accession number AF182845.2).

SEQ ID NO:22 discloses the nucleic acid sequence for the paromomycin resistance marker (aph VIIIsr) with upstream HSP70/RBCS2 promoter and intron 1.

SEQ ID NO:23 discloses the nucleic acid sequence for the human collagen protein type I, alpha 1 (COL1A1), base pairs 127-4521 (GENBANK Accession number NM_000088.3).

SEQ ID NO:24 discloses the protein sequence for the human collagen protein type I, alpha 1 (COL1A1), (GENBANK Accession number NP_000079).

SEQ ID NO:25 discloses the protein sequence for the *Drosophila melanogaster* integrin (GENBANK Accession number: CAA52155.1).

SEQ ID NO:26 disclosure the nucleic acid sequence for the *Drosophila melanogaster* alpha-PS1 mRNA base pairs 343-3783 (GENBANK Accession number: X73975.1).

SEQ ID NO:27 discloses the protein sequence for the *Homo sapiens* cadherin (GENBANK Accession number: CAA84586.1).

SEQ ID NO:28 discloses the nucleic acid sequence for the *Homo sapiens* cadherin gene, exon 3 and joined CDS base pairs 258 to 2743 (gi|515860:<15-238, gi|515861:15-158, gi|515858:15-170, gi|515862:15-159, gi|515866:15-190, gi|515867:15-143, gi|515868:15-197, gi|515841:15-259, gi|515847:15-160, gi|515848:15-239, gi|515855:15-242, gi|515856:15-145, gi|515857:15-158, gi|515859:15-224) (GENBANK Accession number: Z13009.1).

SEQ ID NO:29 discloses the protein sequence for the *Synechocystis* sp. PCC 6803 cadherin protein (NCBI Reference Sequence: NP_440434.1).

SEQ ID NO:30 discloses the nucleic acid sequence for the *Synechocystis* sp. PCC 6803 cadherin gene, exon 3 and joined CDS base pairs 587228-593125 (NCBI Reference Sequence: NC_000911.1).

SEQ ID NO:31 discloses the protein sequence for the *Homo sapiens* claudin 1 protein (GENBANK Accession number ABQ42705.1).

SEQ ID NO:32 discloses the nucleic acid sequence for the *Homo sapiens* claudin 1 gene (GENBANK Accession number EF564137.1).

SEQ ID NO:33 discloses the protein sequence for the *Mus musculus* claudin 5 protein (GENBANK Accession number AAH83341.1).

SEQ ID NO:34 discloses the nucleic acid sequence for the *Mus musculus* claudin 5 gene base pairs 140-796 (GENBANK Accession number BC083341.1).

SEQ ID NO:35 discloses the protein sequence for the *Caenorhabditis elegans* claudin protein F53B3.5 (GENBANK Accession number CCD61862.2).

SEQ ID NO:36 discloses the nucleic acid sequence for the *Caenorhabditis elegansclaudin* claudin gene (GENBANK Accession number F0080193.1 or NM_076098.6).

SEQ ID NO:37 discloses the nucleic acid sequence for the forward primer ACAMCDS2fwd.

SEQ ID NO:38 discloses the nucleic acid sequence for the reverse primer ACAMCDS2rev.

SEQ ID NO:39 discloses the nucleic acid sequence for the primer FwdxhoIBglII.

SEQ ID NO:40 discloses the nucleic acid sequence for the primer RevBamHI.

SEQ ID NO:41 discloses the nucleic acid sequence for the primer Fwdw/BglII.

SEQ ID NO:42 discloses the nucleic acid sequence for the primer Revw/MscI.

SEQ ID NO:43 discloses the nucleic acid sequence for the primer Revw/MscI and linker.

SEQ ID NO:44 discloses the nucleic acid sequence for the primer Scnfwd1.

SEQ ID NO:45 discloses the nucleic acid sequence for the primer Scnrev1.

SEQ ID NO:46 discloses the nucleic acid sequence for the primer ScnRTPCRfwd2.

SEQ ID NO:47 discloses the nucleic acid sequence for the primer ScnRTPCRrev2.

SEQ ID NO:48 discloses the nucleic acid sequence for the primer cActinfwd1.

SEQ ID NO:49 discloses the nucleic acid sequence for the primer cActinrev1.

Further, Applicant respectfully requests paragraphs [0142] to [0144] on pages 43 and 44 be amended as follows:

DETAILED DESCRIPTION

Embodiments of the present disclosure include methods for the self-assembly of photosynthetic unicells into multicellular shapes, such as sheets, boards, rods, tubes, blocks, and more complex structures. Embodiments of the present disclosure also include DNA constructs for the expression of a cell adhesion or cell wall protein coding sequence (such as the sequence for Algal-CAM, ISG, V1, V2, COL, claudin, cadherin, or integrin proteins), as well as methods for the integration of the DNA constructs into the genomes of photosynthetic unicells in order to facilitate the self-assembly of photosynthetic unicells into multicellular shapes. Proteins expressed by the DNA constructs to cause self-assembly of photosynthetic unicells include but are not limited to cell adhesion molecules, other cell wall proteins, cytoskeleton proteins, motor proteins, proteins that govern production and secretion of cell wall materials by the cellular endomembrane system, and proteins associated with the plasma membrane that contribute to shape of the photosynthetic unicells or the composition of their cell walls. Constructs used to cause self-assembly are artificially constructed segments of DNA that may be introduced into the target photosynthetic unicells and integrated into their genomes. The expressed proteins are those that cause self-assembly of photosynthetic unicells into novel and useful multicellular structures and/or novel and useful biological materials.

As used herein, the term "expression" includes the process by which information from a gene is used in the synthesis of a functional gene product, such as the expression of a cell adhesion proteins or cell wall proteins in the cell wall of unicellular organisms.

As will be discussed further in FIGS. 1-16, embodiments of the present disclosure provide methods for the self-assembly of photosynthetic unicells into a multicellular shape. These methods include but are not limited to growing photosynthetic unicells expressing a cell adhesion proteins or cell wall proteins; growing or forming the photosynthetic unicells expressing a cell adhesion protein or cell wall protein into a multicellular shape; inducing the expression of the cell adhesion protein in the photosynthetic unicells and producing an artificial multicellular shape from the photosynthetic unicells.

Embodiments of the present disclosure further include approaches and methods for the expression of cell adhesion proteins or cell wall proteins in photosynthetic unicells. As used herein, photosynthetic unicells include unicellular photosynthetic prokaryotes, unicellular members of the photosynthetic protistan eukaryotes known collectively as algae, and single cells derived from the green portions of plants. DNA constructs and methods for integration of the DNA constructs into the genomes of photosynthetic unicells to allow for the expression of cell adhesion or cell wall proteins in photosynthetic unicells are also included in the present disclosure.

Embodiments of the present disclosure further include approaches for the expression of human collagens and/or other heterologous extra-cellular matrix proteins of animal origin in photosynthetic unicells. DNA constructs as well as methods for integration of the DNA constructs into the genomes of photosynthetic unicells to allow for the expression of human collagens and/or other extra-cellular matrix proteins of animal origin are also included in the present disclosure.

Embodiments of the present disclosure further include one or more DNA constructs for use in expression of cell wall proteins in photosynthetic unicells represented by CP-Ribo-ISG-FP-X and variations thereof, where at least one constitutive and/or inducible promoter is operably linked to at least one translational regulator. The promoter and regulator sequences are operably linked to a development-specific cell wall glycoprotein coding sequence that is operably linked to a fluorescent peptide marker or selectable marker that is operably linked to a transcription terminator sequence. The DNA construct is stably integrated into a photosynthetic unicell and organisms expressing the development-specific cell wall protein are then generated. The photosynthetic unicells containing the DNA construct may then be formed into and induced to adhere into a multicellular shape. One or more of the embodiments of the photosynthetic unicells are unicellular green algae and unicellular chromalveolate algae such as diatoms or members of family Eustigmataceae.

Embodiments of the present disclosure further include one or more DNA constructs for use in the expression of cell wall proteins in photosynthetic unicells represented by CP-Ribo-V1-FP-X and variations thereof, and at least one constitutive and/or inducible promoter operably linked to at least one translational regulator. The inducible promoter is operably linked to a coding sequence for an HRGP extensin-related protein (such as the V1 *Volvox* protein) that is operably linked to a fluorescent peptide marker that is operably linked to a transcription terminator sequence. Additional variations of this DNA construct may include CP-Ribo-V2-FP-X. The DNA construct is stably integrated into a photosynthetic unicell and organisms expressing the HRGP extensin-related protein cell wall protein are then generated. The photosynthetic unicells containing the DNA construct may then be formed into and induced to adhere into a multicellular shape. One or more of the embodiments of the photosynthetic unicells are unicellular green algae and unicellular chromalveolate algae such as diatoms or members of family Eustigmataceae.

Embodiments of the present disclosure include one or more DNA constructs for use in expression of cell adhesion molecules in the cell walls of photosynthetic unicells represented by CP-Ribo-COL-FP-X and variations thereof, and at least one constitutive promoter operably linked to at least one inducible promoter. The inducible promoter is operably linked to a human type 1 collagen protein coding sequence that is operably linked to a fluorescent peptide marker that is operably linked to a transcription terminator sequence. Transgenic unicellular organisms expressing the human collagen proteins are then generated. The photosynthetic unicells containing the DNA construct may then be formed into and induced to adhere into a multicellular shape. As used herein, "transgenic" is used to indicate a unicellular organism, which has been genetically modified to contain the DNA constructs. One or more embodiments of the photosynthetic unicells are unicellular green algae and unicellular chromalveolate algae such as diatoms or members of family Eustigmataceae.

Embodiments of the present disclosure further include one or more DNA constructs for use in the expression of cell wall proteins in photosynthetic unicells represented by SM-CP-Ribo-ISG-X and variations thereof, and at least one selectable marker operably linked to at least one constitutive and/or inducible promoter, which is operably linked to at least one translational regulator. The promoter and regulator sequences are operably linked to a development-specific cell wall glycoprotein coding sequence that is operably linked to a transcription terminator sequence. The DNA construct is stably integrated into a photosynthetic unicell and organisms expressing the development-specific cell wall protein are then generated. The photosynthetic unicells containing the DNA construct may then be formed into and induced to adhere into a multicellular shape. One or more embodiments of the photosynthetic unicells are unicellular green algae and unicellular chromalveolate algae such as diatoms or members of family Eustigmataceae.

Embodiments of the present disclosure further include one or more DNA constructs for use in the expression of cell wall proteins in photosynthetic unicells represented by Pro-IP-ISG-DRR and variations thereof, where at least one constitutive and/or inducible promoter is operably linked to at least one development-specific cell wall glycoprotein coding sequence. The development-specific cell wall glycoprotein coding sequence is operably linked to a downstream regulator region. The DNA construct is stably integrated into a photosynthetic unicell and organisms expressing the development-specific cell wall protein are then generated. The photosynthetic unicells containing the DNA construct may then be formed into and induced to adhere into a multicellular shape. One or more embodiments of the photosynthetic unicells are unicellular green algae and unicellular chromalveolate algae such as diatoms or members of family Eustigmataceae.

Embodiments of the present disclosure further include one or more DNA constructs for use in the expression of cell wall proteins in photosynthetic unicells represented by Pro-IP-V1-DRR and variations thereof, where at least one constitutive and/or inducible promoter is operably linked to at least one HRGP extensin-related protein coding sequence. The HRGP extensin-related protein coding sequence is operably linked to a downstream regulator region. The DNA construct is stably integrated into a photosynthetic unicell and organisms expressing the development-specific cell wall protein are then generated. The photosynthetic unicells containing the DNA construct may then be formed into and induced to adhere into a multicellular shape. One or more embodiments of the photosynthetic unicells are unicellular green algae and unicellular chromalveolate algae such as diatoms or members of family Eustigmataceae.

Embodiments of the present disclosure further include one or more DNA constructs for use in the expression of cell wall proteins in photosynthetic unicells represented by Pro-IP-V2-DRR and variations thereof, where at least one constitutive and/or inducible promoter is operably linked to at least one HRGP extensin-related protein coding sequence. The HRGP extensin-related protein coding sequence is operably linked to a downstream regulator region. The DNA construct is stably integrated into a photosynthetic unicell and organisms expressing the development-specific cell wall protein are then generated. The photosynthetic unicells containing the DNA construct may then be formed into and induced to adhere into a multicellular shape. One or more embodiments of the photosynthetic unicells are unicellular green algae and unicellular chromalveolate algae such as diatoms or members of family Eustigmataceae.

Embodiments of the present disclosure further include one or more DNA constructs for use in the expression of cell wall proteins in photosynthetic unicells represented by Pro-IP-Cadherin-DRR and variations thereof, where at least one constitutive and/or inducible promoter is operably linked to at least one cadherin protein coding sequence. The cadherin protein coding sequence is operably linked to a downstream regulator region. The DNA construct is stably integrated into a photosynthetic unicell and organisms expressing the development-specific cell wall protein are then generated. The photosynthetic unicells containing the DNA construct may then be formed into and induced to adhere into a multicellular shape. One or more embodiments of the photosynthetic unicells are unicellular green algae and unicellular chromalveolate algae such as diatoms or members of family Eustigmataceae.

Embodiments of the present disclosure further include one or more DNA constructs for use in the expression of cell wall proteins in photosynthetic unicells represented by Pro-IP-Claudin-DRR and variations thereof, where at least one constitutive and/or inducible promoter is operably linked to at least one claudin protein coding sequence. The claudin protein coding sequence is operably linked to a downstream regulator region. The DNA construct is stably integrated into a photosynthetic unicell and organisms expressing the development-specific cell wall protein are then generated. The photosynthetic unicells containing the DNA construct may then be formed into and induced to adhere into a multicellular shape. One or more embodiments of the photosynthetic unicells are unicellular green algae and unicellular chromalveolate algae such as diatoms or members of family Eustigmataceae.

Embodiments of the present disclosure further include one or more DNA constructs for use in the expression of cell wall proteins in photosynthetic unicells represented by Pro-IP-Integrin-DRR and variations thereof, where at least one constitutive and/or inducible promoter is operably linked to at least one integrin protein coding sequence. The integrin protein coding sequence is operably linked to a downstream regulator region. The DNA construct is stably integrated into a photosynthetic unicell and organisms expressing the development-specific cell wall protein are then generated. The photosynthetic unicells containing the DNA construct may then be formed into and induced to adhere into a multicellular shape. One or more embodiments of the photosynthetic unicells are unicellular green algae and unicellular chromalveolate algae such as diatoms or members of family Eustigmataceae.

As previously discussed an embodiment of the present disclosure provides photosynthetic unicells having the DNA construct stably integrated into their genome under conditions suitable for an expression of the DNA construct where the photosynthetic unicells are grown to adhere together into said specific multicellular shape. These shapes may include but are not limited to sheets, boards, rods, tubes, blocks, and more complex structures. As shown in FIG. 1, a method of self-assembly of unicellular organisms into a multicellular shape is provided. In step 102, photosynthetic unicells are genetically modified to allow for expression of cell adhesion proteins in the cell wall of the photosynthetic unicells. In step 104, unicellular organisms expressing self-assembly proteins are grown, including but not limited to *Chlamydomonas reinhardtii* and organisms cyanobacteria including but not limited to *Arthrospira* spp., *Spirulina* spp., *Synechococcus elongatus* 7942, *Synechococcus* spp., *Synechosystis* spp. PCC 6803, *Synechosystis* spp., and *Spirulina plantensis*, *Calothrix* spp., *Anabaena flos-aquae*, *Aphanizomenon* spp., *Anabaena* spp., *Gleotrichia* spp., *Oscillatoria* spp. and *Nostoc* spp.; eukaryotic unicellular algae such as but not limited to *Chaetoceros* spp., *Chlamydomonas reinhardtii*, *Chlamydomonas* spp., *Chlorella vulgaris*, *Chlorella* spp., *Cyclotella* spp., *Didymosphenia* spp., *Dunaliella tertiolecta*, *Dunaliella* spp., *Botryococcus braunii*, *Botryococcus* spp., *Gelidium* spp., *Gracilaria* spp., *Hantzschia* spp., *Hematococcus* spp., *Isochrysis* spp., *Laminaria* spp., *Nannochloropsis* spp., *Navicula* spp., *Nereocystis luetkeana*, *Pleurochrysis* spp., *Postelsia palmaeformis*, and *Sargassum* spp. As will be discussed in more detail later, these self-assembly proteins may be cell adhesion or cell wall proteins such as such as the Algal-CAM, V1, V2, claudin, cadherin, integrin, human collagen or ISG proteins. In step 106, a plurality of unicellular organisms are formed into a specific multicellular shape such as sheets, boards, rods, tubes, blocks, and more complex structures. In step 108, unicellular organisms are induced to express self-assembly proteins, such as cell adhesion or cell wall proteins, through a variety of mechanisms which are known in the art. Examples of mechanisms to induce expression of self-assembly proteins may include but are not limited to removal of ammonium from the growth medium where the photosynthetic unicells are grown so as to induce activity of the NIT1 inducible promoter contained in the constructs stably integrated into a genome of the photosynthetic unicells (as will be discussed later) or removal of thiamine from the growth medium where the photosynthetic unicells are grown so as to activate translation controlled by the THI4 translational regulator contained in the constructs stably integrated into a genome of the photosynthetic unicells (as will be discussed later). In step 110 unicellular organisms self-assemble to create a shape such as but not limited to sheets, boards, rods, tubes, blocks, and more complex structures.

As shown in FIG. 1b, a second flow diagram showing a method of self-assembly of unicellular organisms into a multicellular shape is provided. In step 102b, free swimming photosynthetic unicells, such as *Chlamydomonas reinhardtii* are identified. In step 104b the photosynthetic unicells are genetically modified to allow for expression of cell adhesion or cell wall proteins in the cell wall of the photosynthetic unicells. In step 106b, the photosynthetic unicells expressing self-assembly proteins are formed into a specific multicellular shape. To form the photosynthetic unicells in a specific multicellular shape, additional structures or forms may be used including but not limited to scaffolds, wire frames, screens or boards. In step 108b, unicellular organisms are induced to express self-assembly proteins and causing the photosynthetic unicells to adhere together to form an artificial shape such as but not limited to sheets, boards, rods, tubes, blocks, and more complex structures.

Figure 2:
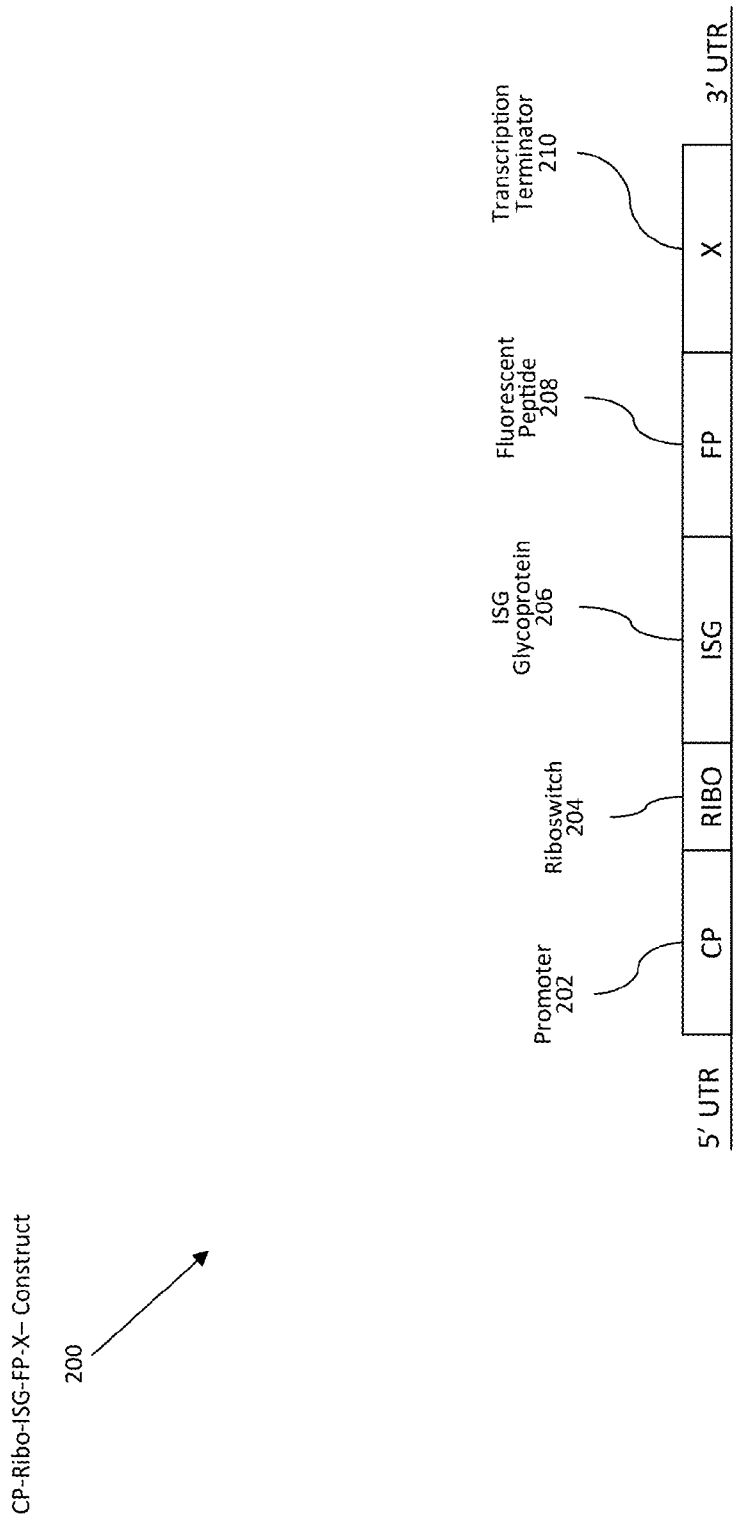
FIG. 2 is a map of a DNA construct, represented as CP-Ribo-ISG-FP-X that includes (from 5' to 3') a constitutive and/or inducible promoter, a translational regulator, a development-specific glycoprotein coding sequence, a fluorescent peptide tag coding sequence, and a downstream regulatory region including transcription terminator sequence.

As shown in FIG. 2, a construct generally represented as CP-Ribo-ISG-FP-X 200, wherein CP is a PSAD (SEQ ID NO:9 with a forward primer of SEQ ID NO:10 and reverse primer SEQ ID NO:11) or HSP70A/RBCS2 (SEQ ID NO:7) constitutive and/or inducible promoter with a SacI restriction site on the 5' end 202. Ribo is a riboswitch translational regulator with a NotI restriction site on the 5' end (SEQ ID NO:12 with a forward primer SEQ ID NO:14 and reverse primer SEQ ID NO:15) 204. ISG is an inversion-specific glycoprotein coding sequence with a start codon of ATG and a restriction site of NdeI at the 5' end of the ISG sequence (such as SEQ ID NO:1 and SEQ ID NO:2) 206. FP is a peptide marker sequence, such as a fluorescent protein region that may include a flexible linker sequence on the 5' end of the fluorescent peptide coding sequence 208 and X is a downstream regulatory region including the stop codon TAG and the transcription terminator sequence 210. Each of these components is operably linked to the next, i.e., the PSAD or HSP70A/RBCS2 promoter is operably linked to the 5' end of the riboswitch coding sequence, the riboswitch is operably linked to the ISG sequence encoding the ISG glycoprotein, the ISG glycoprotein coding sequence is operably linked to the 5' end of the fluorescent protein coding sequence and the fluorescent protein coding sequence is operably linked to 5' end of the termination coding sequence. The ISG glycoprotein may also be expressed in variations of the construct of FIG. 2 including but not limited to CP-Ribo-ISG-X or SM-CP-Ribo-ISG-X where SM is a selectable marker (such as SEQ ID NO:21 or SEQ ID NO: 22). One example of an expression vector is the *Chlamydomonas* expression vector designated pSI105, or a derivative of this vector, in the case of expression in the unicellular green algal genus *Chlamydomonas* or other green algae. The DNA construct CP-Ribo-ISG-FP-X is then integrated into a unicellular photosynthetic organism such as *Chlamydomonas reinhardtii* and organisms expressing the cell adhesion protein, including expression in the cell wall or extracellular matrix of the organism, are then generated. The photosynthetic unicells containing the DNA construct may then be formed into and induced to adhere into a multicellular shape.

Figure 3:
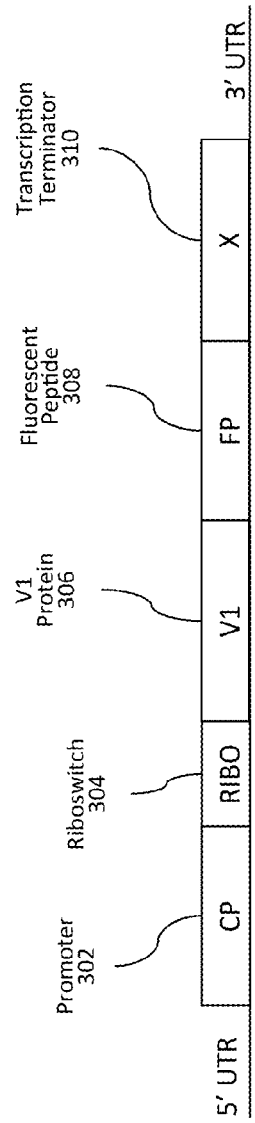
FIG. 3 is a map of a DNA construct, represented as CP-Ribo-V1-FP-X that includes (from 5' to 3') a constitutive and/or inducible promoter, a translational regulator, a wound-healing protein coding sequence, a fluorescent peptide tag coding sequence, and a downstream regulatory region including transcription terminator sequence.

In FIG. 3, a construct generally represented as CP-Ribo-V1-FP-X 300, wherein CP is a constitutive and/or inducible promoter such as PSAD (SEQ ID NO:9 with a forward primer SEQ ID NO:10 and reverse primer SEQ ID NO:11) or HSP70A/RBCS2 (SEQ ID NO:7) promoter with a SacI restriction site on the 5' end of the promoter sequence 302. Ribo is a riboswitch translational regulator with a NotI restriction site on the 5' end of the sequence (SEQ ID NO:12 with a forward primer SEQ ID NO:14 and reverse primer SEQ ID NO:15) 304. V1 (such as SEQ ID NO:3 and SEQ ID NO:4) is an extracellular HRGP extensin-related protein coding sequence with a start codon of ATG and a restriction site of NdeI at the 5' end of the V1 coding sequence 306 FP is a peptide marker sequence such as a fluorescent protein region that may include a flexible linker sequence on the 5' end of the fluorescent peptide coding sequence 308 and X is a downstream regulatory region including the stop codon TAG and the transcription terminator sequence 310. Each of these components is operably linked to the next, i.e., the PSAD or HSP70A/RBCS2 promoter is operably linked to the 5' end of the riboswitch coding sequence, the riboswitch is operably linked to the V1 sequence encoding the V1 protein, the V1 protein coding sequence is operably linked to the 5' end of the fluorescent peptide coding sequence and the fluorescent peptide coding sequence is operably linked to 5' end of the termination coding sequence. The V1 protein may also be expressed in variations of the construct of FIG. 3 including but not limited to CP-Ribo-V1-X or SM-CP-Ribo-V1-X where SM is a selectable marker (such as SEQ ID NO:21 or SEQ ID NO: 22). One example of an expression vector is the *Chlamydomonas* expression vector designated pSI105, or a derivative of this vector, in the case of expression in unicellular green algal genus *Chlamydomonas* or other green algae. The DNA construct CP-Ribo-V1-FP-X is then integrated into a photosynthetic unicell such as *Chlamydomonas* reinhardtii and organisms expressing the cell adhesion protein, including expression in the cell wall or extracellular matrix of the organism, are then generated. The photosynthetic unicells containing the DNA construct may then be formed into and induced to adhere into a multicellular shape.

Figure 4:
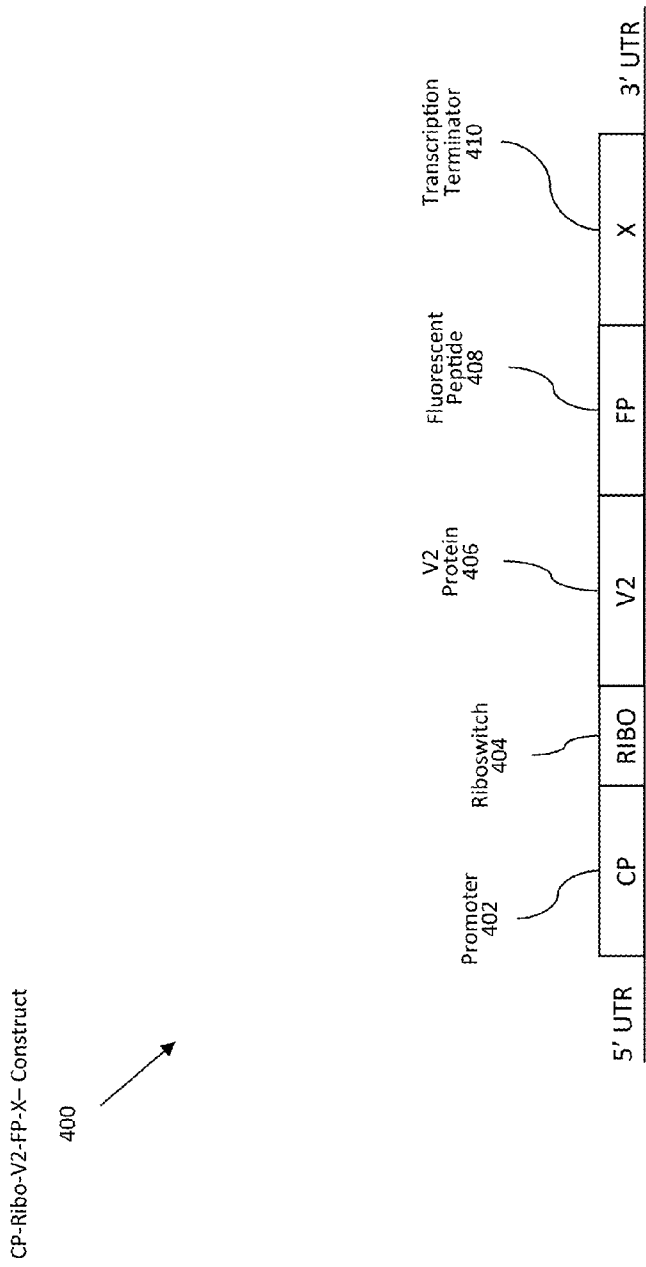
FIG. 4 is a map of a DNA construct, represented as CP-Ribo-V2-FP-X that includes (from 5' to 3') a constitutive and/or inducible promoter, a translational regulator, a wound-healing protein coding sequence, a fluorescent peptide tag coding sequence, and a downstream regulatory region including transcription terminator sequence.

In FIG. 4, a construct is generally represented as CP-Ribo-V2-FP-X 400 wherein CP is a constitutive and/or inducible promoter such as PSAD (SEQ ID NO:9 with a forward primer SEQ ID NO:10 and reverse primer SEQ ID NO:11) or HSP70A/RBCS2 (SEQ ID NO:7) with a SacI restriction site on the 5' end 402. Ribo is a riboswitch translational regulator with a NotI restriction site on the 5' end of the inducible promoter sequence (SEQ ID NO:12 with a forward primer SEQ ID NO:14 and reverse primer SEQ ID NO:15) 404. V2 (such as SEQ ID NO:5 or SEQ ID NO:6) is an extracellular HRGP extensin-related protein coding sequence with a start codon of ATG and a restriction site of NdeI at the 5' end of the V2 coding sequence 406. FP is a peptide marker sequence such as a fluorescent protein region that may include a flexible linker sequence on the 5' end of the fluorescent peptide coding sequence 408 and X is a downstream regulatory region including the stop codon (TAG) and the transcription terminator sequence 410. Each of these components is operably linked to the next, i.e., the PSAD or HSP70A/RBCS2 promoter is operably linked to the 5' end of the riboswitch coding sequence, the riboswitch coding sequence is operably linked to the V2 sequence encoding the V2 protein, the V2 protein coding sequence is operably linked to the 5' end of the fluorescent peptide coding sequence and the fluorescent protein coding sequence is operably linked to 5' end of the termination coding sequence. The V2 protein may also be expressed in variations of the construct of FIG. 4 including but not limited to CP-Ribo-V2-X or SM-CP-Ribo-V2-X where SM is a selectable marker (such as SEQ ID NO:21 or SEQ ID NO: 22). One example of an expression vector is the *Chlamydomonas* expression vector designated pSI105, or a derivative of this vector, in the case of expression in unicellular green algal genus *Chlamydomonas* or other green algae. The DNA construct CP-Ribo-V2-FP-X is then integrated into a photosynthetic unicell such as *Chlamydomonas reinhardtii* and organisms expressing the cell adhesion protein, including expression in the cell wall or extracellular matrix of the organism, are then generated. The photosynthetic unicells containing the DNA construct may then be formed into and induced to adhere into a multicellular shape.

Figure 5:
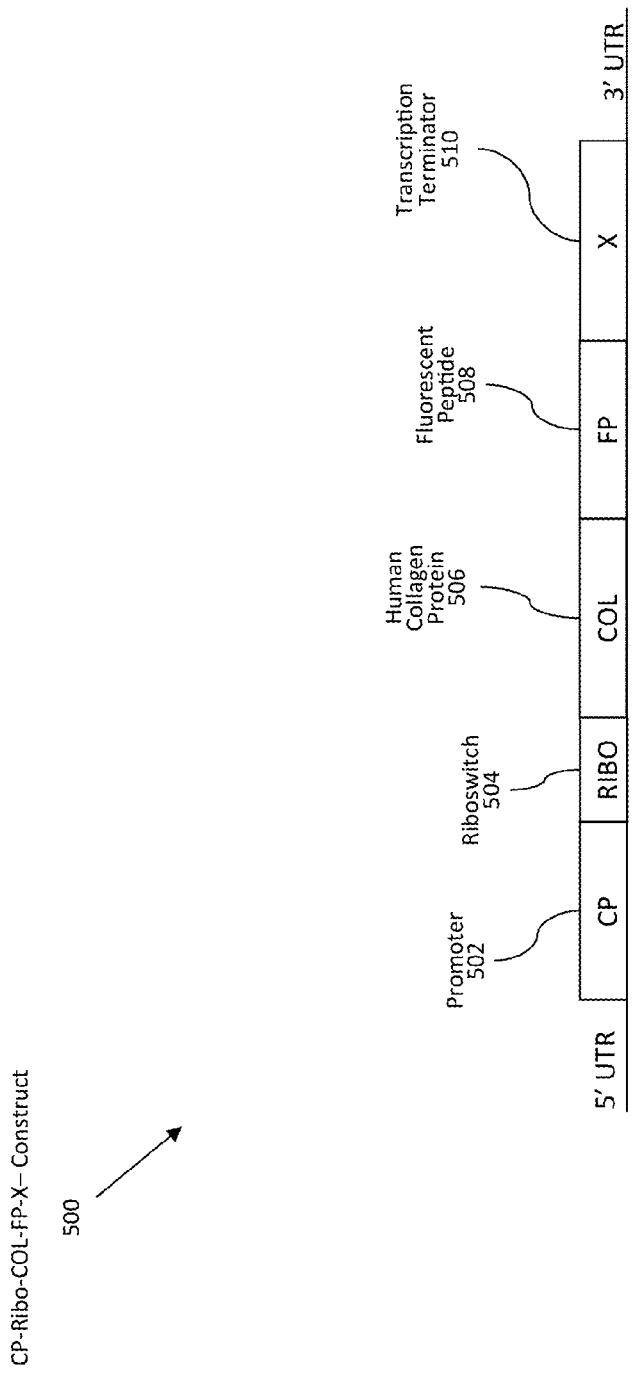
FIG. 5 is a map of a DNA construct, represented as CP-Ribo-COL-FP-X that includes (from 5' to 3') a constitutive and/or inducible promoter, a translational regulator, a protein coding sequence for a cell adhesion molecule of animal origin, a fluorescent peptide tag coding sequence, and a downstream regulatory region including transcription terminator sequence.

In FIG. 5, a construct is generally represented as CP-Ribo-COL-FP-X 500 wherein CP is a constitutive and/or inducible promoter such as PSAD (SEQ ID NO:9 with a forward primer SEQ ID NO:10 and reverse primer SEQ ID NO:11) or HSP70A/RBCS2 (SEQ ID NO:7) with a SacI restriction site on the 5' end 502. Ribo is a riboswitch translational regulator with a NotI restriction site on the 5' end of the inducible promoter sequence (SEQ ID NO:12 with a forward primer SEQ ID NO:14 and reverse primer SEQ ID NO:15) 504. COL is a human collagen protein coding sequence (SEQ ID NO:23 or SEQ ID NO:24) with a start codon of ATG, a signal peptide sequence appropriate for secretion, and a restriction site of NdeI at the 5' end 506. FP is a peptide marker sequence such as a fluorescent protein region that may include a flexible linker sequence on the 5' end of the fluorescent peptide coding sequence 508 and X is a downstream regulatory region including the stop codon TAG and the transcription terminator sequence 510. Each of these components is operably linked to the next, i.e., the PSAD or HSP70A/RBCS2 promoter is operably linked to the 5' end of the riboswitch regulator coding sequence, the riboswitch regulator is operably linked to the human collagen sequence encoding the human collagen protein, the human collagen coding sequence is operably linked to the 5' end of the fluorescent peptide coding sequence and the fluorescent peptide coding sequence is operably linked to 5' end of the termination coding sequence. The collagen protein may also be expressed in variations of the construct of FIG. 5 including but not limited to CP-Ribo-COL-X or SM-CP-Ribo-COL-X where SM is a selectable marker (such as SEQ ID NO:21 or SEQ ID NO:22). One example of an expression vector is the *Chlamydomonas* expression vector designated pSI105, or a derivative of this vector, in the case of expression in unicellular green algal genus *Chlamydomonas* or other green algae. The DNA construct CP-Ribo-COL-FP-X is then integrated into a photosynthetic unicell such as *Chlamydomonas reinhardtii* and organisms expressing the cell adhesion protein, including expression in the cell wall or extracellular matrix of the organism, are then generated. The photosynthetic unicells containing the DNA construct may then be formed into and induced to adhere into a multicellular shape.

Figure 6:
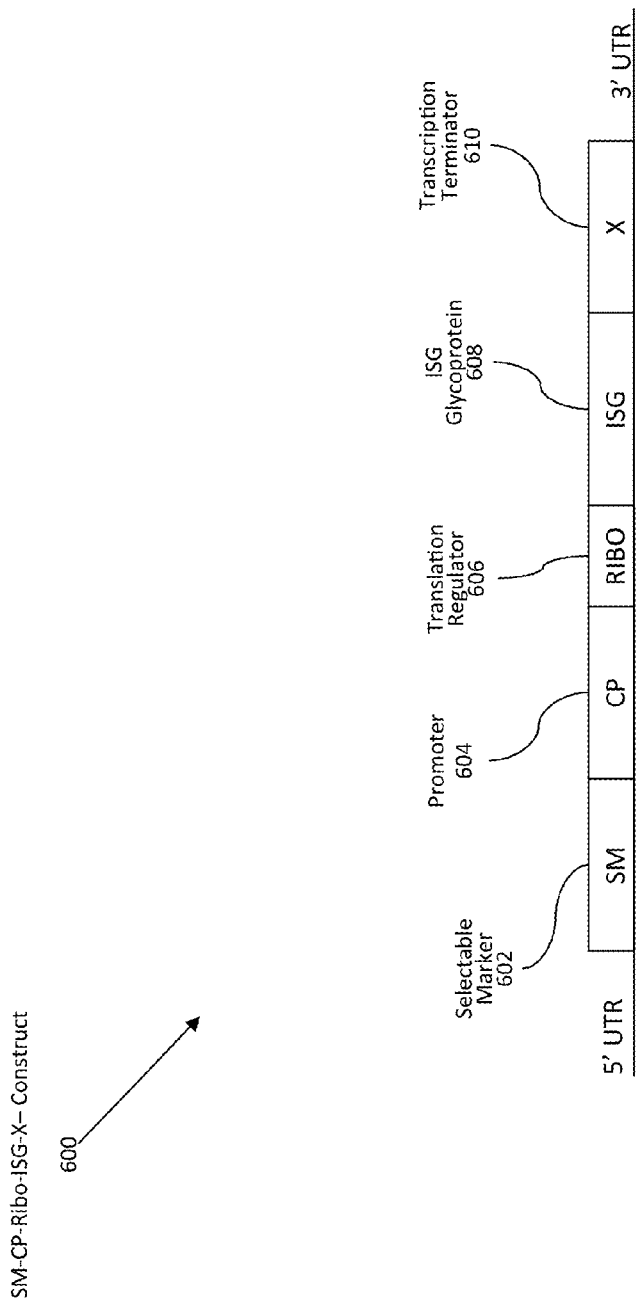
FIG. 6 is a map of a DNA construct, represented as SM-CP-Ribo-ISG-X that includes (from 5' to 3') a selectable marker, a constitutive and/or inducible promoter, a translational regulator, a development-specific glycoprotein coding sequence, and a downstream regulatory region including transcription terminator sequence.

As shown in FIG. 6, a construct is generally represented as SM-CP-Ribo-ISG-X 600, where SM is a selectable marker such as a paromomycin resistance marker (aph VIIIsr) (such as SEQ ID NO:21 or SEQ ID NO:22) 602. CP is a PSAD or HSP70A/RBCS2 constitutive and/or inducible promoter with a SacI restriction site on the 5' end 604. Ribo is a riboswitch translational regulator with a NotI restriction site on the 5' end 606. ISG is an inversion-specific glycoprotein coding sequence with a start codon of ATG and a restriction site of NdeI at the 5' end of the ISG sequence 608. X is a downstream regulatory region including the stop codon TAG and the transcription terminator sequence 610. Each of these components is operably linked to the next, i.e., the aph VIIIsr selectable marker is operably linked to the PSAD or HSP70A/RBCS2 promoter. The PSAD or HSP70A/RBCS2 promoter is operably linked to the 5' end of the riboswitch coding sequence, the riboswitch is operably linked to the ISG sequence encoding the ISG glycoprotein, the ISG glycoprotein coding sequence is operably linked to the 5' end of the termination coding sequence. One example of an expression vector is the *Chlamydomonas* expression vector designated pSI105, or a derivative of this vector, in the case of expression in the unicellular green algal genus *Chlamydomonas* or other green algae. The DNA construct as SM-CP-Ribo-ISG-X is then integrated into a photosynthetic unicell such as *Chlamydomonas reinhardtii* and organisms expressing the cell adhesion protein, including expression in the cell wall or extracellular matrix of the organism, are then generated. The photosynthetic unicells containing the DNA construct may then be formed into and induced to adhere into a multicellular shape.

Figure 7:
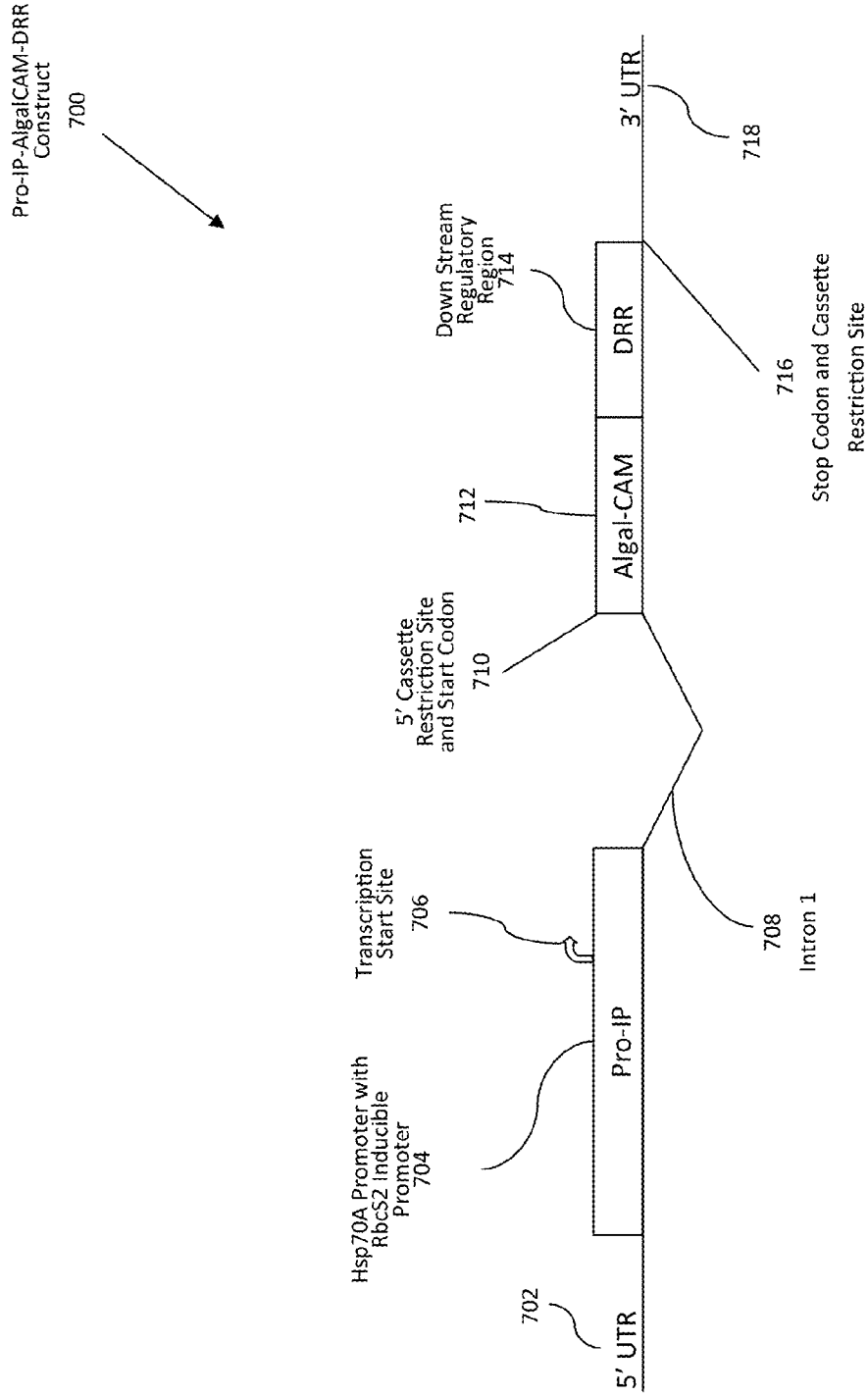
FIG. 7 is a map of a DNA construct, represented as Pro-IP-AlgalCAM-DRR that includes (from 5' to 3'), a promoter with an inducible promoter, the Algal-CAM protein coding sequence, and a downstream regulatory region.

As shown in FIG. 7, a construct is generally represented as Pro-IP-AlgalCAM-DRR 700, where on the 5' UTR end 702 Pro-IP 704 is a promoter with an inducible promoter such as the RBCS2 promoter flanked by enhancer elements of HSP70A and RBCS2 intron 1 (SEQ ID NO:7, SEQ ID NO:9 or SEQ ID NO:8 which contains the nucleic acid sequence for the complete plasmid with HSP70/RBCS2 promoter and intron 1 promoter, Algal-CAM protein and fluorescent protein plasmid pSI105) with an intron sequence coding sequence, Intron 1,708 on the 3' end as well as a SacI restriction site on the 5' end with a transcription start site 706. AlgalCAM 712 is the Algal-CAM cell adhesion protein coding sequence (such as SEQ ID NO:17, SEQ ID NO:18, SEQ ID NO:19 or SEQ ID NO:20) with a restriction site and start codon 610 on the 5' end of the Algal-CAM protein coding sequence. The downstream regulatory region DRR 714 includes the transcription terminator sequence as well as the stop codon and 3' cassette restriction site 716 on the 3'UTR end 718. The downstream regulatory region may include a peptide tag such as the FLAG 3× tag. A selectable marker such as a paromomycin resistance marker (aph VIIIsr) (such as SEQ ID NO:21 or SEQ ID NO:22) may also be used in the construct. Each of these components is operably linked to the next, i.e., the HSP70A/RBCS2 promoter with the Intron 1 sequence is operably linked to the 5' end of the Algal-CAM cell adhesion protein coding sequence encoding the cell adhesion protein. The cell adhesion protein coding sequence is operably linked to the 5' end of the downstream regulatory region. The DNA construct Pro-IP-AlgalCAM-DRR is then integrated into a photosynthetic unicell such as *Chlamydomonas reinhardtii* and organisms expressing the cell adhesion protein are then generated. The photosynthetic unicells containing the DNA construct may then be formed into and induced to adhere into a multicellular shape.

Figure 8:
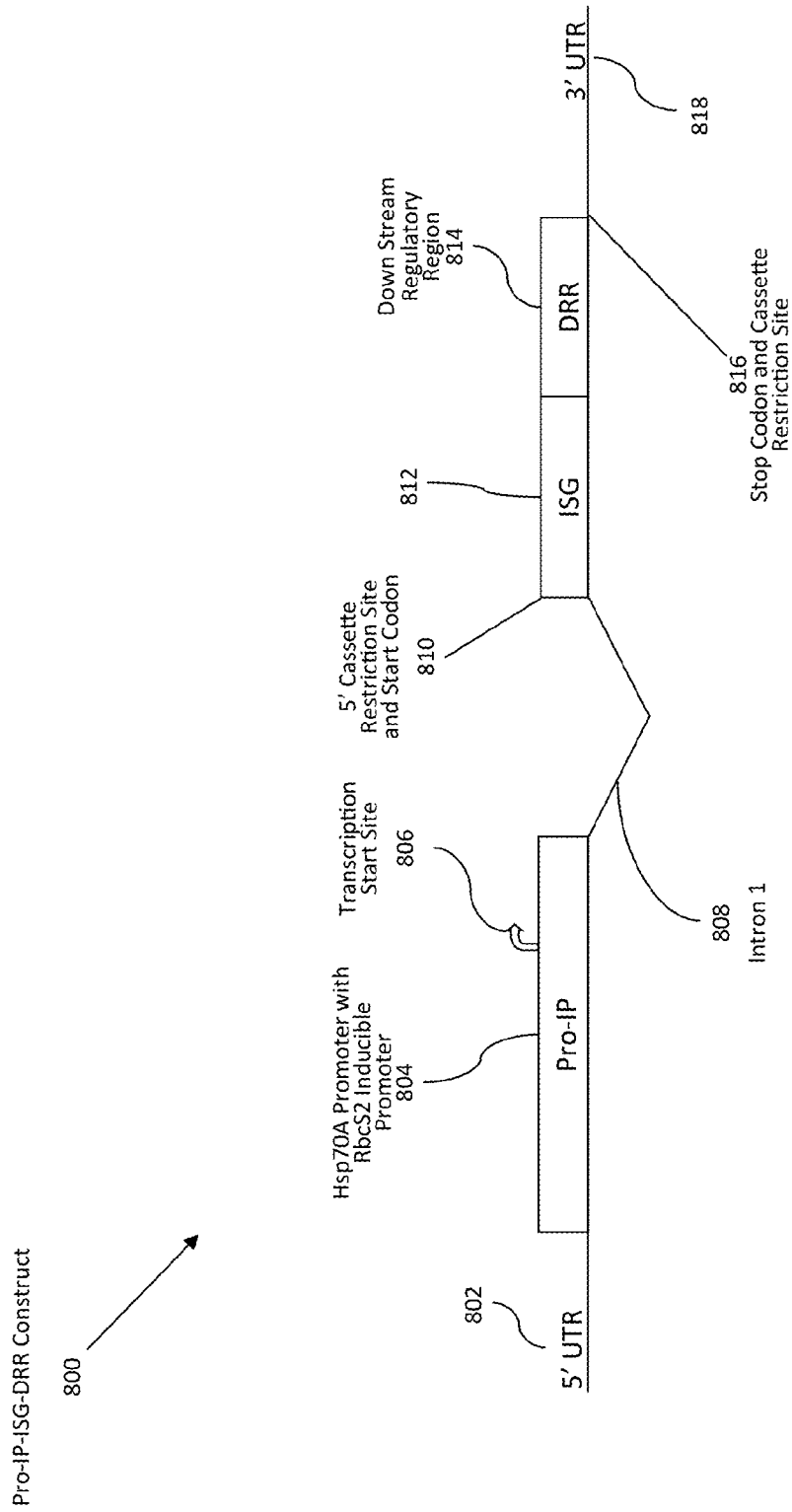
FIG. 8 is a map of a DNA construct, represented as Pro-IP-ISG-DRR that includes (from 5' to 3'), a promoter with an inducible promoter, the ISG protein coding sequence, and a downstream regulatory region.

As shown in FIG. 8, a construct is generally represented as Pro-IP-ISG-DRR 800, where on the 5' UTR end 802 Pro-IP 704 is a promoter with an inducible promoter such as the RBCS2 promoter flanked by enhancer elements of HSP70A and RBCS2 intron 1 (SEQ ID NO:9) with an intron sequence coding sequence, Intron 1, 808 on the 3' end as well as a SacI restriction site on the 5' end with a transcription start site 806. ISG (SEQ ID NO:1 or SEQ ID NO:2) 812 is an inversion-specific glycoprotein coding sequence with a start codon of ATG 810 and a restriction site of NdeI at the 5' end of the ISG glycoprotein coding sequence. The downstream regulatory region DRR 814 includes the transcription terminator sequence as well as the stop codon and 3' cassette restriction site 816 on the 3'UTR end 818. The downstream regulatory region may include a peptide tag such as the FLAG 3× tag. A selectable marker such as a paromomycin resistance marker (aph VIIIsr) (such as SEQ ID NO:21 or SEQ ID NO:22) may also be used in the construct. Each of these components is operably linked to the next, i.e., the HSP70A/RBCS2 promoter sequence with the Intron 1 sequence is operably linked to the 5' end of the ISG glycoprotein coding sequence encoding the cell adhesion protein. The ISG glycoprotein coding sequence is operably linked to the 5' end of the downstream regulatory region. The DNA construct Pro-IP-ISG-DRR is then integrated into a photosynthetic unicell such as *Chlamydomonas reinhardtii* and organisms expressing the cell adhesion protein are then generated. The photosynthetic unicells containing the DNA construct may then be formed into and induced to adhere into a multicellular shape.

Figure 9:
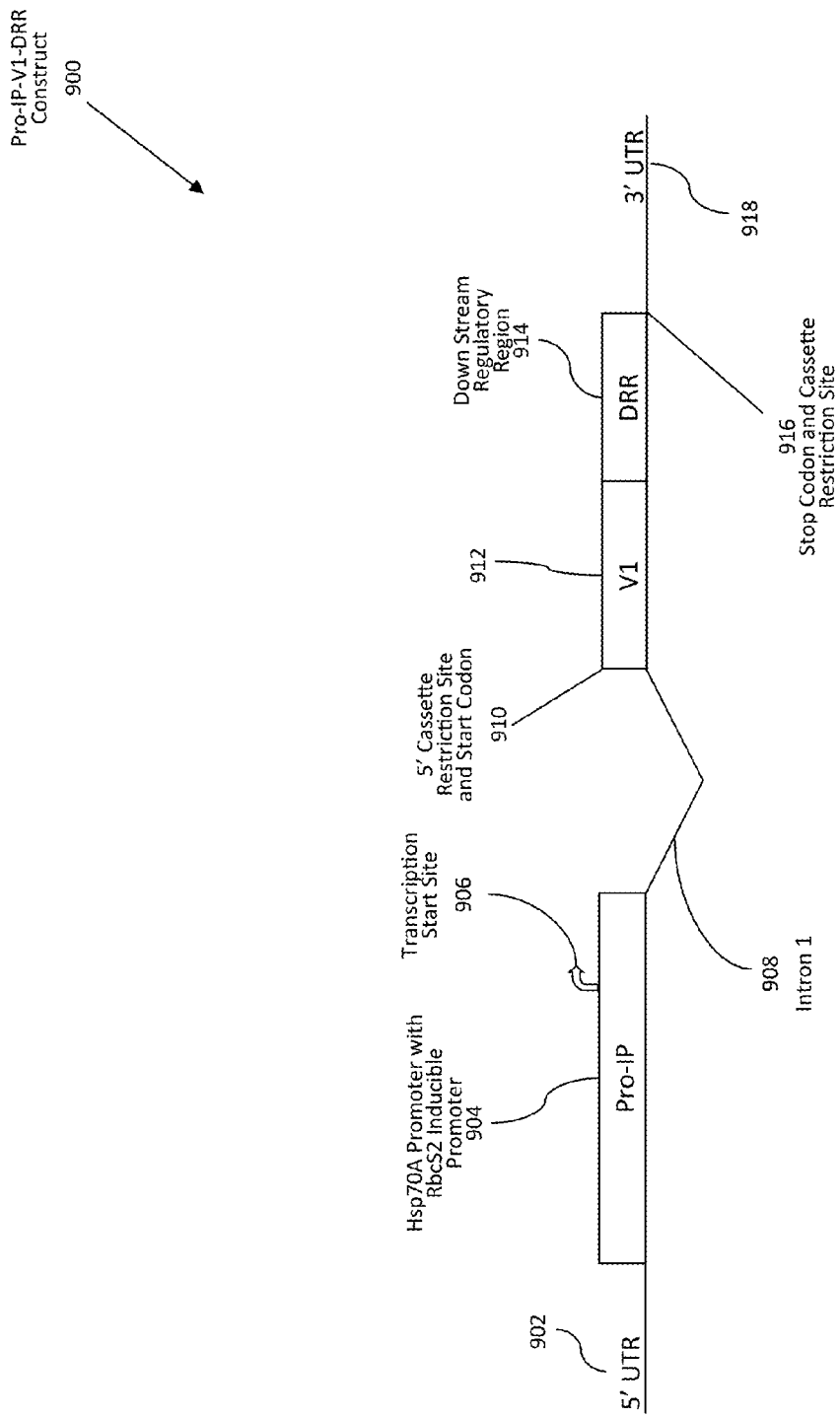
FIG. 9 is a map of a DNA construct, represented as Pro-IP-V1-DRR that includes (from 5' to 3'), a promoter with an inducible promoter, the V1 protein coding sequence, and a downstream regulatory region.

As shown in FIG. 9, a construct is generally represented as Pro-IP-V1-DRR 900, where on the 5' UTR end 902 Pro-IP 904 is a promoter with an inducible promoter such as the RBCS2 promoter flanked by enhancer elements of HSP70A and RBCS2 intron 1 (SEQ ID NO:9), 908 on the 3' end as well as a SacI restriction site on the 5' end with a transcription start site 906. V1 (SEQ ID NO:3 or SEQ ID NO:4) 912 is an extracellular HRGP extensin-related protein coding sequence with a start codon of ATG 910 and a restriction site of NdeI at the 5' end of the V1 coding sequence. The downstream regulatory region DRR 914 includes the transcription terminator sequence as well as the stop codon and 3' cassette restriction site 916 on the 3'UTR end 918. The downstream regulatory region may include a peptide tag such as the FLAG 3× tag. A selectable marker such as a paromomycin resistance marker (aph VIIIsr) (such as SEQ ID NO:21 or SEQ ID NO:22) may also be used in the construct. Each of these components is operably linked to the next, i.e., the HSP70A/RBCS2 promoter sequence with the Intron 1 sequence is operably linked to the 5' end of the V1 extracellular HRGP extensin-related protein coding sequence encoding the cell adhesion protein. The V1 protein coding sequence is operably linked to the 5' end of the downstream regulatory region. The DNA construct Pro-IP-V1-DRR is then integrated into a photosynthetic unicell such as *Chlamydomonas reinhardtii* and organisms expressing the cell adhesion protein are then generated. The photosynthetic unicells containing the DNA construct may then be formed into and induced to adhere into a multicellular shape.

Figure 10:
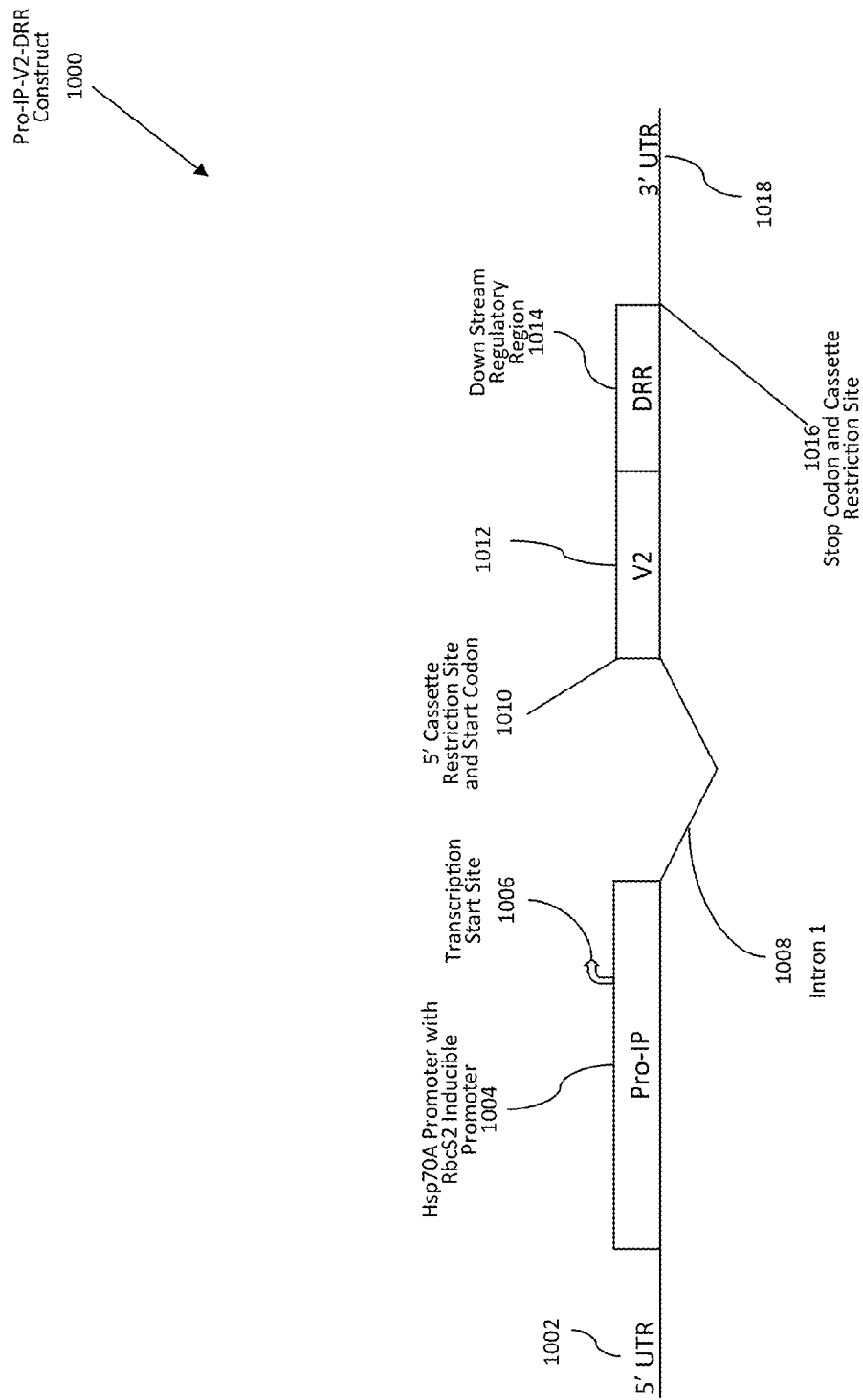
FIG. 10 is a map of a DNA construct, represented as Pro-IP-V2-DRR that includes (from 5' to 3'), a promoter with an inducible promoter, the V2 protein coding sequence, and a downstream regulatory region.

As shown in FIG. 10, a construct is generally represented as Pro-IP-V2-DRR 1000, where on the 5' UTR end 1002 Pro-IP 1004 is a promoter with an inducible promoter such as the RBCS2 promoter flanked by enhancer elements of HSP70A and RBCS2 intron 1 (SEQ ID NO:9), 1008 on the 3' end as well as a SacI restriction site on the 5' end with a transcription start site 1006. V2 (including but not limited to SEQ ID NO:5 or SEQ ID NO:6) 1012 is an extracellular HRGP extensin-related protein coding sequence with a start codon of ATG 1010 and a restriction site of NdeI at the 5' end of the V2 coding sequence. The downstream regulatory region DRR 1014 includes the transcription terminator sequence as well as the stop codon and 3' cassette restriction site 1016 on the 3'UTR end 1018. The downstream regulatory region may include a peptide tag such as the FLAG 3× tag. A selectable marker such as a paromomycin resistance marker (aphVIIIsr) (such as SEQ ID NO:21 or SEQ ID NO:22) may also be used in the construct. Each of these components is operably linked to the next, i.e., the HSP70A/RBCS2 promoter sequence with the Intron 1 sequence is operably linked to the 5' end of the V2 extracellular HRGP extensin-related protein coding sequence encoding the cell adhesion protein. The V2 protein coding sequence is operably linked to the 5' end of the downstream regulatory region. The DNA construct Pro-IP-V2-DRR is then integrated into a photosynthetic unicell such as *Chlamydomonas reinhardtii* and organisms expressing the cell adhesion protein are then generated. The photosynthetic unicells containing the DNA construct may then be formed into and induced to adhere into a multicellular shape.

Figure 11:
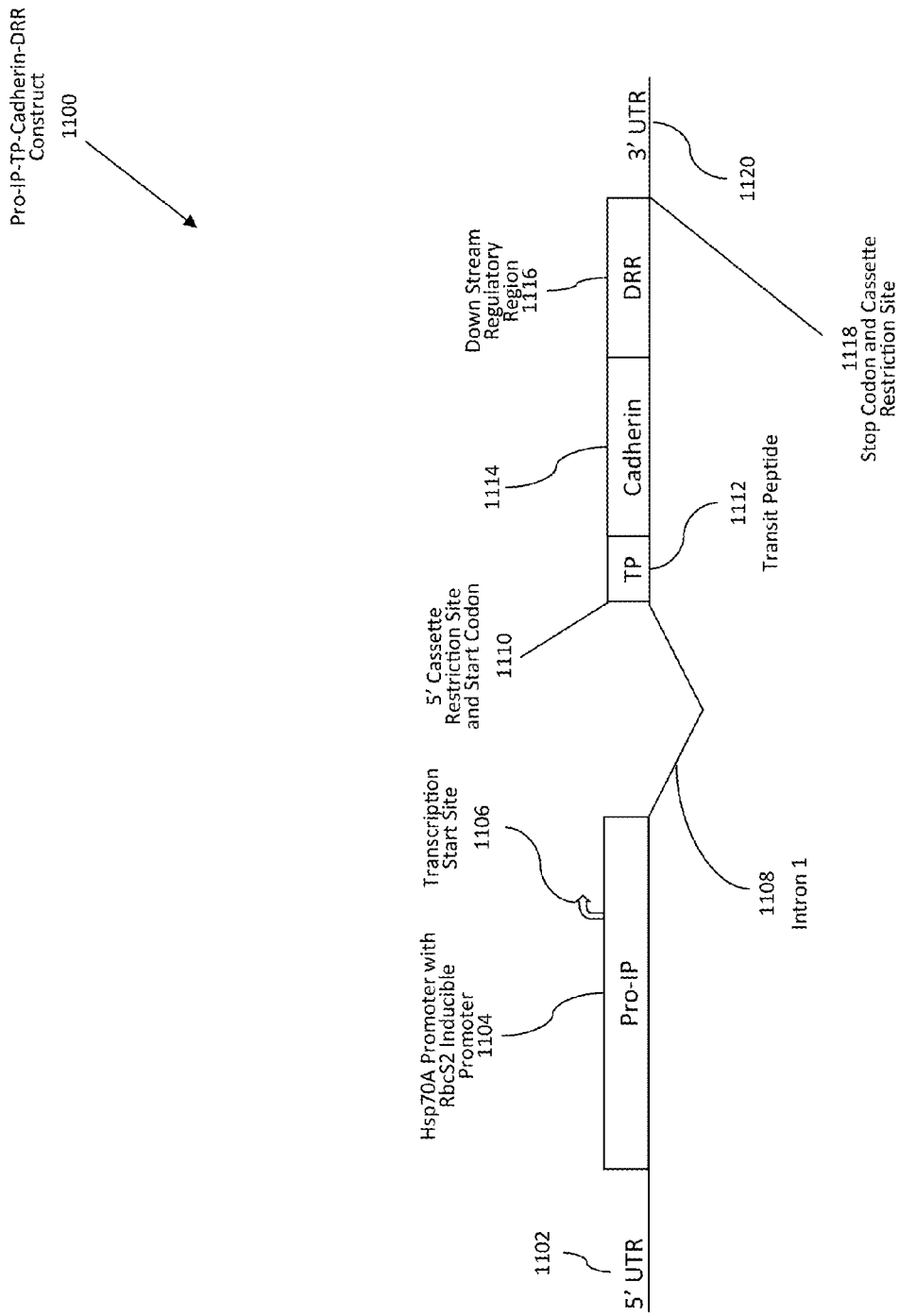
FIG. 11 is a map of a DNA construct, represented as Pro-IP-TP-Cadherin-DRR that includes (from 5' to 3'), a promoter with an inducible promoter, a transit peptide coding sequence, the cadherin protein coding sequence, and a downstream regulatory region.

As shown in FIG. 11, a construct is generally represented as Pro-IP-TP-Cadherin-DRR 1100, where on the 5' UTR end 1102, Pro-IP 1104 is a promoter with a inducible promoter such as the RBCS2 promoter flanked by enhancer elements of HSP70A and RBCS2 intron 1 (such as but not limited to SEQ ID NO:9), 1108 on the 3' end as well as a SacI restriction site on the 5' end with a transcription start site 1106. TP 1112 is an algae specific transit peptide coding sequence, which directs transcription to the outer membrane or extracellular matrix of the algae. The transit peptide is operably linked to a cadherin protein coding sequence (including but not limited to SEQ ID NO:27, SEQ ID NO:28, SEQ ID NO:29 or SEQ ID NO:30) 1114 which is a calcium-dependent cell adhesion protein. Further, the cadherin protein fuses to the C-terminus of a catenin protein. The fusion domains between the cadherin protein and the catenin protein act to bind the cadherin to actin filaments of the cytoskeleton, which will cause flocculation or cell adhesion of the algae. The N-terminal domains of the cadherin protein are hemophilic and binds with the same adhesion scheme of Algal-CAM protein in that the protein is homophilic and thus binds to itself. The transit peptide has a start codon and a restriction site 1110 at the 5' end of the transit peptide coding sequence. The downstream regulatory region DRR 1116 includes the transcription terminator sequence as well as the stop codon and 3' cassette restriction site 1118 on the 3'UTR end 1120. The downstream regulatory region may include a peptide tag such as the FLAG 3× tag. A selectable marker such as a paromomycin resistance marker (aphVIIIsr) (such as SEQ ID NO:21 or SEQ ID NO:22) may also be used in the construct. Each of these components is operably linked to the next, i.e., the HSP70A/RBCS2 promoter sequence with the Intron 1 sequence is operably linked to the 5' end of the transit peptide. The transit peptide is operably linked to the 5' end of the cadherin protein. The cadherin protein coding sequence is operably linked to the 5' end of the downstream regulatory region. The DNA construct Pro-IP-TP-Cadherin-DRR is then integrated into a photosynthetic unicell such as *Chlamydomonas reinhardtii* where the cell wall of the organism has been removed by means of an induced mutation, fusing an enzyme to the organism or fusing a cell wall degrading enzyme to the cadherin DNA construct Pro-IP-TP-Cadherin-DRR. Organisms expressing the cadherin cell adhesion protein, including expression in the outer membrane or extracellular matrix, are then generated. The photosynthetic unicells containing the DNA construct may then be formed into and induced to adhere into a multicellular shape.

Figure 12:
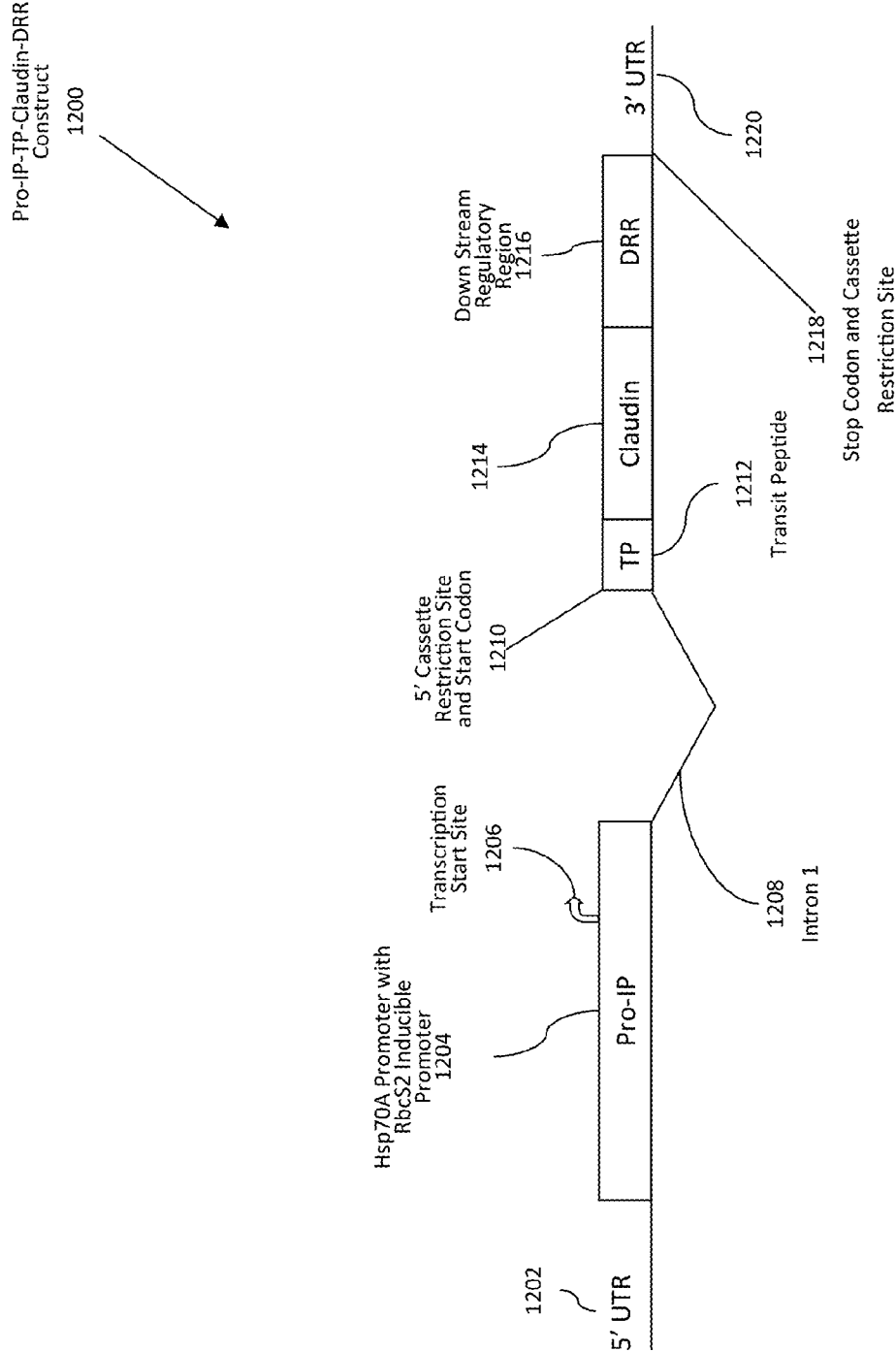
FIG. 12 is a map of a DNA construct, represented as Pro-IP-TP-Claudin-DRR that includes (from 5' to 3'), a promoter with an inducible promoter, a transit peptide coding sequence, the cadherin protein coding sequence, and a downstream regulatory region.

As shown in FIG. 12, a construct is generally represented as Pro-IP-TP-Claudin-DRR 1200, where on the 5' UTR end 1202 Pro-IP 1204 is a promoter with an in inducible promoter, such as the RBCS2 promoter flanked by enhancer elements of HSP70A and RBCS2 intron 1 (such as but not limited to SEQ ID NO:9), 1208 on the 3' end as well as a SacI restriction site on the 5' end with a transcription start site 1206. TP 1212 is an algae specific transit peptide coding sequence, which directs transcription to the outer membrane or extracellular matrix of the organism. The transit peptide coding sequence is operably linked to a claudin transmembrane protein coding sequence (including but not limited to SEQ ID NO:31, SEQ ID NO:32, SEQ ID NO:33, SEQ ID NO:34, SEQ ID NO:35 and SEQ ID NO:36) 1214. The transit peptide has a start codon and a restriction site 1210 at the 5' end of the transit peptide coding sequence. The downstream regulatory region DRR 1216 includes the transcription terminator sequence as well as the stop codon and 3' cassette restriction site 1218 on the 3'UTR end 1220. The downstream regulatory region may include a peptide tag such as the FLAG 3× tag. A selectable marker such as a paromomycin resistance marker (aphVIIIsr) (such as SEQ ID NO:21 or SEQ ID NO:22) may also be used in the construct. Each of these components is operably linked to the next, i.e., the HSP70A/RBCS2 promoter sequence with the Intron 1 sequence is operably linked to the 5' end of the transit peptide. The transit peptide is operably linked to the 5' end of the claudin protein. The claudin protein coding sequence is operably linked to the 5' end of the downstream regulatory region. The DNA construct Pro-IP-TP-Claudin-DRR is then integrated into a photosynthetic unicell such as *Chlamydomonas reinhardtii* where the cell wall of the organism has been removed using by means of induced mutation, fusing an enzyme to the organism or fusing a cell wall degrading enzyme to the claudin DNA construct Pro-IP-TP-Claudin-DRR. Organisms expressing the claudin cell adhesion protein including expression in the outer membrane or extracellular matrix, are then generated. The photosynthetic unicells containing the DNA construct may then be formed into and induced to adhere into a multicellular shape.

Figure 13:
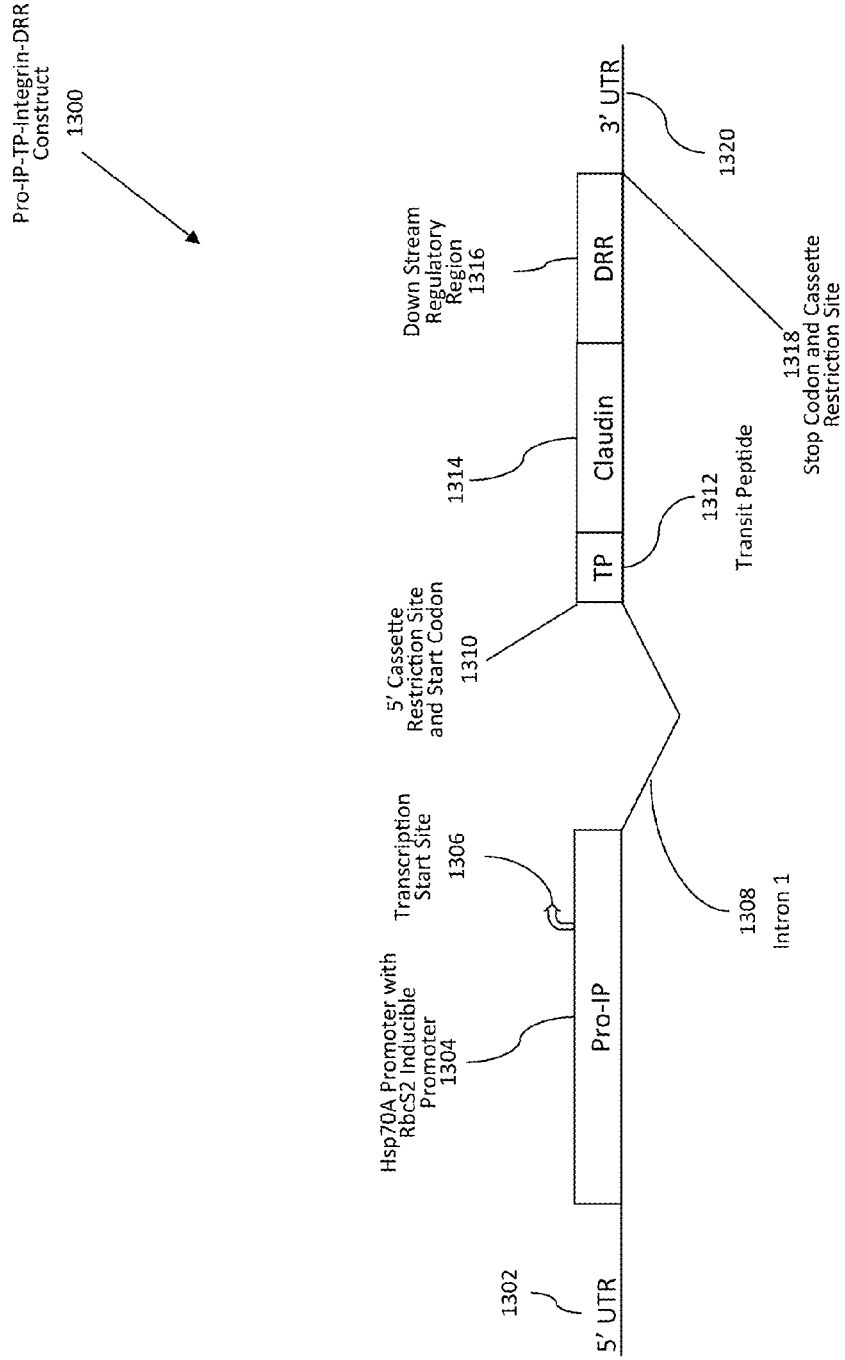
FIG. 13 is a map of a DNA construct, represented as Pro-IP-TP-Integrin-DRR that includes (from 5' to 3'), a promoter with an inducible promoter, a transit peptide coding sequence, the integrin protein coding sequence, and a downstream regulatory region.

As shown in FIG. 13, a construct is generally represented as Pro-IP-TP-Integrin-DRR 1300, where on the 5' UTR end 1302 Pro-IP 1304 is a promoter with an in inducible promoter, such as the RBCS2 promoter flanked by enhancer elements of HSP70A and RBCS2 intron 1 (such as but not limited to SEQ ID NO:9), 1308 on the 3' end as well as a SacI restriction site on the 5' end with a transcription start site 1306. TP 1312 is an algae specific transit peptide coding sequence, which directs transcription to the outer membrane or extracellular matrix of the organism. The transit peptide coding sequence is operably linked to an integrin transmembrane protein coding sequence (including but not limited to SEQ ID NO:25 and SEQ ID NO:26) 1314. The transit peptide has a start codon and a restriction site 1310 at the 5' end of the transit peptide coding sequence. The downstream regulatory region DRR 1316 includes the transcription terminator sequence as well as the stop codon and 3' cassette restriction site 1318 on the 3'UTR end 1320. The downstream regulatory region may include a peptide tag such as the FLAG 3× tag. A selectable marker such as a paromomycin resistance marker (aph VIIIsr) (such as SEQ ID NO:21 or SEQ ID NO:22) may also be used in the construct. Each of these components is operably linked to the next, i.e., the HSP70A/RBCS2 promoter sequence with the Intron 1 sequence is operably linked to the 5' end of the transit peptide. The transit peptide is operably linked to the 5' end of the integrin protein. The integrin protein coding sequence is operably linked to the 5' end of the downstream regulatory region. The DNA construct Pro-IP-TP-Integrin-DRR is then integrated into a photosynthetic unicell such as *Chlamydomonas reinhardtii* where the cell wall of the organism has been removed using by means of induced mutation, fusing an enzyme to the organism or fusing a cell wall degrading enzyme to the claudin DNA construct Pro-IP-TP-Integrin-DRR. Organisms expressing the Integrin cell adhesion protein including expression in the outer membrane or extracellular matrix, are then generated. The photosynthetic unicells containing the DNA construct may then be formed into and induced to adhere into a multicellular shape.

Generally, the DNA that is introduced into an organism is part of a construct. A construct is an artificially constructed segment of DNA that may be introduced into a target organism tissue or organism cell. Constructs are engineered DNA molecules that encode genes and flanking sequences that enable the constructs to integrate into the host genome at (targeted) locations. The DNA may be a gene of interest, e.g., a coding sequence for a protein, or it may be a sequence that is capable of regulating expression of a gene, such as an antisense sequence, a sense suppression sequence, or a miRNA sequence. As used herein, "gene" refers to a segment of nucleic acid. A gene can be introduced into a genome of a species, whether from a different species or from the same species. The construct typically includes regulatory regions operably linked to the 5' side of the DNA of interest and/or to the 3' side of the DNA of interest. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation. A cassette containing all of these elements is also referred to herein as an expression cassette. The expression cassettes may additionally contain 5' leader sequences in the expression cassette construct. (A leader sequence is a nucleic acid sequence containing a promoter as well as the upstream region of a gene.) The regulatory regions (i.e., promoters, transcriptional regulatory regions, translational regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670 and 2006/0248616. The expression cassette may additionally contain selectable marker genes which will be discussed in more detail later.

The products of the genes are often proteins, but in non-protein coding genes such as rRNA genes or tRNA genes, the product is a functional RNA. The process of gene expression is used by all known life forms, i.e., eukaryotes (including multicellular organisms), prokaryotes (bacteria and archaea), and viruses, to generate the macromolecular machinery for life. Several steps in the gene expression process may be modulated, including the transcription, up-regulation, RNA splicing, translation, and post translational modification of a protein.

The expression cassette or chimeric genes in the transforming vector typically have a transcriptional termination region at the opposite end from the transcription initiation regulatory region. The transcriptional termination region may normally be associated with the transcriptional initiation region from a different gene. The transcriptional termination region may be selected, particularly for stability of the mRNA, to enhance expression. Illustrative transcriptional termination regions include the NOS terminator from *Agrobacterium* Ti plasmid and the rice α-amylase terminator.

A promoter is a DNA region, which includes sequences sufficient to cause transcription of an associated (downstream) sequence. The promoter may be regulated, i.e., not constitutively acting to cause transcription of the associated sequence. If inducible, there are sequences present therein which mediate regulation of expression so that the associated sequence is transcribed only when an inducer molecule is present. The promoter may be any DNA sequence that shows transcriptional activity in the chosen plant cells, plant parts, or plants. The promoter may be inducible or constitutive. It may be naturally-occurring, may be composed of portions of various naturally-occurring promoters, or may be partially or totally synthetic. Guidance for the design of promoters is derived from studies of promoter structure, such as that of Harley and Reynolds, *Nucleic Acids Res.*, 15, 2343-61 (1987). In addition, the location of the promoter relative to the transcription start may be optimized. Many suitable promoters for use in algae, plants, and photosynthetic bacteria are well known in the art, as are nucleotide sequences, which enhance expression of an associated expressible sequence.

While the PSAD constitutive promoter (SEQ ID NO: 9) and the riboswitch translational regulator (SEQ ID NO:12) or the regulatory region upstream of the protein coding sequences are examples of promoters that may be used, a number of promoters may be used herein, including but not limited to, the HSP70A/RBCS2 promoter and intron 1 (SEQ ID NO:7) inducible promoter and transcription processing improvement sequences. Promoters can be selected based on the desired outcome. That is, the nucleic acids can be combined with constitutive, tissue-preferred, or other promoters for expression in the host cell of interest. The promoter may be inducible or constitutive. It may be naturally-occurring, may be composed of portions of various naturally-occurring promoters, or may be partially or totally synthetic. In addition, the location of the promoter relative to the transcription start may be optimized. Many suitable promoters for use in algae, plants, and photosynthetic bacteria are well known in the art, as are nucleotide sequences, which enhance expression of an associated expressible sequence.

Cell adhesion molecules are diverse proteins and other molecules that serve to attach the cell walls or extracellular matrices of adjacent cells together in multicellular organisms. Examples of cell adhesion molecules include but are not limited to the glycoproteins known as extensins, pherophorins, integrins, and claudins.

Inversion-Specific Glycoprotein (ISG)

ISG (SEQ ID NO:1 and SEQ ID NO:2) is a development-specific cell wall glycoprotein that is involved in cell adhesion during the inversion stage of *Volvox* sp. embryonic development (see H Ertl et al., *The EMBO Journal* 6:2055-2062, 1994) Prior to inversion, the cell wall of *Volvox* embryos is nearly absent and their cells are held together by cytoplasmic bridges. During inversion, the cytoplasmic bridges disintegrate and ISG is expressed, though only for a few minutes. ISG molecules hold *Volvox* cells together during inversion but also form a preliminary matrix to which subsequent cell wall elements are added as the post-inversion *Volvox* colony develops the thick, complex cell wall characteristic of *Volvox* at maturity. Expression of ISG is a necessary first step to engineering a *Volvox*-like cell wall in *Chlamydomonas* that can hold cells together in a robust, multicellular structure. ISG consists of a C-terminal rod-shaped extensin domain fused to an N-terminal globular domain. The most C-terminal portion of ISG includes a unique patch of positively charged residues situated close to an adjacent patch of negatively charged residues. The structure and charge distribution of ISG allow it to form branched networks with itself and other cell wall elements that serve as a molecular scaffold for other cell wall components as they are secreted. ISG occurs in the BZ3 layer of the *Volvox* cell wall, which is functionally equivalent to the *Chlamydomonas* W2 layer. ISG is an organizer for *Volvox* cell wall development because the W2 wall layer in *Chlamydomonas* is also known to nucleate and organize its cell wall.

Pherophorins V1 and V2

While ISG alone causes some degree of cell adhesion in *Chlamydomonas*, the use of "pherophorins" (V1 and V2) (SEQ ID NO:3, SEQ ID NO: 4, SEQ ID NO:5 and SEQ ID NO: 6) of *Volvox* act in synergy with ISG and are effective multicellularity inducers in their own right. Pherophorins are a family of hydroxyproline-rich glycoprotein (HRGP) extensin-related proteins present in the Volvocalean cell wall (see A Hallmann, *The Plant Journal* 45:292-307, 2006). Pherophorins V1 and V2 are especially important for repair of physical damage to the *Volvox* cell wall. Expression of these proteins in *Chlamydomonas* adds the bulk meshwork needed for an expanded, *Volvox*-like cell wall. Expressing V1 and/or V2 in combination with ISG, each from independent transgenes is effective because ISG facilitates and organizes the assembly of V1 and V2. V1 and V2 are expressed during *Volvox* cell wall development and also during cell wall repair after wounding. V1 and V2 structures closely resemble that of ISG but with two distinctions: (i) the rod-shaped extensin domain has slightly different repeat motifs and (ii) it is flanked on each end by globular lectin domains, giving V1 and V2 a dumbbell-shaped conformation. HRGPs with this conformation are thought to form complex, intermolecular meshworks, with mesh size determined by length of the extensin domain. The globular domains of pherophorins bind end-to-end and also side-to-side, resulting in a complex proteinaceous matrix similar to type I and IV collagens.

Algal-CAM Protein

Adhesion of cells in *V. carteri* is mediated by glycoproteins, one of which is designated Algal-CAM, (SEQ ID NO:17, SEQ ID NO:18, SEQ ID NO:19 and SEQ ID NO:20). Algal-CAM is made up of three primary structural domains: an N-terminal extensin-like domain and two C-terminal fasciclin I domains. The N-terminal extensin-like domain belongs to a family of rod shaped hydroxyproline-rich glycoprotein (HRGP) domains found within the cell wall of *V. carteri, C. reinhardtii*, other green algae, and higher plants. In *C. reinhardtii* and higher plants, extensin domains are known to become insolubilized upon secretion to the hydroxyproline-enriched extracellular matrix by covalent isodityrosine cross-linking (see Waffenschmidt et al., *The Plant Cell* 5:809-820, 1993). Fasciclin I domains are known to mediate cell-cell adhesion by homophilic binding interactions (see Huber and Sumper, *The EMBO Journal*, 13:4212-4222, 1994). The combination of a wall anchoring extensin domain and homophilic fasciclin I domains allow Algal-CAM to bind the cell walls of adjacent *V. carteri* cells together.

Human Type I Collagen

Extensins of plants and algae are analogous in structure and function to collagens (COL) (SEQ ID NO: 23 and SEQ ID NO: 24), which are key constituents of animal extracellular matrices. Extensins and collagens are modified in similar ways after translation by hydroxylation, glycosylation and covalent cross-linking. A fundamental difference between collagens and extensins is the quaternary structure of mature collagen protein. Collagen alpha chains form a trimeric rope-like triple helix. Collagen trimerization at human temperatures proceeds by hydroxylation of proline resides along individual α-chains, which is catalyzed by prolyl 4-hydroxylases (P4Hs). Collagens can passively trimerize without hydroxylation but such trimers are not thermally stable at human temperatures. Interestingly, the *Chlamydomonas* genome encodes 10 different P4Hs within its genome and their catalytic domains are very similar to those of animal P4Hs. Native P4Hs of *Chlamydomonas* can form hydroxyproline-stabilized homotrimers of type I collagen and has been successfully expressed in tobacco. Type I homotrimeric collagen is used in medicine and can become contaminated with viruses and other infectious agents when produced from animal cells. Collagen produced in *Chlamydomonas* or other photosynthetic unicells is free of such viruses. Type I collagen also adds mechanical strength and flexibility to the *Chlamydomonas* cell wall and to and structure or material produced by self-assembling photosynthetic unicells as described here.

Cadherin Proteins

Cadherin proteins are a group of calcium-dependent cell adhesion proteins (SEQ ID NO: 27, SEQ ID NO: 28, SEQ ID NO: 29 and SEQ ID NO: 30). Cadherin proteins promote cell adhesion through homophilic interactions. N (neural)-cadherin is predominantly expressed by neural cells, endothelial cells and a variety of cancer cell types. E (epithelial)-cadherin is predominantly expressed by epithelial cells. Other cadherins are P (placental)-cadherin, which is found in human skin and R (retinal)-cadherin. A transit peptide (TP) is a peptide coding sequence that which is operably linked to a protein such as the cadherin protein in order to facilitate translation or direct translation of the protein to a specific location in the organism of interest.

Claudin Proteins

Claudin proteins are a family of transmembrane proteins with binding domains that are important in formation of cell junctions (examples may include but are not limited to SEQ ID NO: 31, SEQ ID NO: 32, SEQ ID NO: 33, SEQ ID NO: 34, SEQ ID NO: 35 or SEQ ID NO: 36). The cell junctions that claudin proteins create control cell transport and cell polarity as well as cell permeability.

Integrin Proteins

Integrin proteins are a family of transmembrane proteins that mediate the attachment between a cell and the cells or tissues that surround it (examples may include but are not limited to SEQ ID NO: 25 or SEQ ID NO: 26).

Expression of Cell Adhesion Proteins

Expression of cell adhesion proteins, such as Algal-CAM, ISG, V1, V2, COL, claudin, cadherin, or integrin proteins, in the cell walls of photosynthetic unicells may be induced through a variety of methods which are known in the art and would be understood by one skilled in the art. Examples of methods of inducing expression of cell adhesion proteins in photosynthetic unicells may include but is not limited to: 1. removing of ammonium from the growth medium where photosynthetic unicells are grown in order to induce activity of a NIT1 inducible promoter; 2. removing thiamine from the growth medium where photosynthetic unicells are grown so as to activate translation controlled by a THI4 translational regulator; 3. using external agents to induce transcription; or 4. translation of transgenes by means of external stimuli.

Vector Construction, Transformation, and Heterologous Protein Expression

As used herein plasmid, vector or cassette refers to an extrachromosomal element often carrying genes and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with an appropriate 3' untranslated sequence into a cell.

While one example of an expression vector is a *Chlamydomonas* expression vector designated pSI105, derivatives of the vectors described herein may be capable of stable transformation of many photosynthetic unicells, including but not limited to unicellular algae of many species, photosynthetic bacteria, and single photosynthetic cells, e.g. protoplasts, derived from the green parts of plants. Vectors for stable transformation of algae, bacteria, and plants are well known in the art and can be obtained from commercial vendors or constructed from publicly available sequence information. Expression vectors can be engineered to produce heterologous and/or homologous protein(s) of interest (e.g., antibodies, mating type agglutinins, etc.). Such vectors are useful for recombinantly producing the protein of interest and for modifying the natural phenotype of host cells (e.g., expressing a cell adhesion protein).

To construct the vector, the upstream DNA sequences of a gene expressed under control of a suitable promoter may be restriction mapped and areas important for the expression of the protein characterized. The exact location of the start codon of the gene is determined and, making use of this information and the restriction map, a vector may be designed for expression of a heterologous protein by removing the region responsible for encoding the gene's protein but leaving the upstream region found to contain the genetic material responsible for control of the gene's expression. A synthetic oligonucleotide is inserted in the location where the protein sequence once was, such that any additional gene could be cloned in using restriction endonuclease sites in the synthetic oligonucleotide (i.e., a multicloning site). Publicly available restriction proteins may be used for the development of the constructs. An unrelated gene (or coding sequence) inserted at this site would then be under the control of an extant start codon and upstream regulatory region that will drive expression of the foreign (i.e., not normally present) protein encoded by this gene. Once the gene for the foreign protein is put into a cloning vector, it can be introduced into the host organism using any of several methods, some of which might be particular to the host organism. Variations on these methods are described in the general literature. Manipulation of conditions to optimize transformation for a particular host is within the skill of the art.

The basic transformation techniques for expression in photosynthetic unicells are commonly known in the art. These methods include, for example, introduction of plasmid transformation vectors or linear DNA by use of cell injury, by use of biolistic devices, by use of a laser beam or electroporation, by microinjection, or by use of *Agrobacterium tumifaciens* for plasmid delivery with transgene integration or by any other method capable of introducing DNA into a host cell.

In some embodiments, biolistic plasmid transformation of the chloroplast genome can be achieved by introducing regions of chloroplast DNA flanking a desired nucleotide sequence, allowing for homologous recombination of the exogenous DNA into the target chloroplast genome. Plastid transformation is a routine and well known in the art (see U.S. Pat. Nos. 5,451,513, 5,545,817, and 5,545,818; WO 95/16783; McBride et al., *Proc. Natl. Acad. Sci., USA* 91:7301-7305, 1994). In some instances one to 1.5 kb flanking nucleotide sequences of chloroplast genomic DNA may be used. Using this method, point mutations in the chloroplast 16S rRNA and rps12 genes, which confer resistance to spectinomycin and streptomycin, can be utilized as selectable markers for transformation and can result in stable homoplasmic transformants, at a frequency of approximately one per 100 bombardments of target cells (Svab et al., *Proc. Natl. Acad. Sci., USA* 87:8526-8530, 1990).

Biolistic microprojectile-mediated transformation also can be used to introduce a polynucleotide into photosynthetic unicells for nuclear integration. This method utilizes microprojectiles such as gold or tungsten, which are coated with the desired polynucleotide by precipitation with calcium chloride, spermidine or polyethylene glycol. The microprojectile particles are accelerated at high speed into cells using a device such as the BIOLISTIC PD-1000 particle gun. Methods for the transformation using biolistic methods are well known in the art (see, e.g.; Christou, *Trends in Plant Science* 1:423-431, 1996). Microprojectile mediated transformation has been used, for example, to generate a variety of transgenic organism species, including cotton, tobacco, corn, hybrid poplar and papaya. Important cereal crops such as wheat, oat, barley, sorghum and rice also have been transformed using microprojectile mediated delivery. The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, the glass bead agitation method, and the like. Transformation frequency may be increased by replacement of recessive rRNA or r-protein antibiotic resistance genes with a dominant selectable marker, including, but not limited to the bacterial aadA gene (Svab and Maliga, *Proc. Natl. Acad. Sci., USA* 90:913-917, 1993).

The basic techniques used for transformation and expression in photosynthetic organisms are known in the art. These methods have been described in a number of texts for standard molecular biological manipulation (see Packer & Glaser, "*Cyanobacteria*", Meth. Enzymol., Vol. 167, 1988; Weissbach & Weissbach, "*Methods for Plant Molecular Biology*," Academic Press, New York 1988; Sambrook, Fritsch & Maniatis, "*Molecular Cloning: A laboratory manual*," 2nd edition Cold Spring Harbor Laboratory Press, Cold Spring Harbor, N.Y., 1989; and Clark M S, Plant Molecular Biology, Springer, N.Y., 1997). These methods include, for example, biolistic devices (See, for example, Sanford, *Trends In Biotech.*, 6: 299-302, 1988); U.S. Pat. No. 4,945,050; electroporation (Fromm et al., *Proc. Nat'l. Acad. Sci. USA*, 82: 5824-5828, 1985); use of a laser beam, electroporation, microinjection or any other method capable of introducing DNA into a host cell (e.g., an NVPO).

Other transformation methods are available to those skilled in the art, such as direct uptake of foreign DNA constructs (see EP 295959), techniques of electroporation (see Fromm et al. *Nature (London)* 319:791, 1986) or high-velocity ballistic bombardment with metal particles coated with the nucleic acid constructs (see Kline et al. *Nature* (London) 327:70, 1987; and see U.S. Pat. No. 4,945,050).

To confirm the presence of the transgenes in transgenic cells, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic organisms have been obtained, they may be grown to produce organisms or parts having the desired phenotype.

Method for Use of Fluorescent Peptide (FP)

Fluorescent peptide (FP) fusions allow analysis of dynamic localization patterns in real time. Over the last several years, a number of different colored fluorescent peptides have been developed and may be used in various constructs, including yellow FP (YFP), cyan FP (CFP), red FP (mRFP) and others. Some of these peptides have improved spectral properties, allowing analysis of fusion proteins for a longer period of time and permitting their use in photobleaching experiments. Others are less sensitive to pH, and other physiological parameters, making them more suitable for use in a variety of cellular contexts. Additionally, FP-tagged proteins can be used in protein-protein interaction studies by bioluminescence resonance energy transfer (BRET) or fluorescence resonance energy transfer (FRET). High-throughput analyses of FP fusion proteins in *Arabidopsis* have been performed by overexpressing cDNA-GFP fusions driven by strong constitutive promoters. A standard protocol is to insert the mRFP tag or marker at a default position of ten amino acids upstream of the stop codon, following methods established for *Arabidopsis* (Tian et al., *PlantPhysiol.* 135: 25-38, 2004). Although useful, this approach has inherent limitations, as it does not report tissue-specificity, and overexpression of multimeric proteins may disrupt the complex. Furthermore, overexpression can lead to protein aggregation and/or mislocalization.

In order to tag a specific gene with a fluorescent peptide such as the red fluorescent protein (mRFP), usually a gene ideal for tagging has been identified through forward genetic analysis or by homology to an interesting gene from another model system. For generation of native expression constructs, full-length genomic sequence is required. For tagging of the full-length gene with an FP, the full-length gene sequence should be available, including all intron and exon sequences. A standard protocol is to insert the mRFP tag or marker at a default position of ten amino acids upstream of the stop codon, following methods known in the art established for *Arabidopsis*. The rationale is to avoid masking C-terminal targeting signals (such as endoplasmic reticulum (ER) retention or peroxisomal signals). In addition, by avoiding the N-terminus, disruption of N-terminal targeting sequences or transit peptides is avoided. However, choice of tag insertion is case-dependent, and it should be based on information on functional domains from database searches. If a homolog of the gene of interest has been successfully tagged in another organism, this information is also used to choose the optimal tag insertion site. A flexible linker peptide may be placed between proteins such that the desired protein obtained. A cleavable linker peptide may also be placed between proteins such that they can be cleaved and the desired protein obtained.

Selectable Markers

A selectable marker (SM), can provide a means to obtain plant cells that express the resistance marker and can be useful as a component of a construct. Selectable markers include, but are not limited to, neomycin phosphotransferase, such as paromomycin resistance marker (aph VIIIsr) (SEQ ID NO:21 and SEQ ID NO:22) which confers resistance to the aminoglycosides neomycin, kanamycin and paromycin (Herrera-Estrella, *EMBO J.* 2:987-995, 1983); dihydrofolate reductase, which confers resistance to methotrexate (Reiss, *Plant Physiol.* (*Life Sci. Adv.*) 13:143-149, 1994); trpB, which allows cells to utilize indole in place of tryptophan; hisD, which allows cells to utilize histinol in place of histidine (Hartman, *Proc. Natl. Acad. Sci.*, USA 85:8047, 1988); mannose-6-phosphate isomerase which allows cells to utilize mannose (WO 94/20627); hygro, which confers resistance to hygromycin (Marsh, *Gene* 32:481-485, 1984); ornithine decarboxylase, which confers resistance to the ornithine decarboxylase inhibitor, 2-(difluoromethyl)-DL-ornithine (DFMO; McConlogue, In: *Current Communications in Molecular Biology*, Cold Spring Harbor Laboratory ed., 1987); deaminase from *Aspergillus terreus*, which confers resistance to Blasticidin S (Tamura, *Biosci. Biotechnol. Biochem.* 59:2336-2338, 1995); phosphinothricin acetyltransferase gene, which confers resistance to phosphinothricin (White et al., *Nucl. Acids Res.* 18:1062, 1990; Spencer et al., *Theor. Appl. Genet.* 79:625-633, 1990); a mutant acetolactate synthase, which confers imidazolione or sulfonylurea resistance (Lee et al., *EMBO J.* 7:1241-1248, 1988), a mutant EPSPV-synthase, which confers glyphosate resistance (Hinchee et al., *BioTechnology* 91:915-922, 1998); a mutant psbA, which confers resistance to atrazine (Smeda et al., *Plant Physiol.* 103:911-917, 1993), a mutant protoporphyrinogen oxidase (see U.S. Pat. No. 5,767,373), or other markers conferring resistance to an herbicide such as glufosinate. Selectable markers include polynucleotides that confer dihydrofolate reductase (DHFR) or neomycin resistance for eukaryotic cells and tetracycline; ampicillin resistance for prokaryotes such as *E. coli*; and bleomycin, gentamycin, glyphosate, hygromycin, kanamycin, methotrexate, phleomycin, phosphinotricin, spectinomycin, streptomycin, sulfonamide and sulfonylurea resistance in plants (see, for example, Maliga et al., *Methods in Plant Molecular Biology*, Cold Spring Harbor Laboratory Press, 1995, page 39).

Transcription Terminator

The transcription termination region of the constructs is a downstream regulatory region (DRR) including the stop codon TGA and the transcription terminator sequence. Alternative transcription termination regions that may be used may be native with the transcriptional initiation region, may be native with the DNA sequence of interest, or may be derived from another source. The transcription termination region may be naturally occurring, or wholly or partially synthetic. Convenient transcription termination regions are available from the Ti-plasmid of *Agrobacterium tumefaciens*, such as the octopine synthase and nopaline synthase transcription termination regions or from the genes for beta-phaseolin, the chemically inducible plant gene, pIN.

The practice described herein employs, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, et al., *Molecular Cloning*, Cold Spring Harbor Laboratory Press, Cold Spring Harbor, N.Y. (1982); Sambrook, et al., *Molecu-* lar Cloning, 2nd Ed., Cold Spring Harbor Laboratory Press, Cold Spring Harbor, N.Y. (1989); Sambrook and Russell, *Molecular Cloning*, 3rd Ed., Cold Spring Harbor Laboratory Press, Cold Spring Harbor, N.Y. (2001); Ausubel, et al., *Current Protocols in Molecular Biology*, John Wiley & Sons (including periodic updates) (1992); Glover, *DNA Cloning*, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, NY (1992); Guthrie and Fink, *Guide to Yeast Genetics and Molecular Biology*, Academic Press, NY (1991); Harlow and Lane, *Antibodies*, Cold Spring Harbor Laboratory Press, Cold Spring Harbor, N.Y. (1988); *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, A. R. Liss, Inc. (1987); *Immobilized Cells And Enzymes*, IRL Press (1986); B. Perbal, *A Practical Guide To Molecular Cloning* (1984); the treatise, *Methods In Enzymology*, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, *Essential Immunology*, 6th Edition, Blackwell Scientific Publications, Oxford (1988); Fire, et al., *RNA Interference Technology: From Basic Science to Drug Development*, Cambridge University Press, Cambridge (2005); Schepers, *RNA Interference in Practice*, Wiley-VCH (2005); Engelke, *RNA Interference* (RNAi): *The Nuts & Bolts of siRNA Technology*, DNA Press (2003); Gott, *RNA Interference, Editing, and Modification: Methods and Protocols* (*Methods in Molecular Biology*), Human Press, Totowa, N.J. (2004); and Sohail, *Gene Silencing by RNA Interference: Technology and Application*, CRC (2004)).

The practice of the various embodiments employs, unless otherwise indicated, conventional techniques of chemistry, molecular biology, microbiology, recombinant DNA, genetics, immunology, cell biology, cell culture and transgenic biology, which are within the skill of the art.

EXAMPLES

The following examples are provided to illustrate further the various applications and are not intended to limit the invention beyond the limitations set forth in the appended claims.

Example 1

Method of Producing *Chlamydomonas* Photosynthetic Unicells for Self-Assembly into Biological Structures

*Chlamydomonas* expression vectors are constructed using established recombinant DNA methods. ISG (SEQ ID NO: 1 or SEQ ID NO: 2), V1 (SEQ ID NO: 3 or SEQ ID NO: 4), and V2 (SEQ ID NO: 5 or SEQ ID NO: 6) transgenes from *Volvox* (UTEX #1886) are isolated by RT-PCR and cloned. For constitutive and/or inducible expression, a HSP70A/RBCS2 promoter (SEQ ID NO:7), or a PSAD (SEQ ID NO:9), or both in tandem are used. A PCR is conducted using primers (SEQ ID NO:10 and SEQ ID NO:11). For advanced expression control, the thiamine-sensitive 5' riboswitch THI4 (SEQ ID NO:12) is used for translational regulation, and the NIT1 $NO_3^-$ sensitive promoter for transcriptional regulation, or both in tandem for dual regulation. A PCR is conducted using primers (SEQ ID NO:13, SEQ ID NO:14, SEQ ID NO:15 and SEQ ID NO:16). Transgenes include the ISG, V1 or V2. *Volvox* cell wall genes already carry a native signal peptide that is highly conserved in volvocine green algae and functions in *Chlamydomonas* but a synthetic C-terminal FLAG tag/epitope is added to *Volvox* transgenes for immunolabeling. For *Chlamydomonas* transformation using the expression vector designated pSI105, the glass bead method is used, which places transgenes in the cell nucleus. Co-transformation with pArg7 selectable marker is used when transgenes are introduced in tandem on a single expression vector and transformants are selected for their ability to grow on arginine-free medium. The aphVIII resistance marker and selection for paromomycin resistance (SEQ ID NO:21 or SEQ ID NO:22) are used for vectors carrying a single transgene. Transgene presence and transcriptional expression in putative transformants is confirmed by PCR and RT-PCR, respectively. Protein expression levels and localization is observed by immunoblots directed against the C-terminal tags added to *Volvox* transgenes or the antigenic epitopes of human transgenes. Localization of heterologous proteins to the cell wall is confirmed with immunoblots of cell fractions.

Three *Chlamydomonas* strains are used. Wild type cells mate efficiently and have a cell wall composed of 7 layers. These layers inhibit transformation but transformable protoplasts can be generated by enzymatic digestion of the cell wall. Cell wall layers 2, 4, and 6 form especially small mesh sizes and could prevent heterologous proteins from reaching the cell wall surface, which will be necessary for cell adhesion. The *Chlamydomonas* cw-15 mutant lacks cell wall layers 2, 4, and 6. It is easily transformed and its reduced cell wall allows heterologous cell wall proteins to reach the cell wall surface. A third *Chlamydomonas* line that is useful is the cw-ts1 strain, a temperature sensitive mutant capable of assembling a cell wall at 25° C. but not at 35° C. This mutant can be transformed at 35° C., when only a minimal cell wall is present, and then allowed to form a cell wall at 25° C. with inclusion of heterologous cell wall proteins. Combination of multiple transgenes can be achieved using the tandem expression vector pSI105 and pArg7 co-transformation.

For culturing of *Chlamydomonas* in 12 well plates for observation of cell-cell adhesion, 100 µl of 72 hr liquid culture is used to inoculate 3 ml of medium in 12 well plates grown for 24 hrs in the light with shaking. Low magnification micrographs are then taken in the 12 well plates using an inverted Leica DMI3000 B microscope with a 2.5× objective after separating individual flocs by gentle rotary agitation. Higher magnification fluorescence micrographs are taken using a Zeiss 710 scanning confocal laser microscope at 63× magnification, 488 nm excitation, and 510 nm emission.

For culturing *Chlamydomonas* in 50 ml tubes for observation of cell-cell adhesion, 300 ul of 72 hr liquid culture is used to inoculate 5 ml of medium in 50 ml culture tubes that are grown for 72 hrs under light with shaking Cultures are vortexed and photographed. Cultures were then left to settle for 10 minutes and photographed again.

The expression of ISG, V1, or V2, in *Chlamydomonas*, singly or in combination, causes cell-cell adhesion and simple multicellularity. Cultures are rotated at 150 rpm on a 2.54 cm diameter of rotation in 125 ml culture flasks with baffles that increase shearing forces in the culture. Clump size is measured using Image J micrograph particle analysis software. Larger clump size is taken to indicate greater clump strength. For lines with inducible expression that causes cell-cell adhesion, sheets of cells are formed for analysis. Cells are filtered to a standard thickness of 100 µm on a 0.22 µm nitrocellulose filter and the filter placed on agar medium under inducing conditions. When cell adhesion is complete, the sheets of cells will be peeled off the filter for further study.

Example 2

Expression of Human Collagen Genes in *Chlamydomonas*

Example 1 is repeated with the exception of human collagen is used as a transgene (SEQ ID NO:23 or SEQ ID NO:24). *Chlamydomonas* expression vectors are constructed using established recombinant DNA methods. Expression vectors are based on pSI1105, which was designed for tandem expression of proteins in *Chlamydomonas*. For constitutive and/or inducible expression, a HSP70A/RBCS2 promoter (SEQ ID NO:7) a PSAD (SEQ ID NO:9) or both in tandem are used. A PCR is conducted using primers (SEQ ID NO:10 and SEQ ID NO:11). For advanced expression control, the thiamine-sensitive 5' riboswitch THI4 (SEQ ID NO:12) is used for translational regulation, and the NIT1 $NO_3^-$ sensitive promoter for transcriptional regulation, or both in tandem for dual regulation. A PCR is conducted using primers (SEQ ID NO:13, SEQ ID NO:14, SEQ ID NO:15 and SEQ ID NO:16). Transgenes will include antigen sequences for immunolabeling. For the quantification of the cell adhesion, the quantification steps of Example 1 will be repeated.

Example 3

Expression of Claudin Protein in *Chlamydomonas*

Example 1 is repeated with the exception of claudin proteins are used as a transgene (SEQ ID NO:31, SEQ ID NO:32, SEQ ID NO:33, SEQ ID NO:34, SEQ ID NO:35, or SEQ ID NO:36). *Chlamydomonas* expression vectors are constructed using established recombinant DNA methods. Expression vectors are based on pSI105, which was designed for tandem expression of proteins in *Chlamydomonas*. For constitutive and/or inducible expression, a HSP70A/RBCS2 promoter (SEQ ID NO:7) a PSAD (SEQ ID NO:9) or both in tandem are used. A PCR is conducted using primers (SEQ ID NO:10 and SEQ ID NO:11). For advanced expression control, the thiamine-sensitive 5' riboswitch THI4 (SEQ ID NO:12) is used for translational regulation, and the NIT1 $NO_3^-$ sensitive promoter for transcriptional regulation, or both in tandem for dual regulation. A PCR is conducted using primers (SEQ ID NO:13, SEQ ID NO:14, SEQ ID NO:15 and SEQ ID NO:16). Transgenes will include antigen sequences for immunolabeling. For the quantification of the cell adhesion, the quantification steps of Example 1 will be repeated.

Example 4

Expression of Cadherin Protein in *Chlamydomonas*

Example 1 is repeated with the exception of cadherin proteins are used as a transgene (SEQ ID NO:27, SEQ ID NO:28, SEQ ID NO:29, or SEQ ID NO:30). *Chlamydomonas* expression vectors are constructed using established recombinant DNA methods. Expression vectors are based on pSI105, which was designed for tandem expression of proteins in *Chlamydomonas*. For constitutive and/or inducible expression, a HSP70A/RBCS2 promoter (SEQ ID NO:7) a PSAD (SEQ ID NO:9) or both in tandem are used. A PCR is conducted using primers (SEQ ID NO:10 and SEQ ID NO:11). For advanced expression control, the thiamine-sensitive 5' riboswitch THI4 (SEQ ID NO:12) is used for translational regulation, and the NIT1 $NO_3^-$ sensitive promoter for transcriptional regulation, or both in tandem for dual regulation. A PCR is conducted using primers (SEQ ID NO:13, SEQ ID NO:14, SEQ ID NO:15 and SEQ ID NO:16). Transgenes will include antigen sequences for immunolabeling. For the quantification of the cell adhesion, the quantification steps of Example 1 will be repeated.

Example 5

Expression of Integrin Protein Genes in *Chlamydomonas*

Example 1 is repeated with the exception of integrin proteins are used as a transgene (SEQ ID NO:25 or SEQ ID NO:26). *Chlamydomonas* expression vectors are constructed using established recombinant DNA methods. Expression vectors are based on pSI1105, which was designed for tandem expression of proteins in *Chlamydomonas*. For constitutive and/or inducible expression, a HSP70A/RBCS2 promoter (SEQ ID NO:7) a PSAD (SEQ ID NO:9) or both in tandem are used. A PCR is conducted using primers (SEQ ID NO:10 and SEQ ID NO:11). For advanced expression control, the thiamine-sensitive 5' riboswitch THI4 (SEQ ID NO:12) is used for translational regulation, and the NIT1 $NO_3^-$ sensitive promoter for transcriptional regulation, or both in tandem for dual regulation. A PCR is conducted using primers (SEQ ID NO:13, SEQ ID NO:14, SEQ ID NO:15 and SEQ ID NO:16). Transgenes will include antigen sequences for immunolabeling. For the quantification of the cell adhesion, the quantification steps of Example 1 will be repeated.

Example 6

Expression of Lysyl Oxidase in *Chlamydomonas*

Example 1 is repeated with the exception of lysyl oxidase is used as a transgene. *Chlamydomonas* expression vectors are constructed using established recombinant DNA methods. For lysyl oxidase genes, synthetic forms that have been codon-optimized for *Chlamydomonas*. Expression vectors will be based on pSI105, which was designed for tandem expression of proteins in *Chlamydomonas*. For constitutive and/or inducible expression, a HSP70A/RBCS2 promoter (SEQ ID NO:7), a PSAD (SEQ ID NO:9), or both in tandem are used. A PCR is conducted using primers (SEQ ID NO:10 and SEQ ID NO:11). For advanced expression control, the thiamine-sensitive 5' riboswitch THI4 (SEQ ID NO:12) is used for translational regulation, and the NIT1 $NO_3^-$ sensitive promoter for transcriptional regulation, or both in tandem for dual regulation. A PCR is conducted using primers (SEQ ID NO:13, SEQ ID NO:14, SEQ ID NO:15 and SEQ ID NO:16). Transgenes will include antigen sequences for immunolabeling. For the quantification of the cell adhesion the quantification steps of Example 1 will be repeated.

Example 7

Expression of Silicate Proteins in Microalgae

Example 1 is repeated with the exception that silicate protein is used as a transgene. *Chlamydomonas* expression vectors are constructed using established recombinant DNA methods. Silicate proteins are then isolated from diatom DNA by RT-PCR and cloned. Expression vectors will be based on pSI105, which was designed for tandem expression of proteins in *Chlamydomonas*. For constitutive and/or inducible expression, a HSP70A/RBCS2 promoter (SEQ ID NO:7), a PSAD (SEQ ID NO:9), or both in tandem are used. A PCR is conducted using primers (SEQ ID NO:10 and SEQ ID NO:11). For advanced expression control, the thiamine-sensitive 5' riboswitch THI4 (SEQ ID NO:12) is used for translational regulation, and the NIT1 $NO_3^-$ sensitive promoter for transcriptional regulation, or both in tandem for dual regulation. A PCR is conducted using primers (SEQ ID NO:13, SEQ ID NO:14, SEQ ID NO:15 and SEQ ID NO:16). Transgenes will include the silicate transgenes. Transgenes will include antigen sequences for immunolabeling. For the quantification of the cell adhesion the quantification steps of Example 1 will be repeated.

Example 8

Algal-CAM Construct in *Chlamydomonas* or Other Unicellular Algae

In at least one embodiment is provided a unicellular microalgae capable of expression of the Algal-CAM gene (SEQ ID NO:17, SEQ ID NO:18, SEQ ID NO:19 and SEQ ID NO:20). *Volvox carteri f. nagariensis* (UTEX#1886) were acquired from the UTEX culture collection and the *Chlamydomonas* Center culture collection (St. Paul, Minn.). *Volvox carteri f. nagariensis* (UTEX#1886) was cultured in 0.5× Bolds Modified medium with 0.5× supplemental soil water supernatant. Arginine auxotroph cell wall mutants of *C. reinhardtii* (Δ Arg7 cw-15, CC-425) were used for all *Chlamydomonas* experiments and were grown in TAP or TAP+ yeast extract with rotary shaking at 140 rpm under continuous fluorescent light of 60 μmol photons m-2s-1.

Qiagen Plant RNeasy RNA Extraction Kits (#74903) with "Shredder" columns were used as recommended by the manufacturer starting with 3-5×106 total cells. For *V. carteri* cells, the liquid N2 lysis method was used with RNase-free disposable pestles and 1.7 ml tubes. Buffer RLT and the Shredder columns were sufficient to lyse and homogenize *C. reinhardtii* cells. DNase treatment of RNA samples was carried out to eliminate genomic DNA contamination with DNase I, as recommended by the manufacturer. cDNA synthesis was carried out directly after RNA extraction and DNase treatment using the SuperScript III First-Strand Synthesis SuperMix kit as recommended by the manufacturer using oligo(dT)20 primers.

Standard recombinant DNA techniques were used to generate all constructs. The 1,323 bp Algal-CAM CDS (SEQ ID NO:19) was amplified from *V. carteri* cDNA preparations using Phusion HF DNA polymerase per the manufacturer's recommendations with oligonucleotides ACAMCDS2fwd (SEQ ID NO:37) and ACAMCDS2rev (SEQ ID NO:38). This CDS corresponds to the open reading frame encoded by the caml mRNA splice variant 2 of Algal-CAM (SEQ ID NO:20) which incorporates the C-terminal exon VIII and not the GPI associated exon IX. The Algal-CAM CDS was cloned into pCR-TOPO-2.1 as recommended by the manufacturer and confirmed by sequencing using the M13 primer pair. A *C. reinhardtii* codon-optimized green fluorescent protein sequence (cGFP) was amplified similarly using primer pairs FwdxhoIBglII (SEQ ID NO:39) and RevBamHI SEQ ID NO:40 from pKscGFP as an XhoI/BamHI amplicon with a BglII site inserted in-between the XhoI and MscI sites by the forward primer and ligated into pRbcRL(Hsp 196) using the XhoI/BamHI sites to create pRbcGFP(Hsp196). pRbcGFP (Hsp196) is a derivative of pRbcRL(Hsp 196) but with a *C. reinhardtii* codon-optimized GFP sequence inserted in place of the luciferase sequence. The expression vector, pRbcRL (Hsp196), and it's derivatives drive transcription using a truncated RBCS2 promoter flanked by enhancer elements of HSP70A and RBCS2 intron 1. Algal-CAM was subcloned in-frame and upstream of the cGFP in pRbcGFP (Hsp196) as a BglII/MscI fragment by amplification with primers that added a 5'BglII site, a 3'MscI site and removed the stop codon. In the case of derivative RbcGFP-ACAMwL, a flexible linker, (GSS)2, was added by the reverse primer using the primers Fwdw/BglII (SEQ ID NO:41) and Revw/MscI (SEQ ID NO:42) or Revw/MscI and linker (SEQ ID NO:43). This resulted in the sequence-verified constructs pRbcGFP-ACAM, with no linker, and pRbcGFP-ACAMwL, with linker added.

Co-transformation using pArg7 selectable marker and either pRbcGFP-ACAM or pRbcGFP-ACAMwL was carried out according to the nuclear glass bead method using cells at 2-6×106 cells/ml. Arginine prototrophs were selected on TAP without arginine and screened for transgene presence via PCR of the transgene with primers amplifying a recombinant 598 by region spanning the cGFP sequence and the ACAM sequence: Scnfwd1 (SEQ ID NO:44) and Scnrev1 (SEQ ID NO:45). Colonies were further screened for mRNA expression via RT-PCR or flocculation phenotype or both. Genomic DNA was extracted by incubating cells at 100° C. for 5 min in 10 mM NaEDTA followed by centrifugation.

Template cDNA preparations were screened with primers amplifying a 453 by recombinant region of the transgene that spanned the promoter region and the Algal-CAM region: ScnRTPCRfwd2 (SEQ ID NO:46) and ScnRTPCRrev2 (SEQ ID NO:47). Primers directed toward cActin mRNA were intron-spanning and amplified an mRNA-derived cDNA target of 344 bp: cActinfwd1 (SEQ ID NO:48) and cActinrev1 (SEQ ID NO:49). The cActin amplification was used as a positive mRNA/constitutive loading control. Recommended PCR reaction conditions were used with Phusion HF DNA polymerase with annealing temperature of 58° C. for 35 cycles. PCR amplicons were separated on 2% TAE agarose gels stained with ethidium bromide.

100 μl of 72 hr liquid culture was used to inoculate 3 ml of medium in 12 well culture plates that were grown for 24 hrs in the light with shaking Low magnification micrographs were then taken in the 12 well plates using an inverted Leica DMI3000 B microscope with a 2.5× objective after separating individual flocs by gentle rotary agitation. Higher magnification fluorescence micrographs were taken using a Zeiss 710 scanning confocal laser microscope at 63× magnification, 488 nm excitation, and 510 nm emission.

300 ul of 72 hr liquid culture was used to inoculate 5 ml of medium in 50 ml culture tubes and grown for 72 hrs under light with shaking Cultures were vortexed and photographed. Cultures were then left to settle for 10 min and photographed again.

Example 9

Figure 14:
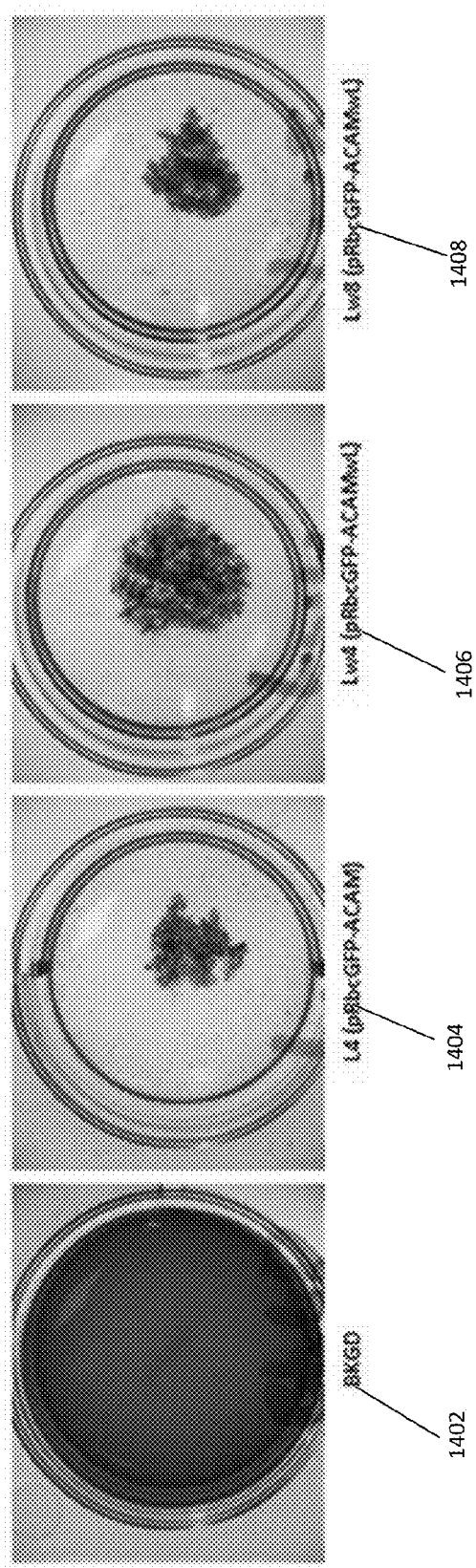
FIG. 14 shows photographs demonstrating simple self-assembly of transgenic *Chlamydomonas* strains expressing *Volvox* Algal-CAM.

Self-Assembly of Transgenic *Chlamydomonas* Strains Expressing *Volvox* Algal-CAM FIG. 14 demonstrates simple self-assembly of transgenic *Chlamydomonas* strains expressing *Volvox* Algal-CAM, a cell adhesion molecule. Photographs are of cultures growing in 12-well culture plates. Wells are 2 cm in diameter. BKGD cells are non-transformed Δ Arg7 cw-15 background strain. L4, Lw4, and Lw8 are three strains expressing *Volvox* Algal-CAM. Flocs adhere together to form large clumps. As shown in FIG. 14, self-adhesion phenotype of transgenic strains expressing Algal-CAM 1400 in three strains of *C. reinhardtii* is shown in four photographs showing the flocculation or non-flocculation of four transgenic strains, BKGD 1402, L4 1404, Lw4 1406 and Lw8 1408 growing in four growth plates. Strain BKGD 1402 indicates the non-transformed *C. reinhardtii* Δ Arg7 cw15 background strain; strain L4 1404 indicates a transformed transgenic strain with confirmed to express the Algal-CAM gene (pRbcGFP-ACAM transformants); strains Lw4 1406 and Lw8 1408 indicate transformed transgenic strains confirmed to express the Algal-CAM gene (pRbcGFP-ACAMwL transformants). The four cultures were incubated for 24 hours and photographed using a high resolution camera. Photographs were taken of cells growing in 12 well culture plates. Culture wells are 2.0 cm in diameter. Photographs were taken after lightly swirling the plates to separate and isolate individual flocculations. As shown in the photographs, BKGD 1402 does not show as coagulation or flocculation, L4 1404 acts more as a loose coagulation of smaller flocculations while Lw4 1406 (third from the left) and Lw8 1408 act as a more cohesive large flocculations.

Example 10

Heterologous Expression of Cell Adhesion Molecule Algal CAM in *Chlamydomonas reinhardtii*

Figure 15:
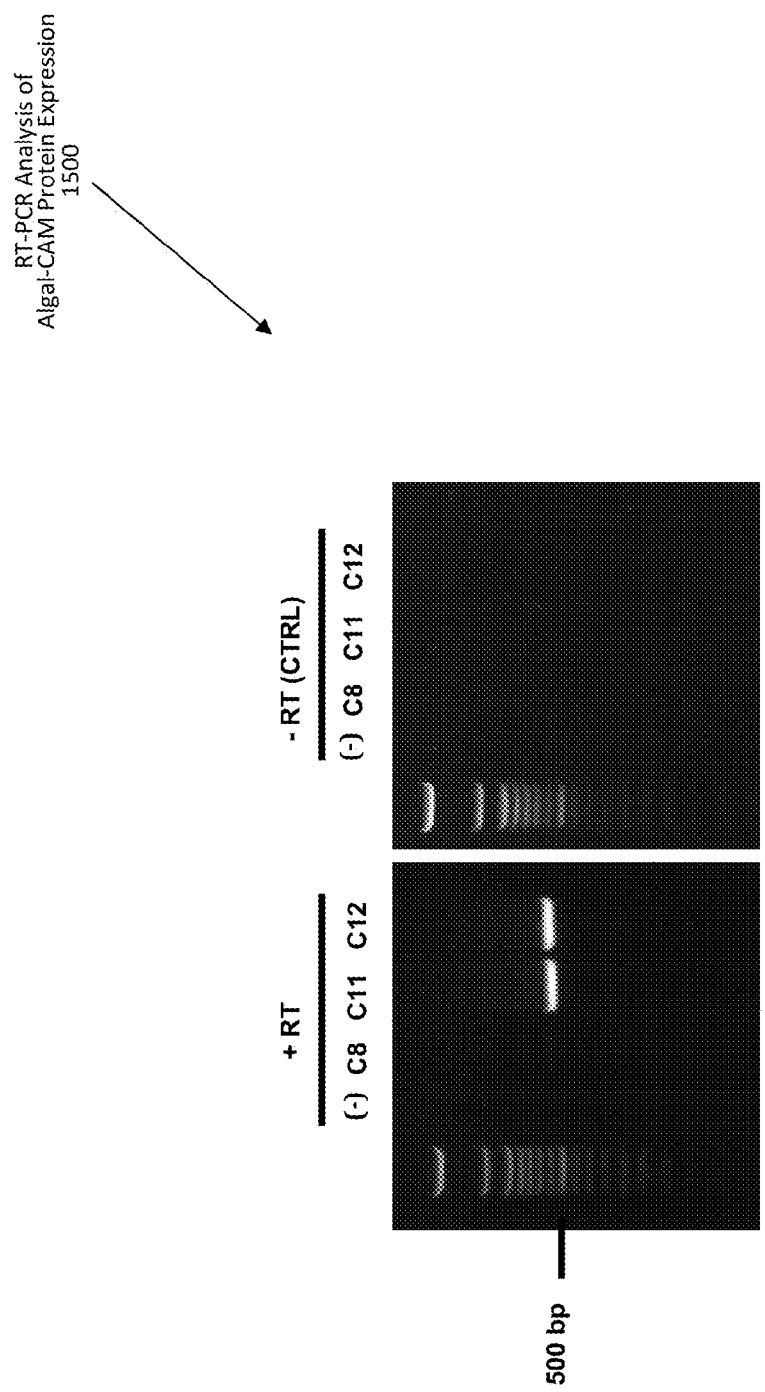
FIG. 15 shows two photographs of western blots showing transgene mRNA expression of the *Volvox* Algal-CAM protein in transgenic *Chlamydomonas*.

FIG. 15 demonstrates constitutive expression of the mRNA transcript for the heterologous cell adhesion molecule Algal CAM in *Chlamydomonas reinhardtii*. As shown in FIG. 15, two transformants (colony 11 and 12) show strong heterologous transcription of the Algal-CAM transgene: RT-PCR was performed on four different strains. Left Panel: The empty vector control strain (−) tests negative for recombinant Algal-CAM transcript while transformants C11 and C12 show high levels of transgene mRNA expression. Compared to C11 and C12, transformant colony #8 (C8) shows virtually no transcription. An Intron-I spanning forward primer was used to distinguish between transcript derived cDNA and contaminating genomic DNA (519 bp amplicon for cDNA templates and a 664 bp amplicon for genomic DNA templates when paired with the reverse primer). Right Panel: Absence of genomic DNA contamination is further confirmed by replicating the experiment using no reverse transcriptase (-RT) in the cDNA synthesis step.

Example 11

Expression, Secretion, and Localization to the Cell Wall of the Heterologous Cell Adhesion Molecule Algal CAM in *Chlamydomonas reinhardti*

Figure 16:
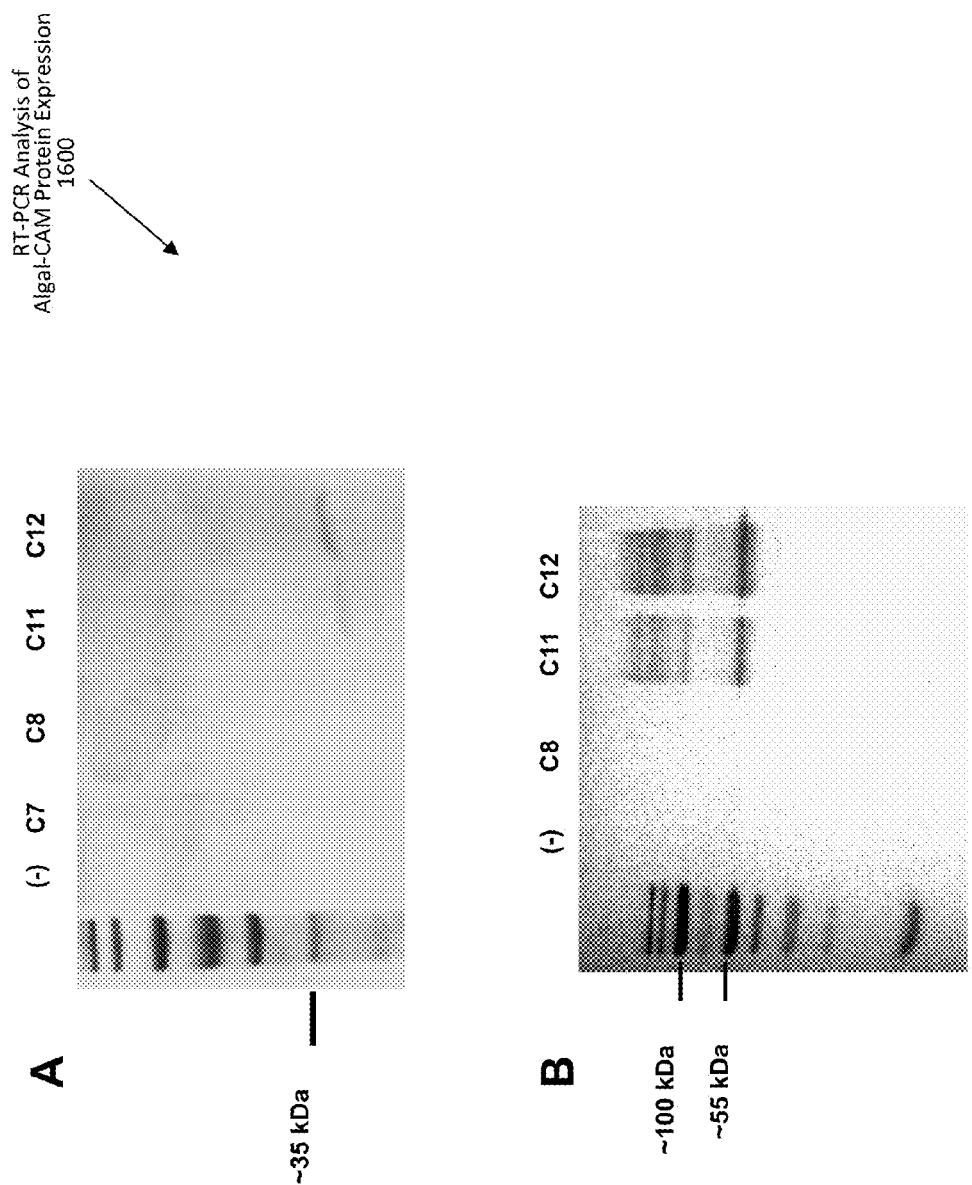
FIG. 16 shows two photographs of western blots demonstrating constitutive expression, secretion, and localization to the cell wall of the heterologous cell adhesion molecule Algal CAM from *Volvox* in *Chlamydomonas reinhardti*.

FIG. 16 demonstrates constitutive expression, secretion, and localization to the cell wall of the heterologous cell adhesion molecule Algal CAM in *Chlamydomonas reinhardti*. Following phenotypic screening, either whole cell lysates (A) or cell wall digested/inhibited media fractions (B) were assayed for heterologous protein expression via western blots using α-FLAG antibody. Heterologous Algal-CAM fusion protein was not anticipated to be found in cell lysates as it is secreted in *V. carteri*. A possible >35 kDa fusion protein degradation product or FLAG tag artifact was detected in flocculating and transcript positive crude cell lysates (C11 and C12) and not in the empty vector control (−) nor two negative transcript and non-flocculating transformants (C7 and C8). The calculated molecular mass of Algal-CAM fusion protein is 48.5 kDa and the apparent molecular mass of native *Volvox* Algal-CAM is 150 kDa when assayed using SDS-PAGE (Huber and Sumper 1994). To search for Algal-CAM in the extra cellular matrix (ECM) (B) cell preparations were digested with crude gamete auto-lysin (GLE) and then incubated for two hours under isodityrosine cross-linking inhibiting conditions. Cells were then spun down and the supernatent analyzed for Algal-CAM_FLAG fusion protein via western blot probing FLAG tag. High molecular weight bands (above 55) appear to show cross-linked fusion protein either left over from GLE treatment or inefficient cross link inhibition by 50 mM ascorbate and 5 mM tyrosine. These High molecular weight bands are also consistent with Huber and Sumper's observations of 150 kDa apparent molecular weight for Algal-CAM with broad and ladder-like banding patterns. The high molecular weight bands (in C11 and C12) could represent heavily glycosylated heterologous Algal-CAM. Bands running slightly below 55 kDa correlate to the predicted molecular weight of Algal-CAM and could represent inefficient glycosylation of overexpressed Algal-CAM in *C. reinhardtii*.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The use of the terms "a," "an," "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

We claim:

1. A method of self-assembly of photosynthetic unicells into a multicellular shape, the method comprising:
    genetically modifying one or more photosynthetic unicells, wherein said photosynthetic unicells are of the order Chlamydomonadales, for induced heterologous expression of a *Volvox* glycoprotein;
    growing and multiplying said genetically modified photosynthetic unicells capable of expressing the *Volvox* glycoprotein;
    providing a form for forming the genetically modified photosynthetic unicells capable of expressing the *Volvox* glycoprotein into a shape;
    inducing expression of the *Volvox* glycoprotein in the genetically modified photosynthetic unicells; and
    producing a multicellular shape from the genetically modified photosynthetic unicells.

2. The method of claim 1, wherein said glycoprotein is chosen from the group consisting of Algal-CAM, ISG, V1, and V2.

3. The method of claim 1, wherein said glycoprotein is expressed in the cell wall or extracellular matrix of said photosynthetic unicells.

4. The method of claim 2, wherein said glycoprotein is selected from the group consisting of SEQ ID NO: 1, SEQ ID NO:2, SEQ ID NO:3, SEQ ID NO:4, SEQ ID NO:5, SEQ ID NO:6, SEQ ID NO: 17, SEQ ID NO:18, SEQ ID NO:19, and SEQ ID NO:20.

5. The method of claim 1, wherein said expression of said glycoprotein in said photosynthetic unicells is induced through a method selected from the group consisting of: 1. removing ammonium from growth medium containing said photosynthetic unicells so as to induce activity of a NIT1 inducible promoter, 2. removing thiamine from said growth medium containing said photosynthetic unicells so as to activate translation controlled by a THI4 translational regulator, 3. using external agents to induce transcription, and 4. translation of transgenes by means of external stimuli.

6. The method of self-assembly of photosynthetic unicells into a multicellular shape of claim 1, wherein the form is chosen from scaffolds, wire frames, screens or boards.

7. The method of self-assembly of photosynthetic unicells into a multicellular shape of claim 1, wherein said shape is chosen from a sheet, board, rod, tube, or block.

* * * * *